(12) United States Patent
Walls et al.

(10) Patent No.: US 9,915,600 B2
(45) Date of Patent: Mar. 13, 2018

(54) DEVICES, SYSTEMS AND METHODS FOR DETECTING PARTICLES

(71) Applicant: Research Triangle Institute, Research Triangle Park, NC (US)

(72) Inventors: Howard Jerome Walls, Apex, NC (US); Anthony Clint Clayton, Rougemont, NC (US); Randall J. Newsome, Apex, NC (US); Paul G. Hoertz, Morrisville, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 15/048,199

(22) Filed: Feb. 19, 2016

(65) Prior Publication Data

US 2017/0241893 A1     Aug. 24, 2017

(51) Int. Cl.
    *G01N 15/14*           (2006.01)
    *G01N 21/64*           (2006.01)
    (Continued)

(52) U.S. Cl.
    CPC ......... *G01N 15/1436* (2013.01); *G01N 21/53* (2013.01); *G01N 21/645* (2013.01); *G01N 21/6486* (2013.01); *G01N 2021/4721* (2013.01); *G01N 2201/062* (2013.01); *G01N 2201/06113* (2013.01)

(58) Field of Classification Search
    CPC .......... G01N 31/00; G01N 9/32; G01N 21/53; G01N 21/645; G01N 15/1436
    See application file for complete search history.

(56) References Cited

U.S. PATENT DOCUMENTS

| 3,520,172 A | 7/1970 | Liu et al. |
| 3,849,654 A | 11/1974 | Malvin |

(Continued)

FOREIGN PATENT DOCUMENTS

| CN | 201217660 | 4/2009 |
| CN | 101738628 A | 6/2010 |

(Continued)

OTHER PUBLICATIONS

International Search Report and Written Opinion dated Dec. 22, 2014 from related application No. PCT/JP2014/074902.

(Continued)

*Primary Examiner* — David Porta
*Assistant Examiner* — Faye Boosalis
(74) *Attorney, Agent, or Firm* — David P. Gloekler; Olive Law Group, PLLC

(57) ABSTRACT

A particle detector includes a housing, a light source, and a photo-responsive material. The housing includes a sample inlet and a sample outlet, and encloses a detection cavity. The light source directs irradiating light to particles of a sample fluid flowing in the detection cavity. The photo-responsive material faces the detection cavity, and receives measurement light propagating from the particles in a plurality of measurement light paths angled relative to a longitudinal axis. The particle detector may be utilized to measure scattered light and/or light emitted due to autofluorescence. Fluids sampled may include aerosols, bio-aerosols, and liquids.

34 Claims, 27 Drawing Sheets

(51) Int. Cl.
*G01N 21/53* (2006.01)
*G01N 21/47* (2006.01)

(56) References Cited

U.S. PATENT DOCUMENTS

| | | | |
|---|---|---|---|
| 4,019,017 | A | 4/1977 | Sitek et al. |
| 4,154,669 | A * | 5/1979 | Goetz .............. G01N 27/44721 |
| | | | 204/645 |
| 4,473,296 | A | 9/1984 | Shofner et al. |
| 4,571,079 | A | 2/1986 | Knollenberg |
| 5,317,930 | A | 6/1994 | Wedding |
| 5,922,976 | A | 7/1999 | Russell et al. |
| 6,263,744 | B1 | 7/2001 | Russell et al. |
| 6,296,425 | B1 | 10/2001 | Memory et al. |
| 6,520,034 | B1 | 2/2003 | Masquelier et al. |
| 6,854,344 | B2 | 2/2005 | Cornish et al. |
| 7,140,265 | B2 | 11/2006 | McGill et al. |
| 8,030,088 | B2 | 10/2011 | McCash et al. |
| 2011/0049390 | A1 | 3/2011 | Murray et al. |
| 2012/0105839 | A1 | 5/2012 | Novosselov et al. |
| 2013/0042673 | A1* | 2/2013 | Saari-Nordhaus ..... G01N 30/84 |
| | | | 73/61.55 |
| 2013/0042893 | A1 | 2/2013 | Ariessohn et al. |
| 2014/0017839 | A1* | 1/2014 | Li ...................... H01L 31/0352 |
| | | | 438/36 |

FOREIGN PATENT DOCUMENTS

| | | | |
|---|---|---|---|
| CN | 101762819 A | 6/2010 | |
| CN | 101974419 A | 2/2011 | |
| CN | 102323111 A | 1/2012 | |
| CN | 202393920 U | 8/2012 | |
| CN | 102654445 A | 9/2012 | |
| CN | 202770678 U | 3/2013 | |
| CN | 103115802 A | 5/2013 | |
| CN | 103119417 A | 5/2013 | |
| EP | 79079 A1 | 5/1983 | |
| ES | 2030992 | 11/1992 | |
| GB | 1422188 A | 1/1976 | |
| GB | 1538056 A | 1/1979 | |
| JP | 10318905 A | 12/1998 | |
| JP | 200321219 A | 1/2003 | |
| JP | 2004239365 A | 8/2004 | |
| JP | 201277784 A | 4/2012 | |
| JP | 2012202543 A | 10/2012 | |
| KR | 101317982 B1 | 10/2013 | |
| SU | 1242768 A1 | 7/1986 | |
| SU | 1665267 A1 | 7/1991 | |
| WO | WO 9010858 A * | 9/1990 | ............ G01N 15/14 |
| WO | 2001095279 A1 | 12/2001 | |
| WO | 2012150958 A1 | 11/2012 | |
| WO | 2013123500 A1 | 8/2013 | |

OTHER PUBLICATIONS

International Search Report and Written Opinion dated Oct. 22, 2015 from related application No. PCT/US2015/046080.
Abu-Rahmah, A., et al. (2006). "Integrating nephelometer with a low truncation angle and an extended calibration scheme." Measurement Science & Technology 17(7): 1723-1732.
Agranovski, V., et al. (2003). "Real-time measurement of bacterial aerosols with the UVAPS: performance evaluation." Journal of Aerosol Science 34(3): 301-317.
Ammor, M. S. (2007). "Recent advances in the use of intrinsic fluorescence for bacterial identification and characterization." Journal of Fluorescence 17(5): 455:459.
Chow, J. C., et al. (2002). "Comparability between PM2.5 and particle light scattering measurements." Environmental Monitoring and Assessment 79(1): 29-45.
Greenwood, D. P. et al. (2009). "Optical Techniques for Detecting and Identifying Biological-Warfare Agents." Proceedings of the Ieee 97(6): 971-989.
Hasan, H., et al. (1983). "Integrating nephelometer response corrections for biomodal size distributions." Aerosol Science and Technology 2(4): 443-453.
Hill, S. C., et al. (2013). "Fluorescence of bioaerosols: mathematical model including primary fluorescing and absorbing molecules in bacteria." Optics Express 21(19): 22285-22313.
Jeys, T. H., et al. (2007). "Advanced trigger development." Lincon Laboratory Journal 17(1): 29-62.
Penaloza, M. A. (199). "Deriving the basic cell-reciprocal integrating nephelometer equation and its use for calibration purposes: a comprehensive approach." Measurement Science and Technology 10(1): R1-R15.
Saari, S., et al. (2014). "Performance of Two Fluorescence-Based Real-Time Bioaerosol Detectors: BioScout vs. UVAPS." Aerosol Science and Technology 48(4): 371-378.
Sloane, C. S., et al. (1991). "Measurements of aerosol-particle size-improved precision by simultaneous use of optical-particle counter and nephelometer." Aerosol Science and Technology 14(3): 289-301.
Varma, R., et al. (2003). "Toward an ideal integrating nephelometer." Optics Letters 28(12): 1007-1009.
International Preliminary Report on Patentability issued in PCT Application No. PCT/US2015/046076 dated Feb. 21, 2017.
International Preliminary Report on Patentability issued in PCT Application No. PCT/US2015/046080 dated Feb. 21, 2017.
Pahalawatta et al.: "Particle detection and classification in photo-electric smoke detectors using image histogram features.", International Conference on Digital Image Computing: Techniques and Applications (DICTA),pp. 1-8 (2013).
Wallace, Lance: "Real-time measurements of black carbon indoors and outdoors: a comparison of the photoelectric aerosol sensor and the aethalometer, Aerosol", Science and Technology, vol. 39, No. 10, pp. 1015-1025 (2005).

* cited by examiner

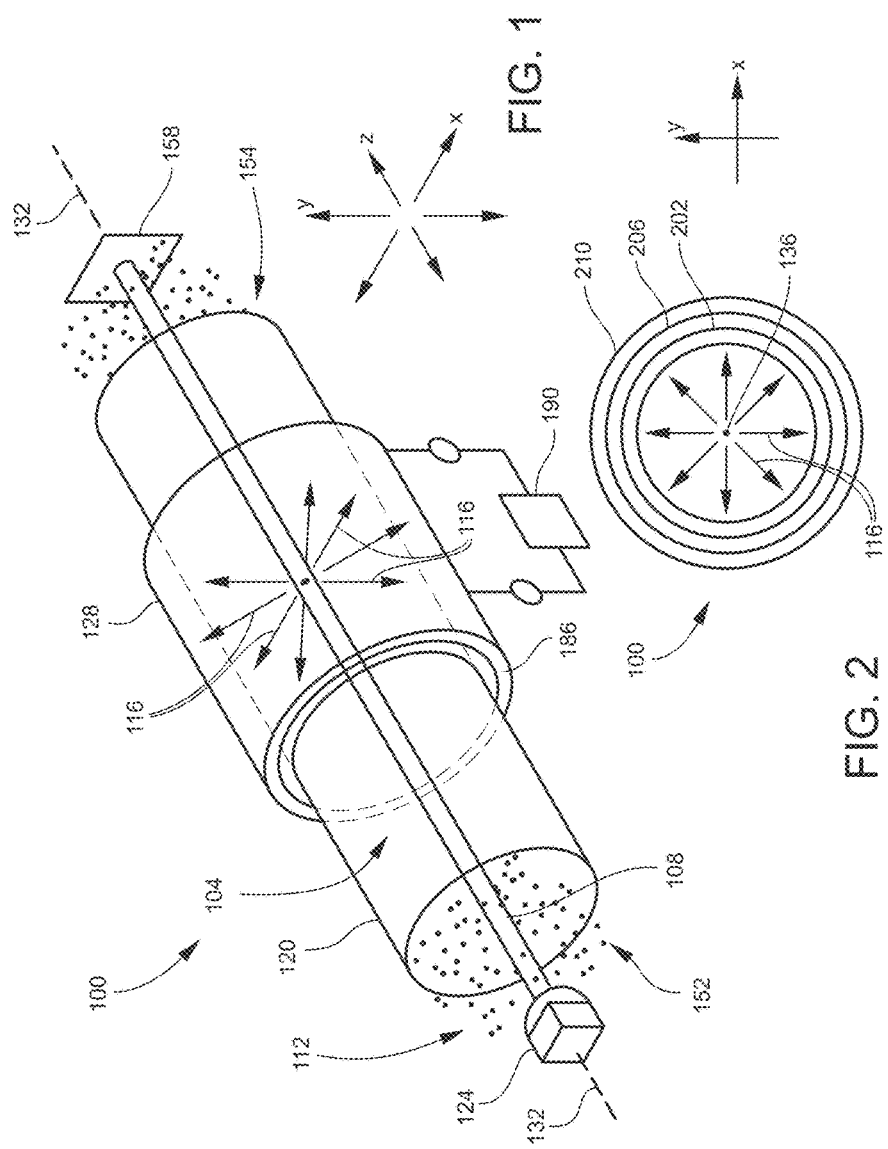

DEVICES, SYSTEMS AND METHODS FOR DETECTING PARTICLES

RELATED APPLICATIONS

This application is a continuation-in-part of International Application No. PCT/2015/046076, filed Aug. 20, 2015, titled "DEVICES, SYSTEMS, AND METHODS FOR DETECTING PARTICLES," which claims the benefit of U.S. Provisional Patent Application Ser. No. 62/039,512, filed Aug. 20, 2014, titled "DEVICES, SYSTEMS AND METHODS FOR DETECTING PARTICLES," and U.S. Provisional Patent Application Ser. No. 62/039,519, filed Aug. 20, 2014, titled "SYSTEMS, DEVICES, AND METHODS FOR FLOW CONTROL AND SAMPLE MONITORING CONTROL," the contents of each of which are incorporated by reference herein in their entireties.

TECHNICAL FIELD

The present invention relates to optical-based detection of particles in an aerosol or liquid, including measurement of light scattering and autofluorescence.

BACKGROUND

Detection of particles and colloids suspended in a fluid medium for measurement of concentration or other properties is useful in a variety of applications such as medical diagnostics, scientific research, air quality measurements, and threat detection. Examples include measurement of the concentration of particles suspended in a liquid such as proteins in blood, and airborne particles in inside environments such as building as well as outside environments.

One application of note is the measurement of the concentration and other properties of airborne particles (or particulate matter, PM) in aerosols. The United States Environmental Protection Agency (US EPA) has set exposure standards for coarse PM (between 10 μm and 2.5 μm, $PM_{10}$) and fine PM (less than 2.5 μm, $PM_{2.5}$) due to the importance of aerosol concentration in the air and its health effects. Aerosol concentrations are also important in the manufacturing industry for both protection of the health of workers and preventing contamination in the manufacturing process.

A class of aerosols of special interest is bioaerosols. Bioaerosols include bio-particles such as fungus spores, bacteria spores, bacteria, viruses, and biologically derived particles (skin cells, detritus, etc.). Some bioaerosols cause chronic and/or acute health effects, for example certain strains of black mold or *Bacillus anthracis* (causative bacteria of anthrax). Bioaerosol concentrations are important in maintaining safe hospitals, clean food processing, pharmaceutical and medical device manufacturing, and air quality. Airborne spread of diseases is of particularly concern from a public health perspective. Aerosolized bioagents can also be used by terrorists to harm civilian or military populations.

Measurement (sensing) of aerosol and bioaerosol concentration is typically accomplished with optical techniques. Aerosol (e.g., solid and liquid particles ≤10 μm dispersed in air) concentration measurement is readily achieved by various light scattering measurements. See Hinds, *Aerosol Technology*, New York, John Wiley & Sons, Inc. (1982); Lehtimaki and Willeke, Measurement Methods, *Aerosol Measurement*, Willeke and Baron, New York, Van Norstrand Reinhold, 112-129 (1993). The most accurate method entails the use of a single particle counter that focuses a stream of aerosol into a detection cavity where light scattering from a long wavelength (>650 nm) laser is measured. Precision optics are required to collect and focus the scattered light (while excluding the source light) onto a photon detector. The photon detectors are made from silicon or photocathode materials (e.g., indium gallium arsenide) that undergo the photoelectric effect (convert photons to electrons). These materials are packaged into detectors that offer high amplification of the signal from the photons, such as photomultiplier tubes (PMTs) and avalanche photodiodes (APDs). These detectors have active detection areas that are small (less than 25 $mm^2$) and limited to planar geometries. Moreover, these detectors cost $100 or more, often exceeding $1,000 in the case of a high sensitivity PMT.

Autofluorescence (or intrinsic fluorescence) excited by ultraviolet (UV) and blue light is well-developed for detection of bioaerosols. See Hairston et al., "Design of an instrument for real-time detection of bioaerosols using simultaneous measurement of particle aerodynamic size and intrinsic fluorescence," *Journal of Aerosol Science* 28(3): 471-482 (1997); Ho, "Future of biological aerosol detection," *Analytical Chimica Acta* 457(1): 125-148 (2002); Agranovski et al., "Real-time measurement of bacterial aerosols with the UVAPS: Performance evaluation," *Journal of Aerosol Science* 34(3): 301-317 (2003); Ammor, "Recent advances in the use of intrinsic fluorescence for bacterial identification and characterization," *Journal of Fluorescence* 17(5): 455-459 (2007); Ho et al., "Feasability of using real-time optical methods for detecting the presence of viable bacteria aerosols at low concentrations in clean room environments," *Aerobiologia* 27(2): 163-172 (2011). Exploiting autofluorescence of microbes is widely viewed as one of the most cost-effective means to detect a potential biological threat. Bioaerosol detectors typically use a combination of light scattering (measurement of general aerosol concentration and properties) and autofluorescence (detection of emitted photons). Bioaerosol detectors based on autofluorescence rely on fluorescence from molecular fluorophores that reside within the bio-particle. For clean bio-particles, this fluorescence can be primarily attributed to biochemicals such as tryptophan and tyrosine (amino acids), nicotinamide adenine dinucleotide (NADH), and riboflavin. NADH and riboflavin absorb and emit longer wavelengths than the amino acids. See Jeys et al., "Advanced trigger development," *Lincon Laboratory Journal* 17(1): 29-62 (2007); Hill et al., "Fluorescence of bioaerosols: mathematical model including primary fluorescing and absorbing molecules in bacteria," *Optics Express* 21(19): 22285-22313 (2013). The ability to use longer wavelength excitation sources such as light-emitting diodes (LEDs, excitation wavelength $\lambda_{exc}$>360 nm) or lasers ($\lambda_{exc}$>400 nm) may reduce the cost of such instruments.

Traditional bioaerosol particle detectors rely on three main components: (1) an excitation source of appropriate wavelength to excite a targeted fluorophore or collection of fluorophores; (2) precision optics (lenses and mirrors) on both the excitation and emission side to focus the source onto the narrow air stream and to enhance the collection of emitted photons from biological particles; and (3) a high gain detector such as a PMT or APD. Elastic light scattering from visible or long wavelengths is utilized to count and sometimes size the particles. Autofluorescence of biomolecules is utilized to detect microorganisms. The typical bioaerosol detector utilizes a small detection cavity, with fluorescence active volumes on the order of $1 \times 10^{-4}$ $cm^3$, making the window for detection of each bioaerosol particle exceedingly small. At typical flow rates, a bioaerosol particle resides within the excitation volume for 1-10 μs on average. See Hairston et al. (1997). As a result, emitted and scattered light from each bioaerosol particle is collected virtually on an individual basis, and the signal is weak. See Greenwood et al., "Optical Techniques for Detecting and Identifying Biological Warfare Agents," *Proceedings of the IEEE* 97(6): 971-989 (2009). This weak signal thus requires the use of precision lenses and mirrors to collect the weak signal and focus it onto the high gain detector (e.g., PMT or APD).

Measurement of aerosol and bioaerosol concentration and changes in concentration is possible via a variety of commercially available instruments such as the Laser Aerosol Spectrometer for aerosols (TSI Incorporated, Shoreview, Minn., USA), the Ultraviolet Aerodynamic Particle Sizer for bioaerosols (TSI Incorporated), the Wideband Integrated Bioaerosol Sensor (WIBS-4) for bioaerosols (Droplet Measurement Technologies, Boulder, Colo., USA), and the instantaneous biological analyzer and collector (FLIR Systems, Inc., Wilsonville, Oreg., USA). However, such instruments can exceed $10,000 in cost making wide spread use cost prohibitive. Furthermore, having a sufficiently dense sensor network of aerosol/bioaerosol sensors (i.e., multiples of these instruments in communication with a central network) is cost prohibitive. The high cost of a sensor network also means that capitalizing on responsive systems is challenging. For example, it would be desirable to provide several bioaerosol sensors positioned throughout a hospital or other building and networked with the building's control systems to maintain a safe environment and respond to a change in bioaerosol concentration, such as by diverting airflow or indicating the need for maintenance of filters and air handlers.

Aerosol exposure monitors have been developed that acquire data from aerosol while the aerosol is sampled in real time during a prescribed sampling period (integration period). Such devices may employ inertial impactors for aerodynamic sizing, particle collection filters for collection and subsequent analysis, and nephelometers for measuring particle concentration by acquiring light scattering data in real time. Examples of such devices are described in International Publication No. WO 2013/063426, filed Oct. 26, 2012, titled "AEROSOL EXPOSURE MONITORING," the content of which is incorporated by reference herein in its entirety. Also known are turbidometers, which measure the concentrations of particles such as cells in solution.

International Application No. PCT/2015/046076, filed Aug. 20, 2015, titled "DEVICES, SYSTEMS, AND METHODS FOR DETECTING PARTICLES," the content of which is incorporated by reference herein in its entirety, discloses particle detectors that utilize large-area, photo-responsive detectors (e.g., photovoltaic detectors, photoelectric detectors, etc.) to detect photons scattered or emitted by fluid-borne particles irradiated by a photon source (or "light" source). The scatter of photons from the aerosol particles is proportional to the aerosol concentration and its scattering cross-section. Biological particles (i.e., bioaerosols) are detected by exploiting stimulated (or intrinsic) fluorescence. Certain molecules associated with bioparticles fluoresce when irradiated with short wavelengths from UV to blue. The scattered (total aerosol) or emitted (bioaerosol) photons are thus proportional to the aerosol and bioaerosol concentration. An advantageous feature disclosed in this application is the use of a large conformal detector to provide direct detection of photons from multiple angles in a large detection cavity. The conformal detector is formed by a flexible photo-responsive material such as amorphous silicon.

There is an ongoing need for devices and methods for measurement of particles in aerosols, bioaerosols, and liquids to obtain data relating to concentration and other properties of particles. There is also a need for such devices that operate effectively with simplified designs geometries, and a reduced number and cost of precision parts. There is also a need for such devices that require less cost and effort to fabricate, operate, and maintain such devices. There is also a need for further improvements in the signal-to-noise ratio and sensitivity of such devices.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a particle detector includes: a housing comprising a sample inlet and a sample outlet, and enclosing a detection cavity having a cavity length along a longitudinal axis, wherein the housing defines a flow path for a sample fluid from the sample inlet, through the detection cavity, and to the sample outlet; a light source configured for directing irradiating light through the detection cavity to particles of the sample fluid flowing in the detection cavity; and a photo-responsive material facing the detection cavity and positioned along at least a portion of the cavity length at a radial distance from the longitudinal axis, the photoelectric material having a flat planar geometry, wherein the photo-responsive material is configured for receiving measurement light propagating from the particles in a plurality of measurement light paths angled relative to the longitudinal axis.

According to another embodiment, a particle detector includes: a housing comprising a sample inlet and a sample outlet, and enclosing a detection cavity having a cavity length along a longitudinal axis, wherein the housing defines a flow path for a sample fluid from the sample inlet, through the detection cavity, and to the sample outlet, wherein the cavity comprises a first detection zone and a second detection zone downstream from the first detection zone; a first light source configured for directing a first irradiating light to particles of the sample fluid flowing in the first detection zone; a second light source light source configured for directing a second irradiating light to particles of the sample fluid flowing in the second detection zone; and a photo-responsive material facing the detection cavity and positioned along at least a portion of the cavity length at a radial distance from the longitudinal axis, wherein the photo-responsive material is configured for receiving measurement light propagating from the particles in a plurality of measurement light paths angled relative to the longitudinal axis.

According to another embodiment, a particle detector includes: a housing comprising a sample inlet and a sample outlet, and enclosing a detection cavity having a cavity length along a longitudinal axis, wherein: the housing defines a flow path for a sample fluid from the sample inlet, through the detection cavity, and to the sample outlet; the sample inlet comprises an axial inlet section on the longitudinal axis; the sample outlet comprises an axial outlet section on the longitudinal axis; the axial inlet section and the axial outlet section having respective maximum radial dimensions along a radial direction orthogonal to the longitudinal axis; and the detection cavity has a characteristic dimension in a range from 0.1% to 200% greater than the characteristic dimension of the axial inlet section and the axial outlet section; a light source configured for directing irradiating light along the longitudinal axis to particles of the sample fluid flowing in the detection cavity; and a photo-responsive material facing the detection cavity and positioned along at least a portion of the cavity length at a radial distance from the longitudinal axis, wherein the photo-responsive material is configured for receiving measurement light propagating from the particles in a plurality of measurement light paths angled relative to the longitudinal axis.

According to another embodiment, a particle detector includes: a housing comprising a sample inlet and a sample outlet, and enclosing a detection cavity having a cavity length along a longitudinal axis, wherein the housing defines a flow path for a sample fluid from the sample inlet, through the detection cavity, and to the sample outlet; a light source configured for directing irradiating light along the longitudinal axis to particles of the sample fluid flowing in the detection cavity; a plurality of mirrors in the detection cavity, wherein: the detection cavity has a dimension along a transverse axis orthogonal to the longitudinal axis; and the mirrors are configured for reflecting the irradiating light one or more times such that the irradiating light traverses the detection cavity two or more times along directions having a component along the transverse axis; and a photo-responsive material facing the detection cavity and positioned along at least a portion of the cavity length at a radial distance from the longitudinal axis, wherein the photo-responsive material is configured for receiving measurement light propagating from the particles in a plurality of measurement light paths angled relative to the longitudinal axis.

According to another embodiment, a particle detector includes: a housing comprising a sample inlet and a sample outlet, and enclosing a detection cavity having a cavity length along a longitudinal axis, wherein the housing defines a flow path for a sample fluid from the sample inlet, through the detection cavity, and to the sample outlet; a light source configured for directing irradiating light along the longitudinal axis to particles of the sample fluid flowing in the detection cavity; a beam chopper configured for chopping the irradiating light; and a photo-responsive material facing the detection cavity and positioned along at least a portion of the cavity length at a radial distance from the longitudinal axis, wherein the photo-responsive material is configured for receiving measurement light propagating from the particles in a plurality of measurement light paths angled relative to the longitudinal axis.

According to another embodiment, a method for measuring particles in a sample fluid includes: flowing the sample fluid through a detection cavity positioned on a longitudinal axis; directing an irradiating light through the detection cavity to irradiate particles in the sample fluid, wherein the particles emit measurement light in response to the irradiation; and receiving at a photo-responsive material measurement light propagating from the particles in a plurality of measurement light paths angled relative to the longitudinal axis, the photo-responsive material facing the detection cavity along at least a portion of the cavity length.

In some embodiments, the sample fluid is an aerosol.

In other embodiments, the sample fluid is a liquid.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 1 is a schematic perspective view of an example of a particle detector according to some embodiments of the present disclosure.

FIG. 2 is a schematic cross-sectional view (x-y plane) of the particle detector illustrated in FIG. 1, taken at an arbitrary point along a longitudinal axis (z-axis).

DETAILED DESCRIPTION

Figure 3:
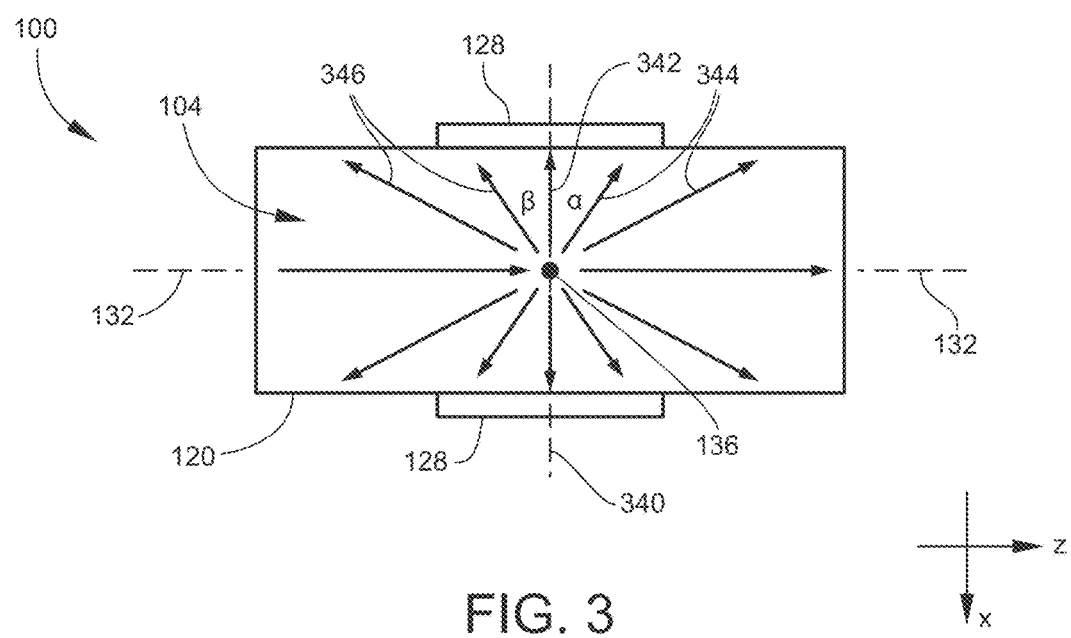
FIG. 3 is a schematic plan view of the particle detector illustrated in FIG. 1, arbitrarily taken as the x-z plane.

As used herein, the term "aerosol" generally refers to an assembly of liquid or solid particles (or particulates, or particulate matter) suspended in a gaseous medium long enough to be observed and measured. The size of aerosol particles typically ranges from about 0.001 μm to about 100 μm. See Kulkarni et al., Aerosol Measurement, 3$^{rd}$ ed., John Wiley & Sons, Inc. (2011), p. 821. The term "gaseous fluid" generally refers to a gas (or gaseous fluid, or gas-phase fluid). A gas may or may not contain liquid droplets or vapor, and may or may not contain aerosol particles. An example of a gas is, but is not limited to, ambient air. An aerosol may thus be considered as comprising particles and a gas that entrains or carries the particles.

As used herein, the term "bioaerosol" generally refers to an aerosol in which one or more bio-particles are suspended or carried. The term "bio-particle" generally refers to a biological material, or the combination of a biological material and a non-biological particle on which the biological material is carried. That is, a biological material may itself be a particle freely suspended in an aerosol, or may be carried on a non-biological particle such that the biological material and the non-biological particle are suspended together in the aerosol. The biological material may be carried on the non-biological particle by any mechanism such as, for example, entrapment, embedment, adhesion, adsorption, attractive force, affinity, etc. Examples of biological materials include, but are not limited to, spores (e.g., fungal spores, bacterial spores, etc.), fungi, molds, bacteria, viruses, biological cells or intracellular components, biologically derived particles (e.g., skin cells, detritus, etc.), etc.

As used herein, for convenience the term "aerosol" generally encompasses the term "bioaerosol" and the term "particle" generally encompasses the term "bio-particle," unless indicated otherwise or the context dictates otherwise.

As used herein, the term "fluid" generally encompasses the term "liquid" as well as term "gas," unless indicated otherwise or the context dictates otherwise. Particles suspended or carried in a liquid, as well as particles suspended or carried in an aerosol, may be detected by devices and methods disclosed herein.

As used herein, the term "light" generally refers to electromagnetic radiation, quantizable as photons. As it pertains to the present disclosure, light may propagate at wavelengths ranging from ultraviolet (UV) to infrared (IR). In the present disclosure, the terms "light," "photons," and "radiation" are used interchangeably.

As used herein, a material is "optically transparent" if it is able to efficiently pass (with minimal optical transmission loss) light of a desired wavelength or range of wavelengths.

FIG. 1 is a schematic perspective view of an example of a particle detector 100 according to some embodiments. Generally, the particle detector 100 is configured for defining (e.g., containing or enclosing) a detection cavity 104 (or sample volume) through which a particle-laden sample fluid (i.e., aerosol or liquid) may flow, producing one or more beams 108 of irradiating light (or source light) of one or more selected wavelengths, directing the beam(s) 108 into the detection cavity 104 to enable particles 112 in the detection cavity 104 to interact with the irradiating light incident on the particles 112, and collecting (receiving) measurement light (or emission light) emitted from the particles 112 in response to the irradiation. The particle detector 100 is configured for collecting measurement light over a large detection area (i.e., a large photon collection area), via a plurality of paths 116 over which the measurement light propagates, as partially depicted by rays in FIG. 1. For these purposes, the particle detector 100 may include a housing 120 or other structure for defining a flow-through detection cavity 104, one or more light (photon) sources 124 for producing one or more beams 108 of irradiating light, and one or more light detectors (or sensors) 128 for collecting measurement light over a plurality of different paths 116.

The particle detector 100 may be operated to acquire particle data in real time as sample fluid flows through the particle detector 100.

In the present context, "irradiating" light refers to the light produced by the light source 124 and utilized to irradiate particles in the detection cavity 104, as distinguished from measurement light and as also distinguished from background light (i.e., non-analytical light that would only contribute to background signal noise, such as ambient light). In the present context, "measurement" light refers to the light emitted from the particles in response to the irradiation. Measurement light may be light scattered (reflected) from the particles or fluorescent light emitted from the particles. The particle detector 100 may be configured for measuring scattered light and/or fluorescently emitted light. The particle detector 100 may be configured for measuring scattered light and fluorescently emitted light simultaneously or sequentially.

As regards scattered light, the particle detector 100 may be configured in particular for measuring elastically scattered light. Irradiating light incident on a particle may be elastically scattered from the particle at the same wavelength as the irradiating light, in accordance with the particle's size and shape and the difference in the index of refraction of the particle and that of the sample fluid. The scattering mode may be Rayleigh scattering, Mie scattering, or geometric scattering, depending on the size of the particle relative to the wavelength of the irradiating light. As regards fluorescently emitted light, the irradiating light may be utilized as an excitation light for inducing autofluorescence in the fluorophores of a particle (particularly a bio-particle). That is, irradiating light of an appropriate wavelength or wavelength range incident on a fluorophore-containing particle may be absorbed by the particle and thereby induce the particle to fluoresce, i.e., emit light at a different (typically longer) wavelength or wavelength range.

Generally, measurement light may propagate from an irradiated particle in any of a large number of directions relative to a longitudinal axis 132, as further shown in FIGS. 2 and 3. For reference purposes, the longitudinal axis 132 may be considered as the z-axis, and the cross-sectional plane orthogonal to the longitudinal axis 132 may be considered as the x-y plane. FIG. 2 is a schematic cross-sectional view (x-y plane) of the particle detector 100 taken at an arbitrary point along the longitudinal axis 132. An irradiated particle 136 has been arbitrarily located directly on the longitudinal axis 132. As shown in FIG. 2, most or all paths 116 along which the measurement light propagates have a radial component relative to the longitudinal axis 132. FIG. 3 is a schematic plan view of the particle detector 100. The plan view has been arbitrarily taken as the x-z plane, with the understanding that rotating the particle detector 100 ninety degrees about the longitudinal axis 132 to the y-z plane would yield essentially the same view. The x-y plane in which the irradiated particle lies at the instant of time at or shortly after irradiation is indicated by a vertical dashed line 340. As shown in FIG. 3, the paths or directions along which the measurement light propagates may include purely radial paths 342, forward-angle paths 344, and back-angle paths 346, relative to the x-y plane 340. In the present context, a purely radial path lies 342 substantially in the x-y plane 340, a forward-angle path 344 is oriented at some positive angle α relative to x-y plane 340 (i.e., has both a radial component and an axial component pointed in the downstream direction), and a back-angle path 346 is oriented at some negative angle β relative to x-y plane 340 (i.e., has both a radial component and an axial component pointed in the upstream direction). As described further below, the light detector 128 is capable of capturing photons propagating over a large number of purely radial paths 342, forward-angle paths 344, and back-angle paths 346 emanating from an irradiated particle 136.

Referring again to FIG. 1, the housing 120 or other structure defining the detection cavity 104 may surround or enclose a chamber or interior about the longitudinal axis 132. The chamber or interior may be coextensive with, or at least may include, the detection cavity 104. The housing 120 (or a portion thereof defining the detection cavity 104) may be generally symmetrical about the longitudinal axis 132 such that the longitudinal axis 132 is the central axis of the housing 120 (or housing portion defining the detection cavity 104). In some embodiments, the housing 120 (or housing portion defining the detection cavity 104) may be generally cylindrical as illustrated in FIG. 1, while in other embodiments may be spherical or polygonal. The housing 120 may be configured such that the detection cavity 104 is elongated along the longitudinal axis 132. As one example of an elongated geometry, the length of the detection cavity 104 along the longitudinal axis 132 may be greater than its cross-sectional dimension. In the present context, the term "cross-sectional dimension" refers to the maximum dimension that characterizes the size of the detection cavity's cross-section (cross-sectional flow area) in the plane orthogonal to the longitudinal axis 132 (e.g., the diameter of a circular cross-section, the major axis of an elliptical cross-section, or the length of a side or distance between opposing corners of a polygonal cross-section). The housing 120 includes a sample inlet 152 and a sample outlet 154 positioned such that the housing 120 defines a sample flow path from the sample inlet 152, through the detection cavity 104, and to the sample outlet 154. The sample inlet 152 and sample outlet 154 are typically open to the ambient environment outside the particle detector 100. The axial length of the detection cavity 104 may defined between a first end into which sample fluid is received and an axially opposite second end from which sample fluid is discharged. Depending on the configuration of the housing 120, the first end of the detection cavity 104 may generally correspond to (or be located proximal to) the sample inlet 152, and the second end of the detection cavity 104 may generally correspond to (or be located proximal to) the sample outlet 154.

The light source(s) 124 may be any light source suitable for producing irradiating light of a selected wavelength. Typically, the selected wavelength is a single wavelength, which may be a predominant wavelength or peak wavelength (or center wavelength) in a case where the light source 124 emits photons in a narrow wavelength band around the selected wavelength. The irradiating wavelength or wavelengths may be selected for implementing a certain type of measurement, such as scattered light or fluorescent light. Examples of light sources 124 include, but are not limited to, light emitting diodes (LEDs), lasers, laser diodes (LDs), and lamps configured for emitting light predominantly at a peak or center wavelength. The power at which the light source 124 emits irradiating light may be on the order of watts (e.g., 0.5 to 10 W), although more generally no limitation is placed on the output power of the light source 124. The light source 124 may be configured for continuous wave (CW) and/or pulsed operation. The light source 124 may be positioned relative to the detection cavity 104 such that the beam 108 of irradiation light is coaxial or substantially coaxial with the longitudinal axis 132. The light source 124 may be mounted to the housing 120 or other structure of the particle detector 100 by any suitable means.

The light source 124 may be mounted at or proximal to the first end of the detection cavity 104, such that the irradiation light propagates generally parallel with and in the same direction as the sample fluid flows through the detection cavity. Depending on the type of light source 124 utilized, the beam 108 may be coherent or non-coherent (diverging). The beam 108 may provide a generally cylindrical particle irradiation region within the detection cavity 104 of large cross-section and thus large volume, as opposed to a line or point generated by a conventionally focused laser beam. The cross-section of the beam 108 may be circular or elliptical. The relatively large volume of the beam 108 may result in increased sensitivity and lowered limit of detection (LOD) of the particle detector 100. In some embodiments, the beam 108 has a cross-sectional dimension (e.g., diameter or major axis) in a range from 0.4 mm to 4 cm (4000 mm). In some embodiments, the beam 108 has a cross-sectional area in a range from 1% to 80% of the cross-sectional area of the detection cavity 104.

The light source 124 may be configured for emitting the irradiating light at an irradiating wavelength selected for the type of measurement to be made. In some embodiments, the irradiating wavelength is in a range from 250 to 1500 nm. In various embodiments, the irradiating wavelength may be in the ultraviolet range, the visible range, or the infrared range. For measuring scattered light, the light source 124 may be selected based on factors such as low cost, emission at an irradiating wavelength that does not induce autofluorescence, etc. For measuring fluorescent emission, the light source 124 may be selected based on irradiating wavelength needed to excite certain bio-particles of interest. In some embodiments, longer irradiating wavelengths may be utilized for detecting scattered radiation while shorter irradiating wavelengths may be utilized for exciting fluorophores. For example, visible to long wavelengths such as violet (e.g., 405 nm) to infrared (IR, e.g., 900 nm) may be utilized for detecting scattered radiation, with red (e.g., 650 nm) to near IR wavelengths being typical in some embodiments. As another example, ultraviolet (UV) to blue wavelengths (e.g., 365 to 450 nm) may be utilized for exciting fluorophores. The TABLE below provides ground- and excited-state properties of a few biologically relevant fluorophores, nicotinamide adenine dinucleotide (NADH) and riboflavin, as well as an experimental surrogate, 2% Tinopal-on-Syloid, which is Syloid® silica powder (W.R. Grace and Company, Columbia, Md., USA) tagged with 2% Tinopal® CBS X florophore (BASF, Florham Park, N.J., USA).

In some embodiments, the particle detector 100 may include a light trap 158 (optical "beam dump") as shown for example in FIG. 1. The light trap 158 may be positioned in optical alignment with the light source 124, on the opposite side of the detection cavity 104 as the light source 124. Generally, the light trap 158 may have any configuration suitable for effectively absorbing light and preventing light from being reflected back into the detection cavity 104. Various configurations for light traps are known to persons skilled in the art. As examples, the light trap 158 may include a plate or cavity that is opaque ("optically black") or anti-reflective, or at least the surface(s) of such plate or cavity facing the detection cavity 104 (or coating on the surface) is opaque or anti-reflective. The light trap 158 may include geometries or structures configured for trapping light as appreciated by persons skilled in the art. If needed, the light trap 158 may include a heat sink or other means for removing heat from the light trap 158.

In some embodiments, if needed or desired, the particle detector 100 may include a device (one or more components) configured for preventing stray light from impinging on the light detector 128. Generally, stray light is any light having no analytical value such that measurement of the light by the light detector 128 is undesired. An example of stray light is irradiation light directly impinging on the light detector 128 without having first interacted with a particle to produce scattered or fluorescent light. Stray light elevates the detector output signal produced by the light detector 128 even in the absence of particles in the detection cavity 104, and thus may contribute to a large background (or baseline) signal that lowers the signal-to-noise (S/N) ratio of the particle detector 100, and may also convolute the measurement data. It is desirable to minimize the background signal to stay within the sensitive part of the response curve of the light detector 128. Testing has demonstrated that reducing the baseline voltage response of the light detector 128 from 1 volt (V) to a few millivolts (mV) dramatically lowered the LOD for aerosol from 1,000s #/cm$^3$ to less than 100 #/cm$^3$.

Figure 4:
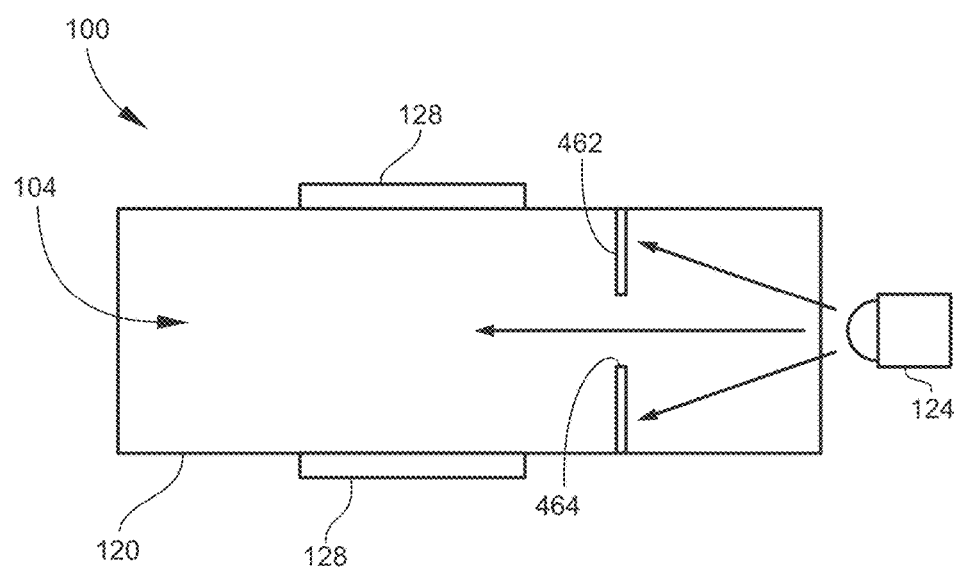
FIG. 4 is a schematic plan view of the particle detector illustrated in FIG. 1, illustrating an example of a stray light blocking device that may be utilized in the particle detector.

FIG. 4 schematically illustrates an example of a device in the form of a plate 462 (or wall, baffle, etc.) having an aperture 464. Generally, the plate 462 may be located optically "downstream" of the light source 124, i.e., optically between the light source 124 and the light detector 128. The plate 462, or at least the surface of the plate 462 (or a coating on the surface) facing the light detector 128, may be opaque or anti-reflective to absorb irradiation light and any other stray light. Thus the plate 462 serves as a photon loss surface, blocking stray light that might otherwise reach the light detector 128. Meanwhile, the aperture 464 allows light (and sample fluid) to pass through the plate 462 along paths in the vicinity of the longitudinal axis 132, thereby ensuring that such light interacts with particles and is likely to be irradiation light of the intended wavelength. The axial position of the plate 462 relative to the light source 124 and the light detector 128, and the size of the aperture 464, may

TABLE

| Fluorophore | Total Fluorophores Per Particle, (#/particle) | Extinction Coefficient, (M$^{-1}$ cm$^{-1}$) | Absorbance Onset (nm) | Emission Spectral Range | Quantum Yield for Fluorescence | Fluorescence Lifetime (ns) |
|---|---|---|---|---|---|---|
| 2% Tinopal-on-Syloid | 1.5 × 10$^7$ | 1,000 | <420 | 380-575 | 0.81 | 1.2 |
| Free NADH (protein-bound NADH) | 4.8 × 10$^6$ | 6,220 | <410 | 390-510 | 0.020 (0.08) | 0.38, 0.74 (1.2) |
| Riboflavin | 2 × 10$^6$ | 15,000 | <500 | 480-610 | 0.3 | 4.1 | be selected as needed to optimize the photon-blocking function of the plate 462. The aperture 464 may be generally centered on the longitudinal axis 132. In some embodiments, the aperture 464 should be large enough that it does not act as a gas conductance barrier, cause localized turbulence, or otherwise appreciably modify the dynamics of the sample fluid flow through the detection cavity 104. More than one plate 462 may be provided if desired. Moreover, the plate 462 may include more than one aperture 464. In other embodiments, the beam 108 of irradiation light is sufficiently coherent and/or collimated that the plate 462 or similar device is not needed.

In some embodiments the housing 120, or at least the portion of the housing 120 defining the detection cavity 104, may be composed of a low reflectance material, or at least the inside surface of the housing 120 (or a coating applied thereon) may be composed of a low reflectance (or opaque, or anti-reflective) material. This may be useful in preventing stray light from reaching the light detector 128.

Figure 5:
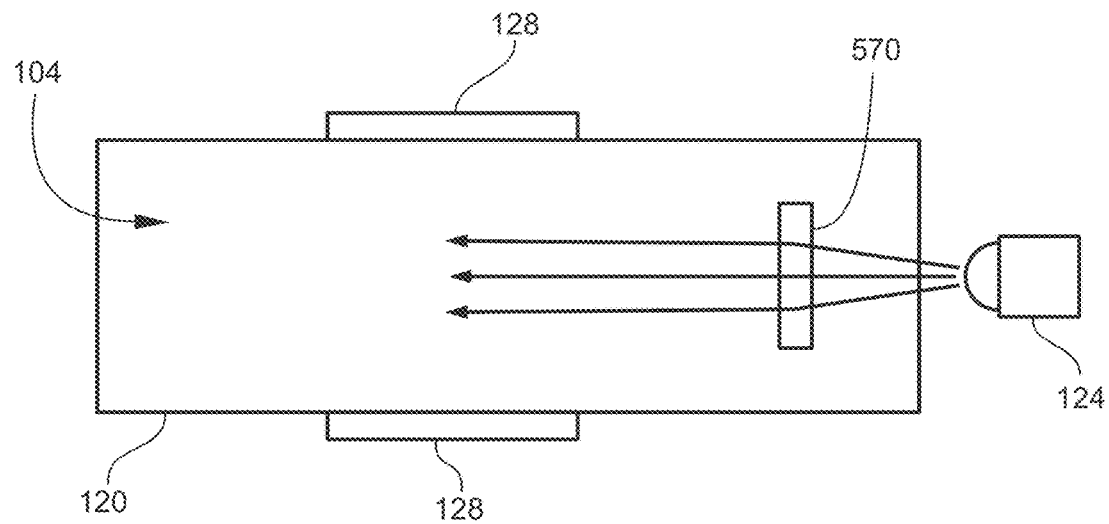
FIG. 5 is a schematic plan view of the particle detector illustrated in FIG. 1, illustrating an example of beam shaping optics that may be utilized in the particle detector.

In some embodiments, if needed or desired, the particle detector 100 may include beam shaping optics. The beam shaping optics may include one or more optics components (e.g., lenses). In the present context, the term "beam shaping optics" refers to an optical component that modifies a light beam or beam path without filtering out wavelengths. FIG. 5 schematically illustrates an example of beam shaping optics 570. As one example, the beam shaping optics 570 may be or include a collimator (collimating lens) for collimating the beam of irradiation light. Such beam shaping optics 570 may be provided alternatively or in addition to the plate 462 or other stray light blocking device described above and illustrated in FIG. 4. The axial position of the beam shaping optics 570 relative to the light source 124 may be selected as needed to optimize its beam shaping function. In other embodiments, the beam shaping optics 570 may be integrated into the package or assembly of the light source 124. In other embodiments, the beam 108 of irradiation light generated by the light source 124 is sufficiently coherent and/or collimated that a collimator separate and distinct from the light source 124 is not needed. As another example, in addition or as an alternative to a collimator, the beam shaping optics 570 may be or include a beam expander configured for increasing the diameter of the beam 108 emitted from the light source 124.

Referring to FIG. 1, the light detector 128 is configured for collecting measurement light over a large detection area (i.e., a large photon collection area) via a plurality of paths 116 over which the measurement light propagates, including measurement light paths angled relative to the longitudinal axis 132 as described above. To this end, the light detector 128 may include a large-area active photo-responsive or photo-sensitive material (e.g., a photovoltaic material, photoelectric material, photoconductive material, photoresistive material, etc.). The light detector 128 also includes one or more anodes and cathodes communicating with the active material as appreciated by persons skilled in the art. The light detector 128, or at least the photo-responsive material, surrounds the detection cavity 104 along at least a portion of the cavity length. In the illustrated embodiment, the light detector 128 or at least the photo-responsive material is constructed from a flexible material (one or more layers of flexible material(s)), enabling it either to be conformally wrapped around an outside surface of the housing 120 (or a portion of the housing 120 defining the detection cavity 104) or to conformally line an inside surface of the housing 120. In a typical embodiment, the photo-responsive material is relatively thin so as to render it flexible (e.g., on the order of millimeters or smaller). The photo-responsive material may be composed of any material (or composite of two or more materials) exhibiting efficient photo-responsive (e.g., photovoltaic activity, photoelectric activity, etc.) and sufficiently sensitive over the range of wavelengths of measurement light contemplated for the particle detector 100. For example, the photo-responsive material may be a thin-film inorganic, organic, or hybrid organic/inorganic semiconductor, one non-limiting example being amorphous silicon. The photo-responsive material may generally be a material having at least one electrical characteristic (current, voltage, or resistance) that varies in proportion to light incident thereon.

In some embodiments, the photo-responsive material is a photovoltaic (PV) material that produces both a current response and a voltage response to photons incident on its surface. For low light conditions, both a current response and voltage response are observed and are proportional to the amount of photons striking the PV material. The open-circuit voltage (OCV) of a PV material may show a measurable response to low-level particulate concentration changes (e.g., less than 100 #/cm$^3$), due to the logarithmic response relationship between increases in low-level incident light ($<<0.1$ Suns; or the amount of incident photons corresponding to elastic scattering from particles or fluorescence emissions) and the resulting increase in OCV. In other cases, such as high particle concentrations, measurement of the current response of the PV material may be more useful. In some embodiments, the PV material may a solar cell, which may be a commercially available solar cell.

In a typical embodiment, at least one side of the photo-responsive material is supported by a flexible substrate (e.g., a polymer layer or film such as polyimide). In some embodiments the photo-responsive material may be completely encapsulated by (or embedded in) the substrate, or sandwiched between the substrate and an additional encapsulating layer or film, to protect the photo-responsive material from the operating environment. Any layer or film covering the photon collecting side of the photo-responsive material should be optically transparent. In some embodiments, the photon collecting side may be covered by a transparent electrode. In some embodiments, the photon collecting side may be covered by a layer or film of an optical filter material, examples of which are described below.

The photo-responsive material may completely or substantially completely surround the detection cavity 104 to provide a detection area spanning 360° or nearly 360° around the longitudinal axis 132. The photo-responsive material may contiguously surround the detection cavity 104. Alternatively, the photo-responsive material may include a plurality of discrete units or cells of photo-responsive material spaced apart from each other and collectively surrounding the detection cavity 104.

Figure 6:
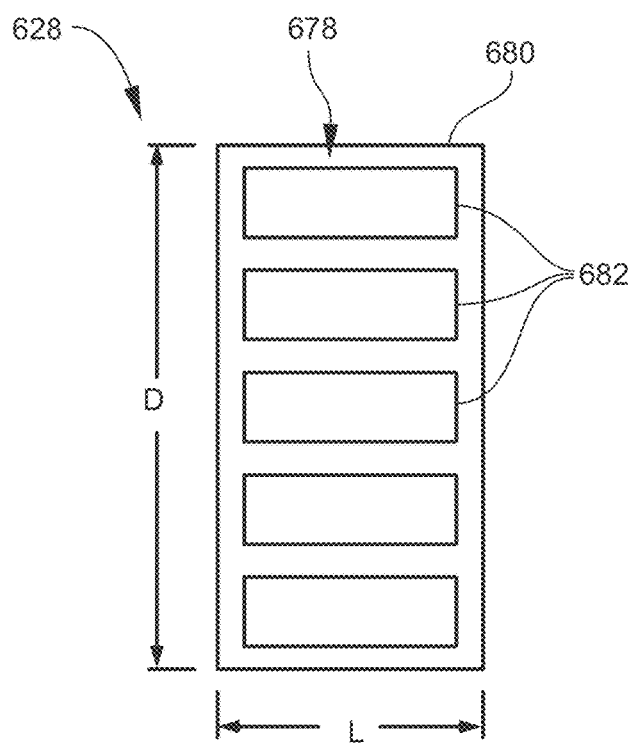
FIG. 6 is a schematic plan view of an example of a flexible light detector that may be utilized in particle detectors disclosed herein.

FIG. 6 is a schematic plan view of an example of a flexible light detector 628 that may be utilized in the particle detector 100. The light detector 628 may generally include a flexible photo-responsive material 678 disposed on a flexible substrate 680. In this example, the photo-responsive material 678 includes a plurality of photo-responsive materials, or photo-responsive units or cells 682 (which may also be referred to light detector units or cells, and which in some embodiments may be photovoltaic (PV) units or cells such as solar cells). The photo-responsive units 682 are spaced apart from each other, but may be closely grouped so as to maximize the size of the active detection area. While in the illustrated example the photo-responsive units 682 are arranged in a one-dimensional array, in other embodiments they may be arranged in a two-dimensional array. The light detector 628 may initially be provided as a planar strip, and thereafter manipulated so as to surround the detection cavity 104. For example, the light detector 628 may be conformally mounted to the housing 120 as noted above. Thus, in the case of a cylindrical or spherical housing, the light detector 628 may surround the detection cavity 104 as a cylinder, band, or ring. The light detector 628 may present a significant surface area (L×D) largely occupied by the active material of the photo-responsive units 682. As one non-limiting example, the dimension L may be on the order of one or more tens of millimeters, and the dimension D may be on the order of tens to hundreds of millimeters. When applied to a cylindrical or spherical housing, the dimensions L and D respectively correspond to a cylinder length and diameter of the light detector 628. The light detector 628 may include various current-carrying components (interconnects, wires, contacts, and the like, not shown) as appreciated by persons skilled in the art. In one non-limiting example, the light detector 628 may be based on a PV module commercially available from PowerFilm, Inc., Ames, Iowa, USA (e.g., model MP3-37).

In all such embodiments, the photo-responsive material 678 provides a very large number of detection points surrounding the detection cavity 104 on which photons of the measurement light may be incident and thereby detected and measured. These detection points may be located at different angular positions relative to the central axis (over dimension D in FIG. 6) and/or different axial positions relative to the longitudinal axis (over dimension L in FIG. 6). As evident from FIGS. 2 and 3, the photo-responsive material 678 provides a target for measurement light propagating over many different paths from an irradiated particle. By this configuration, the light detector 628 is able to output an electrical detector signal of relatively high intensity measurement even though individual optical measurement signals emanating from the particles may be relatively weak.

Referring to FIG. 1, in some embodiments the particle detector 100 further includes one or more optical filters 186 positioned optically between the photon collecting side of the photo-responsive material of the light detector 128 and the longitudinal axis 132. That is, the optical filter 186 is positioned such that any measurement light directed toward the photo-responsive material must first pass through the optical filter 186. In some embodiments, the optical filter 186 is disposed on the photo-responsive material, i.e., directly on the photo-responsive material or on a layer or film covering or encapsulating the photo-responsive material. The optical filter 186 generally may be configured to block one or more ranges of wavelengths, and thus may be a low-pass, high-pass, or band-pass filter. The optical filter 186 may be a composite of two or more optical filters to obtain the desired pass/block characteristics. The optical filter 186 may be a solid (e.g. glass or polymer) or gel (e.g. polymer) material, and may be thin and/or pliable enough to be flexible so as to conformally cover the photo-responsive material. In one non-limiting example, a gel filter may be one commercially available from Rosco Laboratories, Inc., Stamford, Conn., USA.

The cross-sectional view of FIG. 2 illustrates some examples of possible arrangements of the photo-responsive material and optical filter relative to the housing. At the region of the detection cavity 104 where the photo-responsive material and optical filter are located, the particle detector 100 may be considered as including at least three layers surrounding the detection cavity: a first (inner) layer 202, a second (intermediate) layer 206 surrounding the first layer 202, and a third (outer) layer 210 surrounding the second layer 206. In one embodiment, the first layer 202 is the optical filter, the second layer 206 is the housing (i.e., a wall of the housing), and the third layer 210 is the photo-responsive material. Thus in this embodiment, the optical filter is conformally disposed on the inside surface of the housing, and the photo-responsive material is conformally disposed on the outside surface of the housing. In another embodiment, the first layer 202 is the optical filter, the second layer 206 is the photo-responsive material, and the third layer 210 is the housing. Thus in this embodiment, the photo-responsive material is conformally disposed on the inside surface of the housing, and the optical filter is conformally disposed on the photo-responsive material, such that the photo-responsive material is sandwiched between the housing and the optical filter. In yet another embodiment, the first layer 202 is the housing, the second layer 206 is the optical filter, and the third layer 210 is the photo-responsive material. Thus in this embodiment, the optical filter is conformally disposed on the outside surface of the housing, and the photo-responsive material is conformally disposed on the optical filter, such that the optical filter is sandwiched between the photo-responsive material and the housing. In cases where the photo-responsive material is outside the housing, the housing (or at least the portion coextensive with the photo-responsive material) is optically transparent. If needed, the layers 202, 206, and 210 may be secured to each other by any suitable means such as adhesives, mechanical fasteners, etc. In embodiments without the optical filter, the photo-responsive material may be conformally disposed directly on the inside surface or outside surface of the housing.

The optical filter may generally be configured for blocking any selected wavelength or range(s) of wavelengths (undesired photons), depending on the application. For example, when measuring autofluorescence, the optical filter may be configured for passing the wavelengths of the fluorescent measurement light while blocking the wavelength of the irradiating light utilized to excite the fluorophores. As another example, when measuring scattering, the optical filter may be configured for passing the wavelength of the irradiating light (and thus the wavelength of the scattered measurement light) while blocking other wavelengths such as, for example, stray ambient light.

Referring to FIG. 1, in some embodiments the particle detector 100 may further include a data acquisition device 190 that may be placed in signal communication with the light detector 128. The data acquisition device 190 may be configured for measuring a response of the photo-responsive material (e.g., a voltage response, a current response, and/or resistance response), as embodied in an electrical detector signal outputted by the photo-responsive material. The data acquisition device 190 may be configured for converting the analog detector signal to a digital detector signal, and recording or storing the detector signal. The data acquisition device 190 may be configured for correlating the measurement of the response with one or more properties of the particles interrogated by the irradiation light in the detection cavity 104, such as particle size, concentration, identification (e.g., a certain type of bio-particle), etc. The data acquisition device 190 may be configured for performing any post-acquisition signal conditioning or processing required or desired, such as amplification, calibration, deconvolution, formatting for transmission to another device, etc. The data acquisition device 190 may be configured for generating data relating to one or more properties of the interrogated particles, and transmitting the data to another device (e.g., a computing device) via a wired or wireless communication link, or to one or more devices via a suitable communication network. The data acquisition device 190 may be removably coupled to the light detector 124 such as by removable connections made with electrical leads from the photo-responsive material. The data acquisition device 190 may thereafter be coupled to another device to download data to that other device for analysis. As appreciated by persons skilled in the art, various functions of the data acquisition device 190 may be implemented by hardware (or firmware), software, or both. The data acquisition device 190 may include one or more processors, memories, and other hardware. In one non-limiting example, the data acquisition device 190 may be a 16-bit data logging device commercially available from Measurement Computing Corp., Norton, Mass., USA (e.g., model USB-1698FS-Plus).

Figure 7:
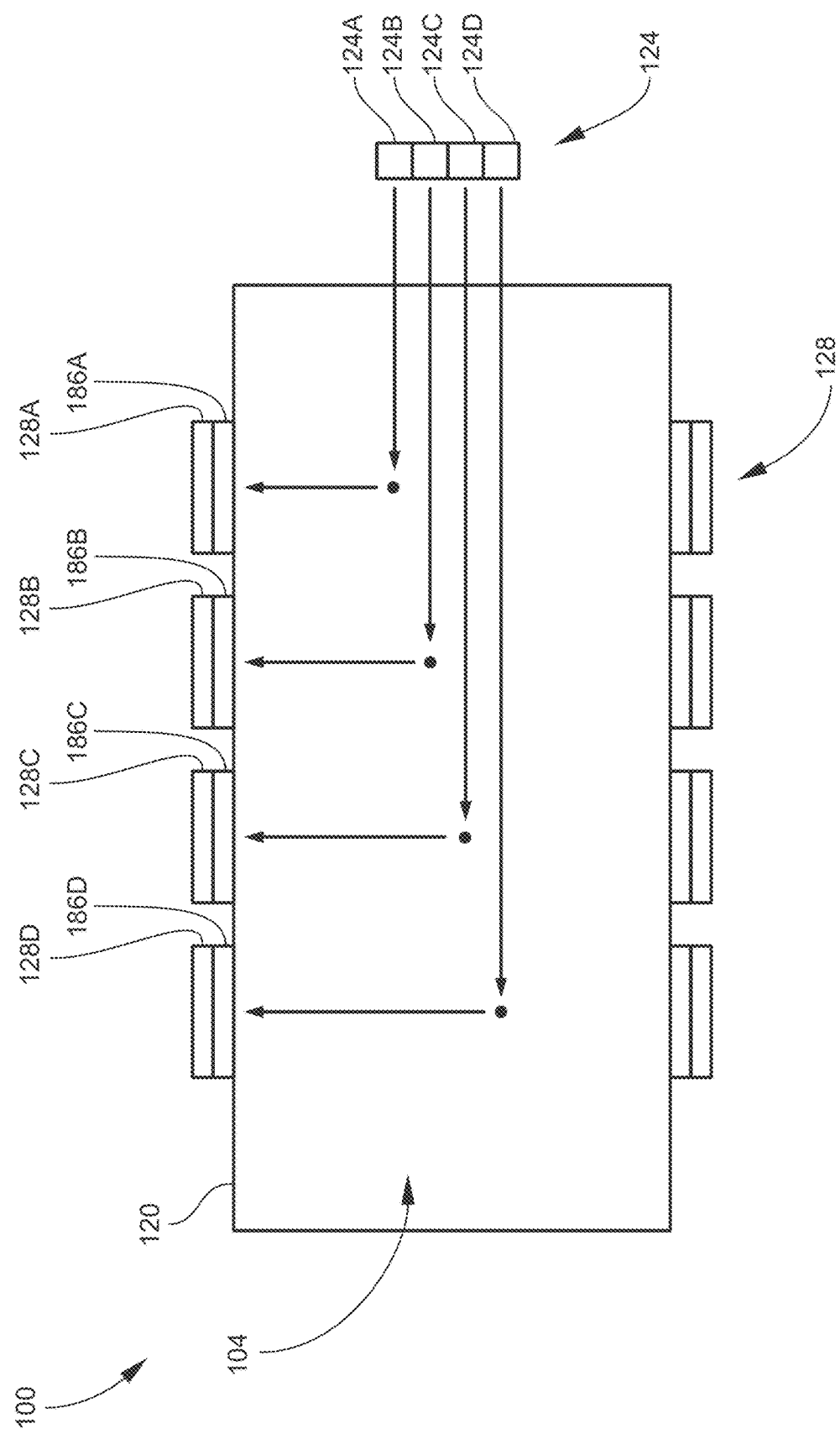
FIG. 7 is a schematic cross-sectional view of the particle detector according to other embodiments.

FIG. 7 is a schematic cross-sectional view of the particle detector 100 according to other embodiments. The light source 124 may include a plurality of separate light sources (or light source units) 124A, 124B, 124C, and 124D. Four light sources 124A, 124B, 124C, and 124D are illustrated by example only, as more than or less than four may be provided. In some embodiments, the light sources 124A, 124B, 124C, and 124D may be arranged in a closely grouped bundle centered on the longitudinal axis 132. In some embodiments, two or more of the light sources 124A, 124B, 124C, and 124D may emit irradiating light at the same wavelength, which may be useful for boosting the measurement signal and/or increasing the overall size of the particle irradiation region within the detection cavity 104. In some embodiments, at least one of the light sources 124A, 124B, 124C, and 124D may emit irradiating light at a wavelength different from that of the other light sources 124A, 124B, 124C, and 124D. For example, one or more light sources 124A, 124B, 124C, and 124D may emit irradiating light at a first wavelength selected for measuring scattered radiation, while one or more other light sources 124A, 124B, 124C, and 124D may emit irradiating light at a second, different wavelength selected for measuring scattered radiation. As another example, one or more light sources 124A, 124B, 124C, and 124D may emit irradiating light at a first wavelength selected for measuring fluorescent radiation from a first type of particle, while one or more other light sources 124A, 124B, 124C, and 124D may emit irradiating light at a second, different wavelength selected for measuring fluorescent radiation from a second type of particle. The latter configuration may be useful, for example, for detecting one or more types of particles in the sample fluid. As another example, one or more light sources 124A, 124B, 124C, and 124D may emit irradiating light at a first wavelength (or two or more different first wavelengths) selected for measuring scattered radiation, while one or more other light sources 124A, 124B, 124C, and 124D may emit irradiating light at a second, different wavelength (or two or more different second wavelengths) selected for measuring fluorescent radiation.

In some embodiments entailing the use of two or more different irradiation wavelengths, the different light sources 124A, 124B, 124C, and 124D may be operated sequentially according to any desired pulse sequence. For example, the particle detector 100 may alternate the operation of two different light sources 124A, 124B, 124C, and 124D one or more times to alternately measure scattered radiation and fluorescent radiation. As another example, the particle detector 100 may cycle through the operation of two or more different light sources 124A, 124B, 124C, and 124D one or more times to measure scattered radiation at two or more different wavelengths and/or measure fluorescent radiation at two or more different wavelengths.

As also illustrated in FIG. 7, in some embodiments the light detector 128 may include a plurality of separate light detectors (or light detector units) 128A, 128B, 124C, and 128D. Each light detector 128A, 128B, 124C, and 128D includes a photo-responsive material, which may comprise a plurality of photo-responsive units as described above and illustrated in FIG. 6, and associated components. Four light detectors 128A, 128B, 124C, and 128D are illustrated by example only, as more than or less than four may be provided. The number of light detectors 128A, 128B, 124C, and 128D may be the same as, less than, or more than the number of light sources 124A, 124B, 124C, and 124D. One or more of the light detectors 128A, 128B, 124C, and 128D may be optically aligned with respective optical filters 186A, 186B, 186C, and 186D.

Providing two or more light detectors 128A, 128B, 124C, and 128D may be done to increase the active detection area of the light detector 128, and to increase the number and angular range of forward-angle paths 344 and back-angle paths 346 (FIG. 3) in the line of sight of the active detection area. Alternatively or additionally, providing two or more light detectors 128A, 128B, 124C, and 128D may be done to increase detector signal intensity. In some embodiments, two or more light detectors 128A, 128B, 124C, and 128D may be electrically coupled in series with each other to increase voltage response, and/or two or more light detectors 128A, 128B, 124C, and 128D may be electrically coupled in parallel with each other to increase current response.

Alternatively or additionally, providing two or more light detectors 128A, 128B, 124C, and 128D may be done to provide two or more distinct wavelength (or distinct wavelength range) collection abilities and/or to produce two or more distinct detector output signals. In such embodiments, two or more light detectors 128A, 128B, 124C, and 128D may be electrically isolated from each other, and thus operate independently from each other. For example, this may be done so that the same particle detector 100 may be utilized for both scattering- and fluorescence-based analyses, and/or for scattering-based analyses implemented at two or more different irradiation wavelengths, and/or for fluorescence-based analyses implemented at two or more different irradiation (excitation) wavelengths or two or more different measurement wavelengths (or wavelength ranges). Thus in some embodiments, at least one of the light detectors 128A, 128B, 124C, and 128D may be sensitive to a wavelength (or range of wavelengths) different from the other light detectors 128A, 128B, 124C, and 128D. Alternatively, at least one of the light detectors 128A, 128B, 124C, and 128D may be optically aligned with an optical filter 186A, 186B, 186C that passes to that light detector a wavelength (or range of wavelengths) different from the wavelengths received by the other light detectors 128A, 128B, 124C, and 128D. In one specific example, a light detector intended to receive scattered radiation may include an optical filter that blocks other wavelengths associated with fluorescent radiation, while another light detector intended to receive fluorescent radiation include an optical filter that blocks the wavelength associated with the irradiating light (and thus scattered radiation). In the illustrated example, light detector 128A is configured to collect measurement light scattered or emitted from particles irradiated by light source 124A, light detector 128B is configured to collect measurement light scattered or emitted from particles irradiated by light source 124B, light detector 128C is configured to collect measurement light scattered or emitted from particles irradiated by light source 124C, and light detector 128D is configured to collect measurement light scattered or emitted from particles irradiated by light source 124D.

Generally, the particle properties, attributes of the irradiating light, and signal response of the light detector with respect to wavelength may all influence the LOD and sensitivity of the particle detector 100. Detection of particle type, sensitivity, and LOD may all be tuned (optimized) via appropriate selection of optical filter(s), the wavelength, intensity and collimation of the irradiating light, and the response characteristics of the light detector(s).

Figure 8:
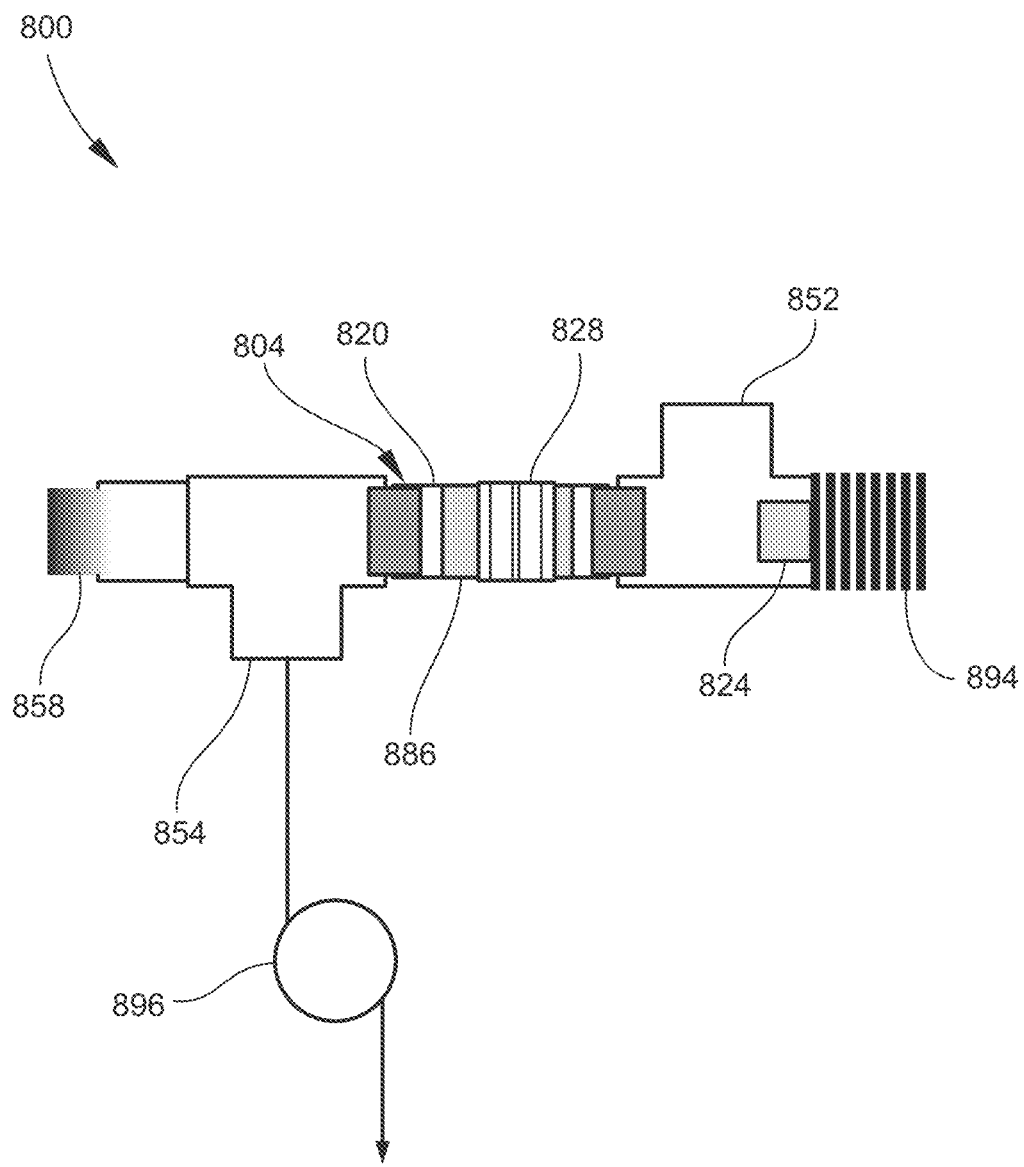
FIG. 8 is a schematic plan view of an example of a particle detector according to another embodiment.

FIG. 8 is a schematic plan view of another example of a particle detector 800 according to some embodiments. The particle detector 800 may include a housing 820 defining a flow-through detection cavity 804, one or more light sources 824, and one or more light detectors 828. In the illustrated embodiment, the housing 820 and thus the detection cavity 804 are generally cylindrical and elongated along the longitudinal axis. The particle detector 800 may also include a light trap 858 and one or more optical filters 886 as described above, as well as one or more other features described above and illustrated in FIGS. 1 to 7. In some embodiments, the light detector(s) 828 and optical filter(s) 886 may include flexible materials as described above. In the present embodiment, the light source 824 includes a heat sink 894, which may provide cooling fins or other means for increasing surface area available for heat transfer with ambient air. The housing 820 includes a sample inlet 852 and a sample outlet 854 positioned such that the housing 820 defines a sample flow path from the sample inlet 852, through the detection cavity 804, and to the sample outlet 854. In the present embodiment, the housing 820 is configured such that the sample inlet 852, the sample outlet 854, or both (as illustrated) are oriented at an angle to the longitudinal axis (ninety degrees in the illustrated example). This configuration minimizes the amount of ambient light entering the detection cavity 804 and reaching the light detector(s) 828.

As also shown in FIG. 8, the particle detector 800 may include a fluid moving device 896 (e.g., pump, fan, blower, etc.) configured for moving sample fluid through the sample flow path. Generally, the fluid moving device 896 communicates with the detection cavity 804. For this purpose, the fluid moving device 896 may be positioned downstream of the detection cavity 804. The fluid moving device 896 may be positioned downstream of the sample outlet 854 and outside the housing 820 (as illustrated), or may be positioned inside the housing 820. Generally, the fluid moving device 896 should be positioned so as not to create turbulence in the detection cavity 804. The fluid moving device 896 may be configured for moving the sample fluid through the detection cavity 804 under laminar flow conditions and in a smooth, pulse-free manner. Maintaining the laminar flow regime may minimize internal particle losses and improve the sensitivity and accuracy of the data acquired. In some embodiments, the fluid moving device 896 is configured for moving the sample fluid through the detection cavity 804 at a flow rate on the order of liters per minute. In some embodiments, the fluid moving device 896 is configured such that the flow rate is adjustable by a user. It will be understood that the fluid moving device 896 is optional. Ambient fluid flow conditions may be sufficient for operating the particle detector 800 without the use of the fluid moving device 896.

As also shown in FIG. 8, the particle detector 800 may have a modular configuration in which one or more housing portions and/or components of the particle detector 800 may be removable from other housing portions or components (e.g., light source(s) 824, light trap 858, fluid moving device 896) for cleaning, maintenance, or replacement. Light source(s) 824 may also be removable to enable a user to select different irradiation wavelengths. Light detector(s) 828 and optical filter(s) 886, or the housing portion on which the light detector(s) 828 and optical filter(s) 886 are attached, may be removable to enable a user to select different light detectors 828 and optical filters 886 or combinations thereof. Moreover, the modularity may enable the user to add different housing portions in series to configure the particle detector 800 in a manner similar to that shown in FIG. 7. The multiple housing portions may include the same or different combinations of one or more light detectors 828 and one or more optical filters 886 pre-attached to the housing portions.

In some embodiments, the particle detector 800 may be provided to the user in the form of a kit in which the particle detector 800 is fully or partially disassembled. For example, the kit may include a plurality of different light sources 824, light detectors 828, and/or optical filters 886. Alternatively or additionally, the kit may include a plurality of different housing portions defining the detection cavity 804. The housing portions may include different combinations of one or more light detectors 828 and one or more optical filters 886 pre-attached to the housing portions, thereby enabling the user to tailor the analytical functions of the particle detector 800 as desired.

Figure 9:
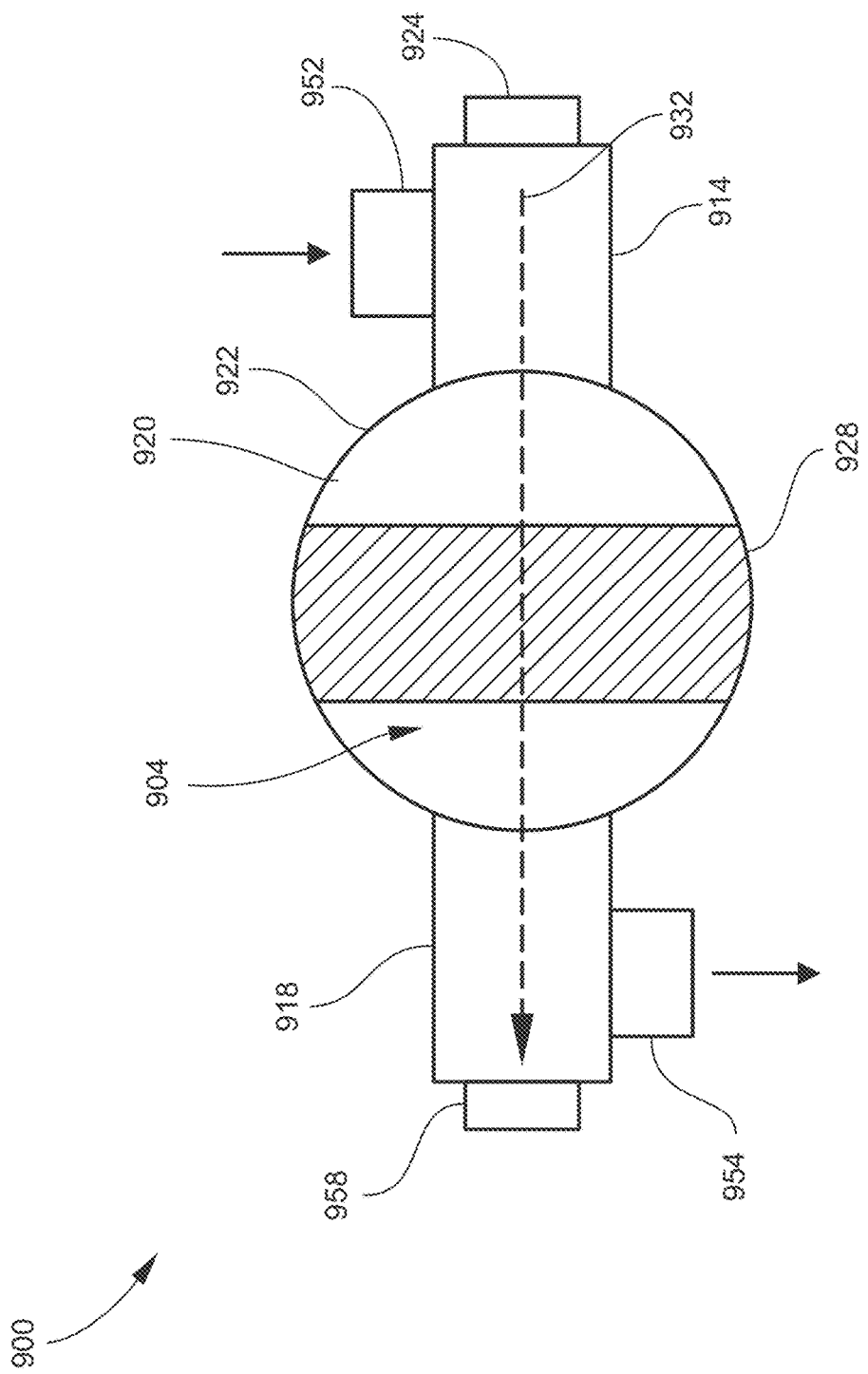
FIG. 9 is a schematic plan view of an example of a particle detector according to another embodiment.

FIG. 9 is a schematic plan view of another example of a particle detector 900 according to some embodiments. The particle detector 900 may include a housing 920 defining a flow-through detection cavity 904, one or more light sources 924, and one or more light detectors 928. The particle detector 900 may also include a light trap 958 and one or more optical filters (not shown) as described above, as well as one or more other features described above and illustrated in FIGS. 1 to 8. In some embodiments, the light detector(s) 928 and optical filter(s) may include flexible materials as described above. The housing 920 includes a sample inlet 952 and a sample outlet 954 positioned such that the housing 920 defines a sample flow path from the sample inlet 952, through the detection cavity 904, and to the sample outlet 954. The light source 924, sample inlet 952, sample outlet 954, and light trap 958 may be positioned such that the irradiating light propagates and sample fluid flows generally collinearly along a longitudinal axis 932. The particle detector 900 may be configured similarly to the particle detector 800 described above and illustrated in FIG. 8. However, the particle detector 900 includes one or more sections in which the size of the cross-section (cross-sectional area) of the detection cavity 904 varies along the longitudinal axis 932. In the illustrated embodiment, this is implemented by the housing 920 and thus the detection cavity 904 being spherical or including a spherical section 922. In this case, the longitudinal axis 932 may be an axis of symmetry of the spherical section 922.

Also in the illustrated embodiment, the housing 920 may include an axial inlet section 914 and an axial outlet section 918 of rounded or polygonal cross-section, extending from the spherical section 922 along the longitudinal axis 932. As illustrated, the light source 924 and sample inlet 952 may be positioned at the inlet section 914 and the sample outlet 954 and the light trap 958 may be positioned at the outlet section 918. The light detector 928 may be wrapped around the detection cavity 904 in an orientation ninety degrees to the longitudinal axis 932, or may be oriented at a different angle.

Additional light detectors (not shown) may be wrapped fully or partially around the detection cavity 904 to provide additional areas for active detection.

Figure 10:
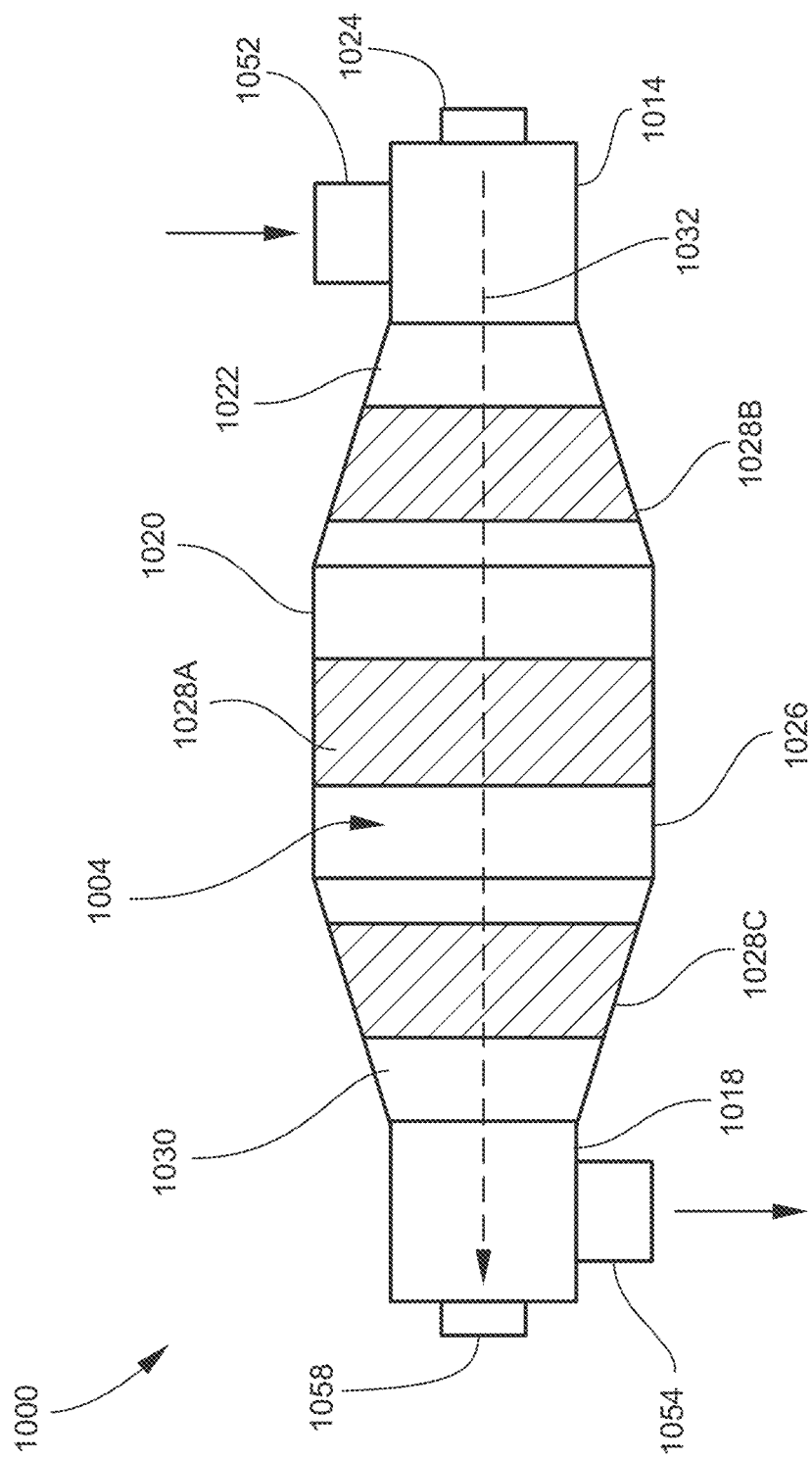
FIG. 10 is a schematic plan view of an example of a particle detector according to another embodiment.

FIG. 10 is a schematic plan view of another example of a particle detector 1000 according to some embodiments. The particle detector 1000 may include a housing 1020 defining a flow-through detection cavity 1004, one or more light sources 1024, and one or more light detectors 1028A, 1028B, and 1028C. The particle detector 1000 may also include a light trap 1058 and one or more optical filters (not shown) as described above, as well as one or more other features described above and illustrated in FIGS. 1 to 9. In some embodiments, the light detector(s) 1028A, 1028B, and 1028C and optical filter(s) may include flexible materials as described above. The cross-sections of the housing 1020 and detection cavity 1004 may be rounded or polygonal. The housing 1020 includes a sample inlet 1052 and a sample outlet 1054 positioned such that the housing 1020 defines a sample flow path from the sample inlet 1052, through the detection cavity 1004, and to the sample outlet 1054. The light source 1024, sample inlet 1052, sample outlet 1054, and light trap 1058 may be positioned such that the irradiating light propagates and sample fluid flows generally collinearly along a longitudinal axis 1032, which may be an axis of symmetry of the detection cavity 1004 and one or more other portions of the particle detector 1000. The particle detector 1000 may be configured similarly to the particle detector 800 described above and illustrated in FIG. 8 or 9. However, the particle detector 1000 includes one or more sections in which the size of the cross-section (cross-sectional area) of the detection cavity 1004 varies along the longitudinal axis 1032. This may be implemented, for example, by the housing 1020 including one or more transitions, or tapered sections, in which the cross-section increases or decreases. Such transitions or tapered sections may have, for example, a truncated conical or pyramidal configuration. In the illustrated embodiment, the housing 1020 includes an increasing transition 1022 (i.e., the cross-section increases in the direction of fluid flow and irradiating light propagation) adjoined to a section 1026 of constant cross-section, which in turn is adjoined to a decreasing transition 1030.

In another embodiment, the transition 1022 may be a decreasing transition instead of an increasing transition, whereby the cross-section decreases in the direction of fluid flow such that the flow is focused into a smaller cross-section in the section 1026 of constant cross-section. More generally, the determination as to whether to include cross-sectional transitions, and whether such transitions should expand or converge the cross-section in the direction of fluid flow, may depend on a variety of factors related to fluid mechanics, distance between particles and particle detector, etc.

Also in the illustrated embodiment, the housing 1020 may include an axial inlet section 1014 extending from the increasing transition 1022, and an axial outlet section 1018 extending from the decreasing transition 1030 along the longitudinal axis 1032. As illustrated, the light source 1024 and sample inlet 1052 may be positioned at the inlet section 1014 and the sample outlet 1054 and the light trap 1058 may be positioned at the outlet section 1018. One or more light detectors 1028A may be wrapped around the detection cavity 1004 at the section 1026 of constant cross-section, in an orientation ninety degrees to the longitudinal axis 1032. Additionally or alternatively, one or more light detectors 1028B and/or 1028C may be wrapped around the increasing transition 1022 and/or the decreasing transition 1030, respectively.

Figure 11:
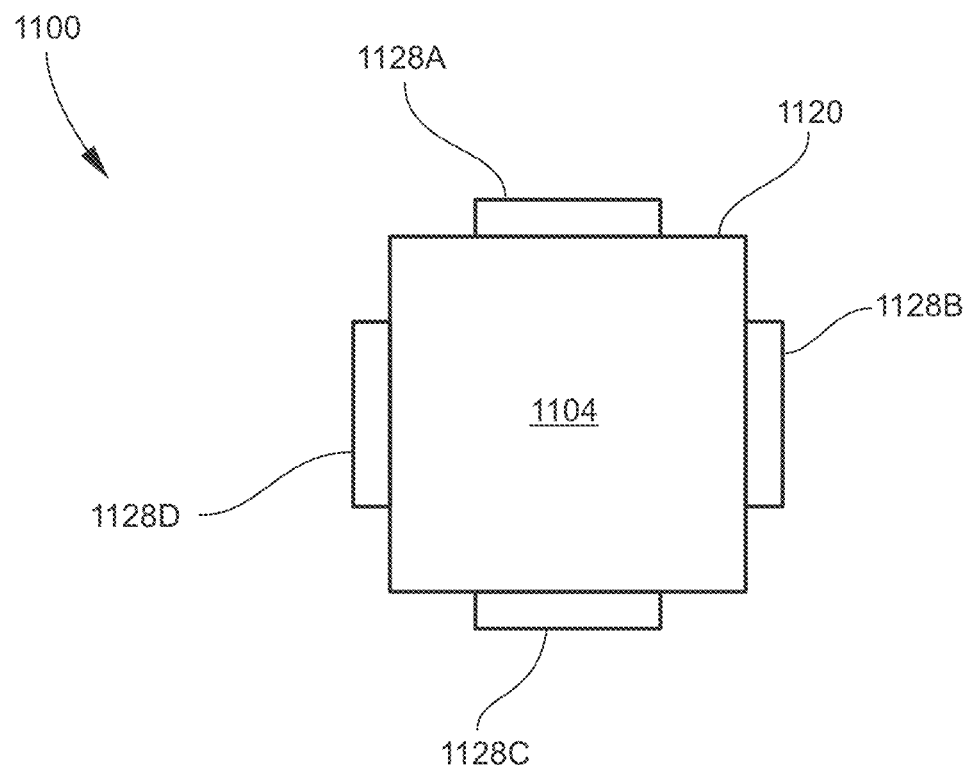
FIG. 11 is a schematic cross-sectional end view of an example of a particle detector according to another embodiment.

FIG. 11 is a schematic cross-sectional end view of another example of a particle detector 1100 according to some embodiments. The view is taken through a detection cavity 1104 defined by a housing 1120 of the particle detector 1100. In this embodiment, the housing 1120 includes a plurality of flat wall sections whereby the cross-section of the detection cavity 1104 is polygonal. FIG. 11 illustrates a rectilinear cross-section by example only, as other polygonal geometries (e.g., hexagon, octagon, etc.) may be implemented as well. One or more light detectors 1128A, 1128B, 1128C, and 1128D may be positioned at respective flat wall sections. In other embodiments, a lesser number of opposing pairs of light detectors may be provided for a given polygonal geometry. In FIG. 11, for example, just one opposing pair of light detectors (1128A and 1128C, or 1128B and 1128D) may be provided.

EXAMPLE 1—General Aerosol Detection

In this Example, a particle detector having a configuration similar to that illustrated in FIG. 8 was fabricated. The housing was an optically clear tube that was 1.62 inches (41.1 mm) in diameter. A flexible PV detector sized at 1.5 inches by 4.5 inches (MP3-37 by Power Film Solar) was selected as the light detector. The flexible PV detector was wrapped around the clear tube. A red laser diode of 650 nm wavelength was selected as the light source, and positioned to shine down the center of the tube with air flowing coaxial with the light at a flow rate of 5 liters per minute. A light trap was positioned at the opposite end of the tube. A test system was constructed to evaluate the particle detector. The test system was made up of mostly black polyvinylchloride (PVC) pipe that was 1½ inches in diameter. The output voltage of the PV detector was measured in real time at 1 sample per second using a 16 Bit DataLogger (Measurement Computing USB-1698FS-Plus).

The particle detector was connected to an aerosol mixing chamber that supplied a controlled and well mixed concentration of aerosol. An Aerodynamic Particle Sizer (APS; TSI Incorporated) was placed after (downstream of) the particle detector. The APS provided the air flow (5 L/min) through the particle detector and provided size and count information about the aerosol passing through the instruments. This arrangement of the sampled air flowing through both instruments provided identical aerosol concentrations to both instruments. The aerosol concentration information from the APS was used as a standard or reference. In addition to the APS, a Condensation Particle Counter model 3022a (CPC; TSI Incorporated) was also connected to the aerosol mixing chamber but not in the same sampling flow path as the particle detector and APS. However, given the well mixed environment of the aerosol chamber, very similar concentrations were expected to be measured by all instruments. Using the combination of the two particle counters provided better insight into how well the particle detector performed. The APS measures particle size and concentration ranging from approximately 0.5 μm (500 nm) to over 5 μm. The CPC model 3022a has a lower size range of 7 nm, and an upper range of approximately 1 μm. Used by itself the CPC provides only total count information. Adding a Scanning Mobility Particle Sizer (SMPS; TSI Incorporated) provided size information. Both of the APS and CPC instruments are precision particle counters.

Figure 12:
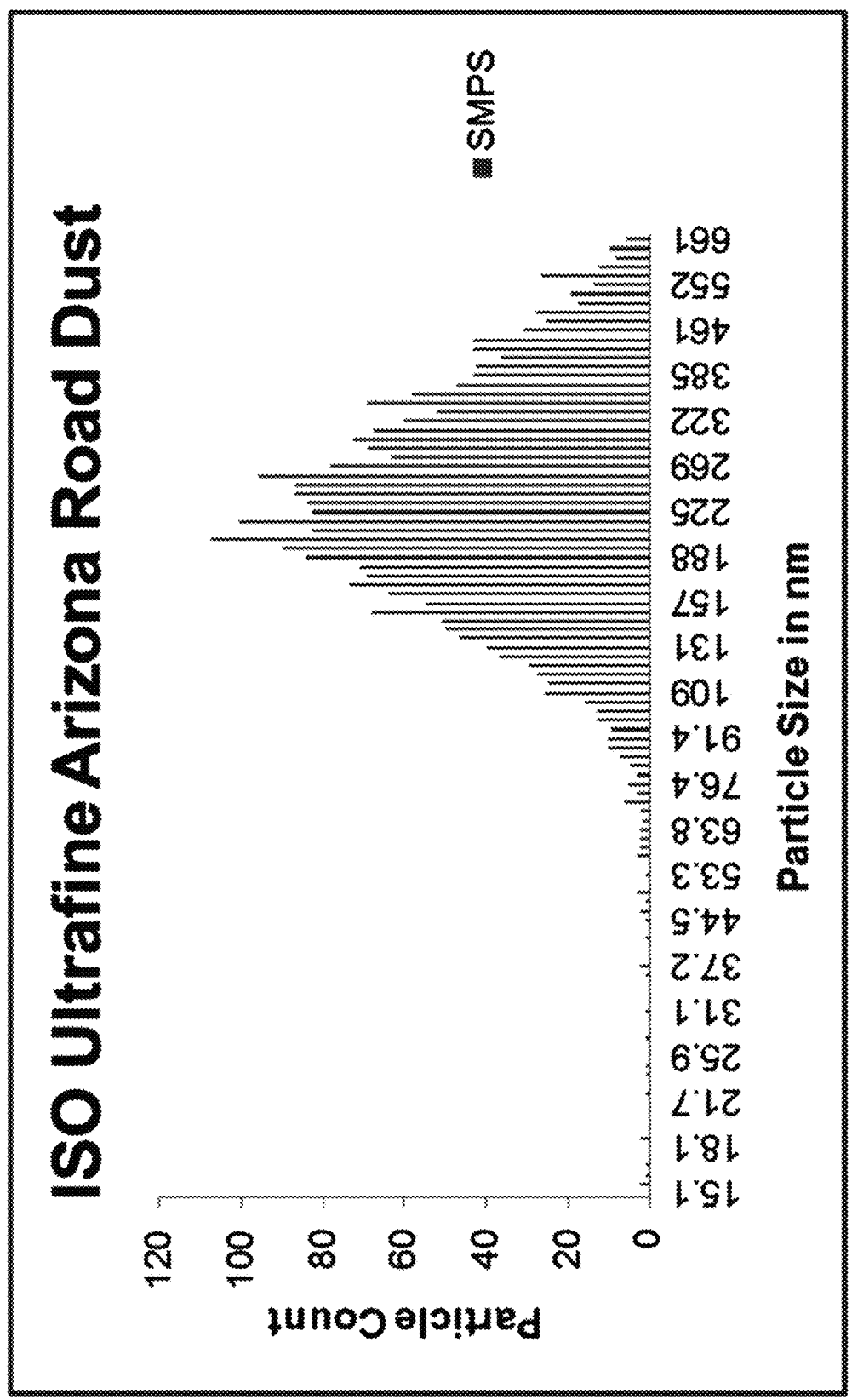
FIG. 12 is a plot of size distribution of ISO Ultrafine Arizona Road Dust as measured with a Scanning Mobility Particle Sizer (SMPS) and sampled by a particle detector as described below in Example 1; the Dust was dispersed into an aerosol mixing chamber and then sampled with the SMPS connected to a Condensation Particle Counter (CPC).
Figure 13A:
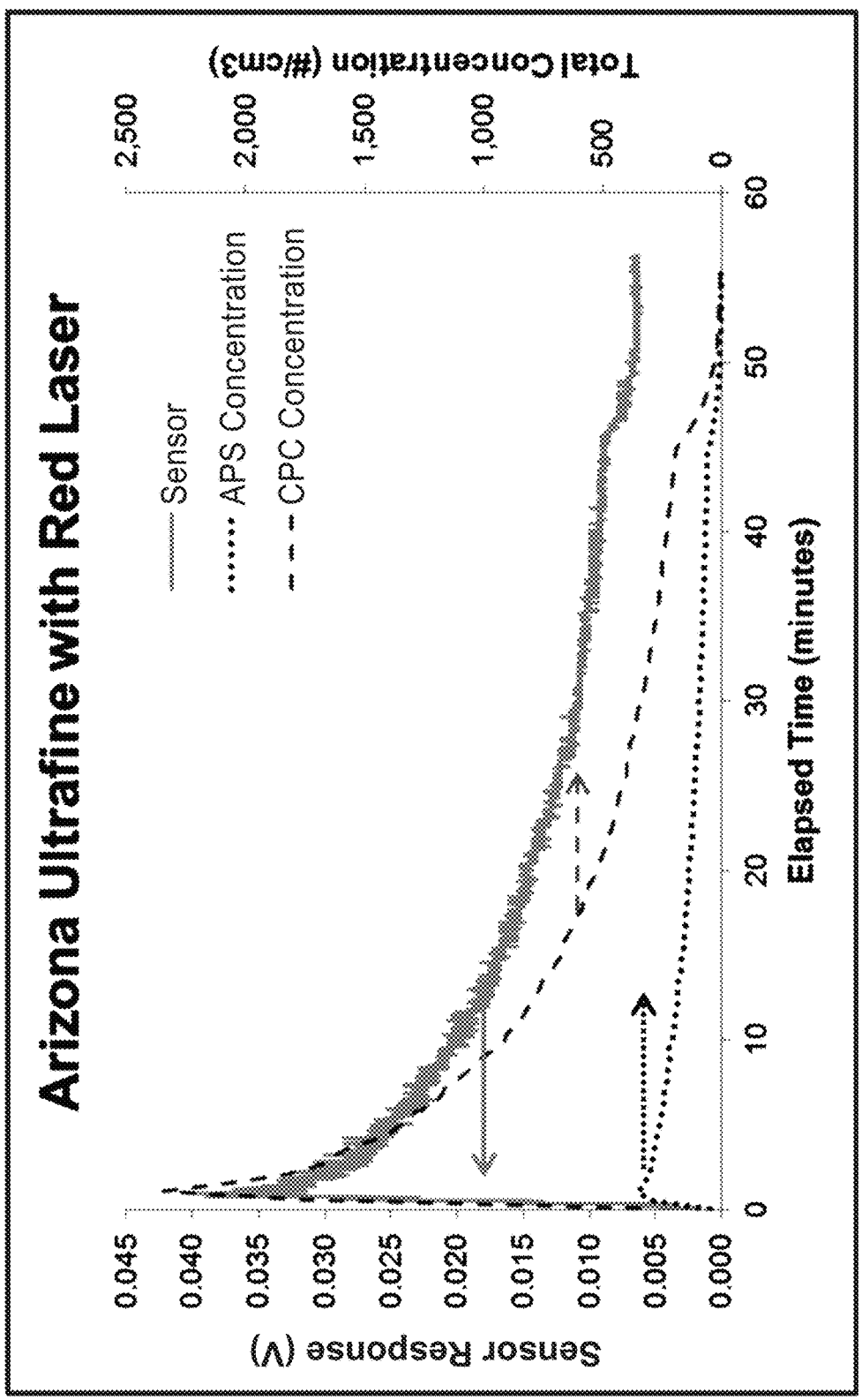
FIG. 13A is a plot of aerosol concentration, in which an aerosol mixing chamber is charged with a quantity of Arizona Ultrafine Road Dust and then sampled by the particle detector described below in Example 1, an Aerodynamic Particle Sizer (APS), and the CPC referred to above in conjunction with FIG. 12; the decay in aerosol concentration in the chamber is captured by all three instruments; the particle detector response reported is the measured voltage minus the baseline measured with the laser on but with particle-free air flowing through the sensor.
Figure 13B:
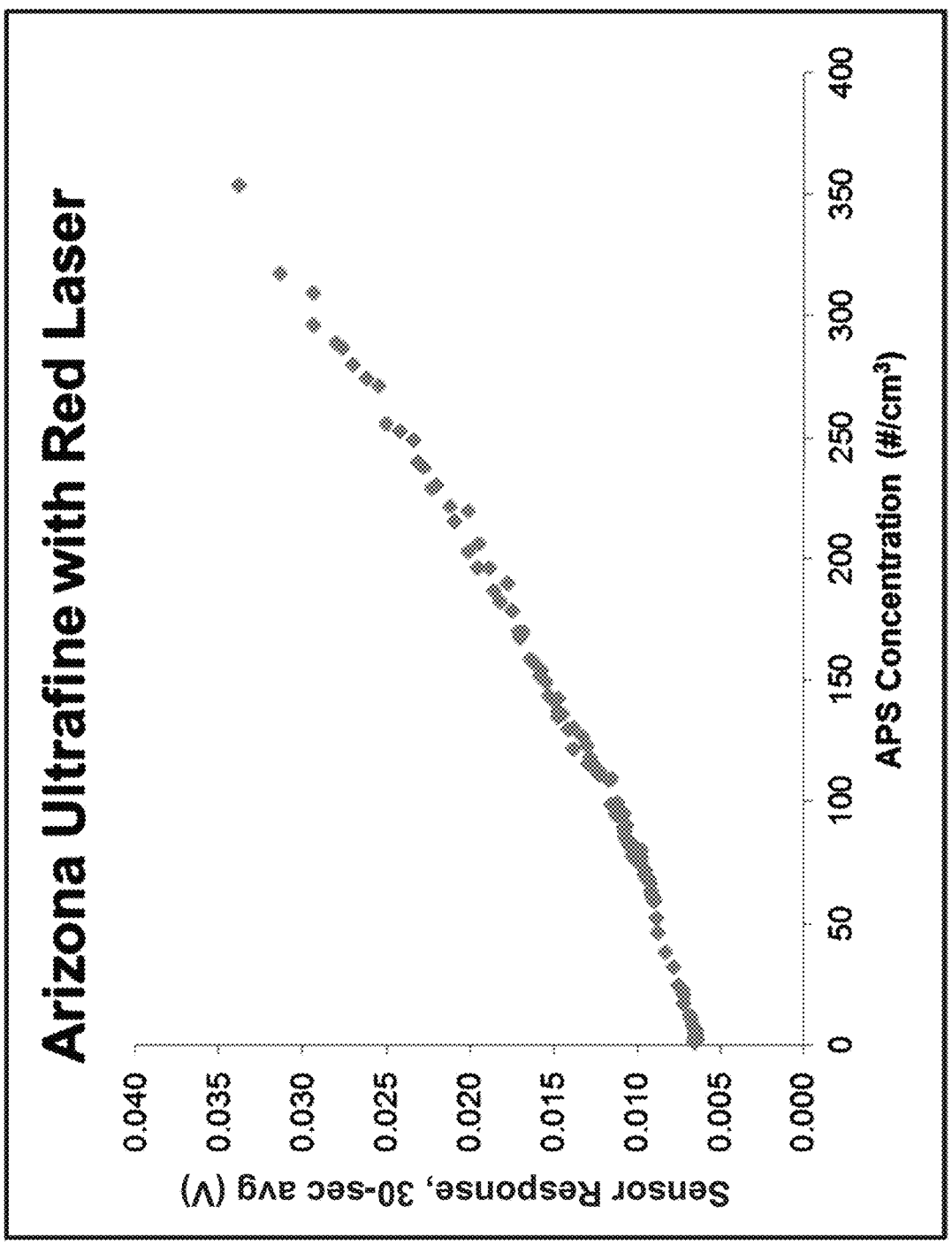
FIG. 13B is a plot comparing the response of the particle detector described below in Example 1 to the particle counting of the APS; the particle detector response reported is the measured voltage minus the baseline measured with the laser on but with particle-free air flowing through the sensor.
Figure 13C:
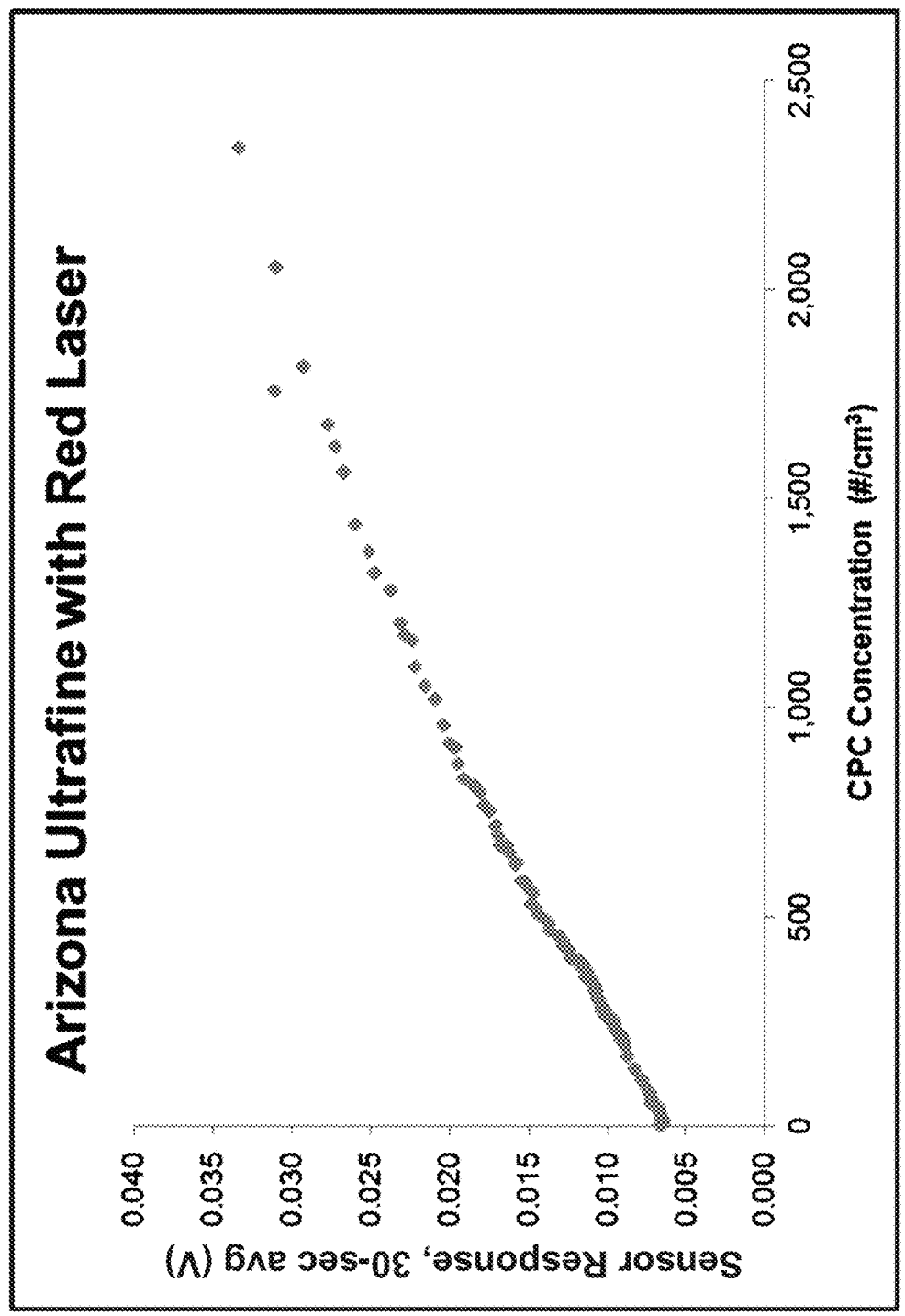
FIG. 13C is a plot comparing the response of the particle detector described below in Example 1 to the particle counting of the CPC; the particle detector response reported is the measured voltage minus the baseline measured with the laser on but with particle-free air flowing through the sensor.

Experiments were conducted using ISO 12103-1, A1 Ultrafine Test Dust (also called Arizona Road Dust). The median size range of the test dust was around 250 nm as measured by the SMPS and shown in FIG. 12. Size distribution of ISO Ultrafine Arizona Road Dust as measured with a TSI SMPS. A typical experiment involved dispersing a small amount of Arizona Road Dust into the aerosol mixing chamber using a TSI Model 3433 Small Scale Powder Disperser. The well mixed aerosol in the chamber was then sampled by the particle detector and the two commercial particle counters (APS and CPC). The aerosol concentration in the chamber slowly decayed over time until the point when a clean out pump was turned on, which drew the aerosol out of the chamber while introducing filtered air into the test chamber. This decay in concentration followed by the clean out is shown in FIG. 13A. The particle detector showed response to the change in concentration similar to the two commercial particle counters. A direct comparison of the particle detector and the two commercial particle counters is shown in FIGS. 13B and 13C. It is noted that with the configuration of the particle detector employed in this experiment, the particle detector provided more of a mass concentration measurement and did not account for particle size. This difference was reflected in the lack of a true 1:1 relationship of the particle detector response and that of the two commercial particle counters. Using different wavelengths of light and calibration algorithms the accuracy of the measurement could be improved. Using a 650 nm red laser in the particle detector, concentrations below 0.9 particles/cm$^3$ and sizes as small as at least 0.25 µm (25 nm) were detected by the particle detector.

EXAMPLE 2—Bioaerosol Detection

In this Example, a particle detector having a configuration similar to that described above in Example 1 was fabricated. However, a 365 nm UV LED with a collimating lens was utilized as the excitation source, and an aluminum heat sink was utilized to hold the LED and maintain a stable temperature. The excitation wavelength was blocked by using a Rosco 400 nm UV filter gel sheet. The UV filter was wrapped around the clear tube. The flexible PV detector was then wrapped around the gel filter thus creating a detection cavity that excludes the excitation radiation from the PV detector.

Figure 14:
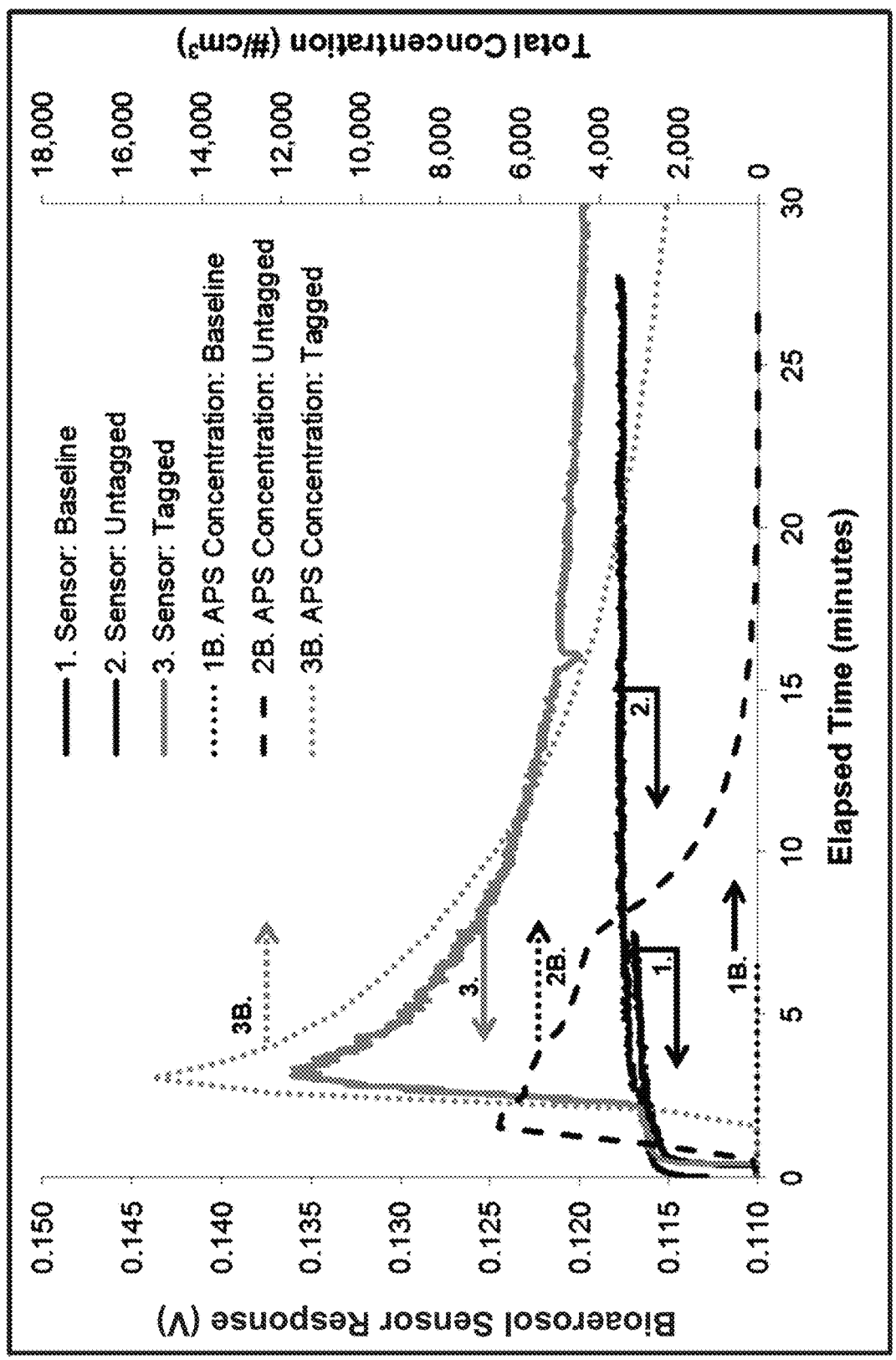
FIG. 14 is a plot of the response of a particle detector as described below in Example 2 to Tinopal tagged and untagged Syloid aerosol as simulants for inert aerosol and bioaerosol; the response of a photovoltaic light detector of the particle detector protected by an ultraviolet UV gel filter is due to emitted fluorescence and not the scattered excitation photons.

Using the same experimental set up as described above in Example 1, a fluorescent aerosol was used as a simulant for a bioaerosol. WR Grace Syloid powder was tagged with 2% Tinopal CBS X. The Tinopal tag has an absorbance maximum of approximately 385 nm. The emission wavelength maximum occurs at approximately 430 nm. Control experiments were conducted using untagged Syloid aerosol to demonstrate that the signal detected by the PV detector was not scattered excitation energy but rather emitted photons from fluorescence. FIG. 14 compares the response of the particle detector to tagged and untagged Syloid aerosol. In this set of experiments stray source radiation was reaching the PV detector, thereby limiting the level of detection.

Figure 15:
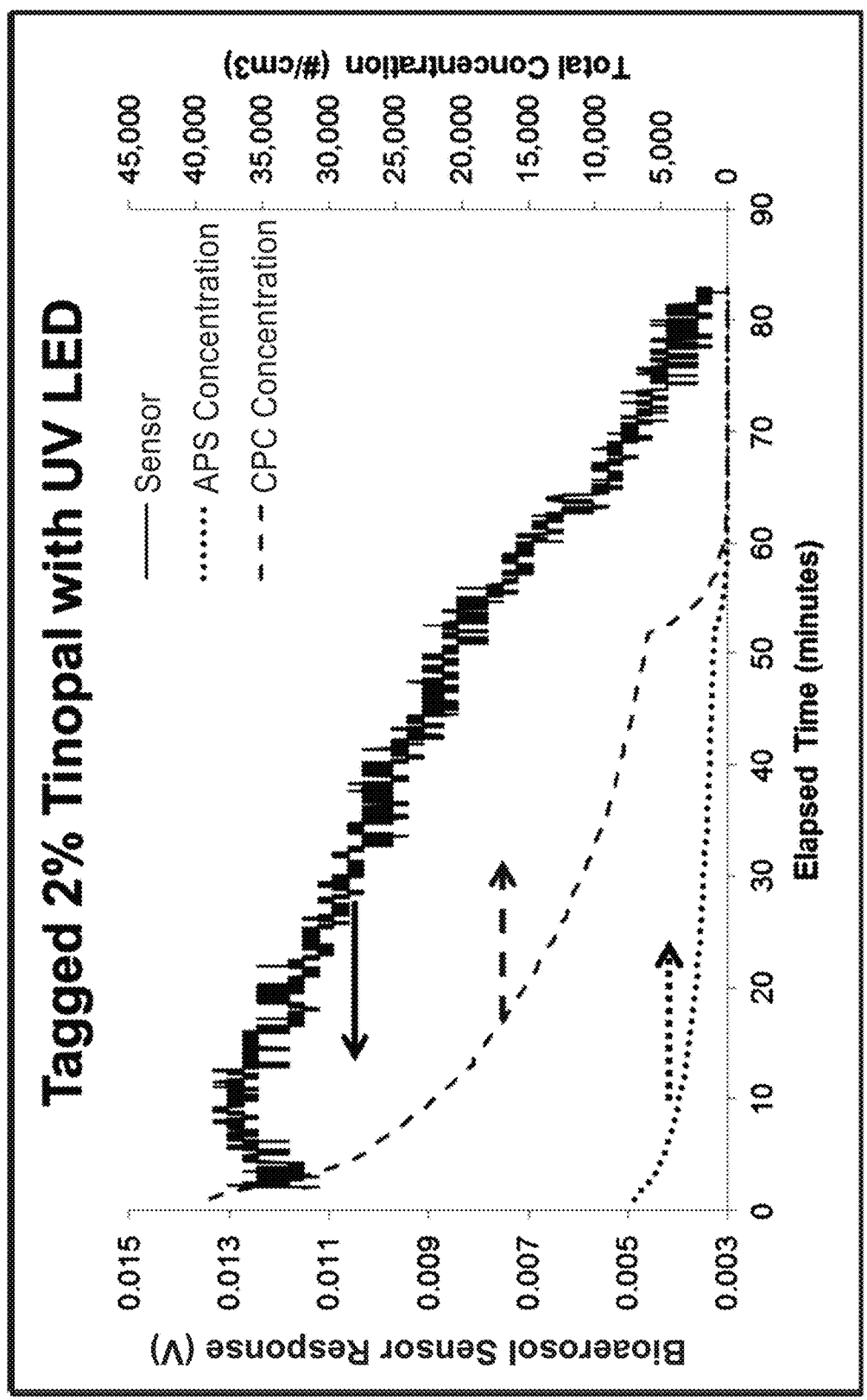
FIG. 15 is a plot of the response of a particle detector as described below in Example 2 to fluorescently tagged Syloid aerosol (2% Tinopal); an APS and CPC provide total particle count (do not measure fluorescence); the particle detector response reported is the measured voltage minus the baseline measured with the laser on but with particle-free air flowing through the sensor.

Adding apertures and improving the collimation of the LED, a second set of experiments was carried out that provided both a lower limit of detection and more sensitivity as shown in FIG. 15. Further improvements are possible with additional improvements to reducing stray source radiation and optimization of the geometry of the sensing cavity and sample flow rate.

EXAMPLE 3—Bioaerosol Detection

In this Example, a particle detector having a configuration similar to that described above in Example 2 was fabricated. However, the particle detector was reconfigured to use a 405 nm violet laser. A similar experimental setup was used as described above in Example 2, except that a controlled concentration of bioaerosol from *Bacillus* spores was introduced into the chamber and sampled with the two commercial particle counters described above and the particle detector. The 405 nm wavelength is at the upper end of excitation of bioparticles. However, a laser provides an intense, coherent light effectively delivered to the bioaerosol in the detection cavity. Violet lasers of 405 nm have previously been demonstrated in detecting bioaerosols. See Saari et al., "Performance of Two Fluorescence-Based Real-Time Bioaerosol Detectors: BioScout vs. UVAPS," *Aerosol Science and Technology* 48(4): 371-378 (2014). The 405 nm laser both scatters elastically (total aerosol detection) and stimulates fluoresce (bioaerosol detection). However, the gel filter used in front of the PV detector in this experiment only blocked excitation light below 400 nm, so both scattered and emitted fluorescence were detected. A second setup was used with just a 650 nm red laser to measure only total aerosol concentration (no fluorescence stimulated). This difference of the signals from the 405 nm and 650 nm provided a crude estimation of the fluorescence signal. Ideally a filter that excludes the 405 excitation light should be employed. Alternatively, UV LEDs with wavelengths below 400 nm could be employed but careful collimation of the light is required.

A simulant for anthrax bacteria, *Bacillus atrophaeus* (*Bg*), was used to test the particle detector. A known concentration of *Bg* spores was injected into the aerosol test chamber using a 3 jet collision nebulizer. The particle detector and APS took data from before injection of *Bg* spores until an unmeasurable concentration was achieved. Viable sampling was done via an all-glass impinger, 4 mm (AGI-4) using impinger fluid to collect the spores. Plating and counting of colonies was used to determine viable counts.

The AGI results were combined with the APS particle size information to estimate time resolved viable bioaerosol concentration. A distinct peak formed around 1 µm when the *Bg* spores were being injected. Other particles present during this event could be growth media or extracellular material. A view of the particle distribution by mass concentration also revealed the tight distribution of single spores. With that information, it is reasonable to extract the size bins of interest from the particle data. In this case, the log distributed average bin sizes of 0.965 µm, 1.037 µm, and 1.114 µm were selected to compensate for binning inconsistencies. These three bins were summed to provide time-resolved particle number concentration information. However, the bracketing bins may also contain some non-spore material, thus providing an overestimate of total spore concentration.

Figure 16:
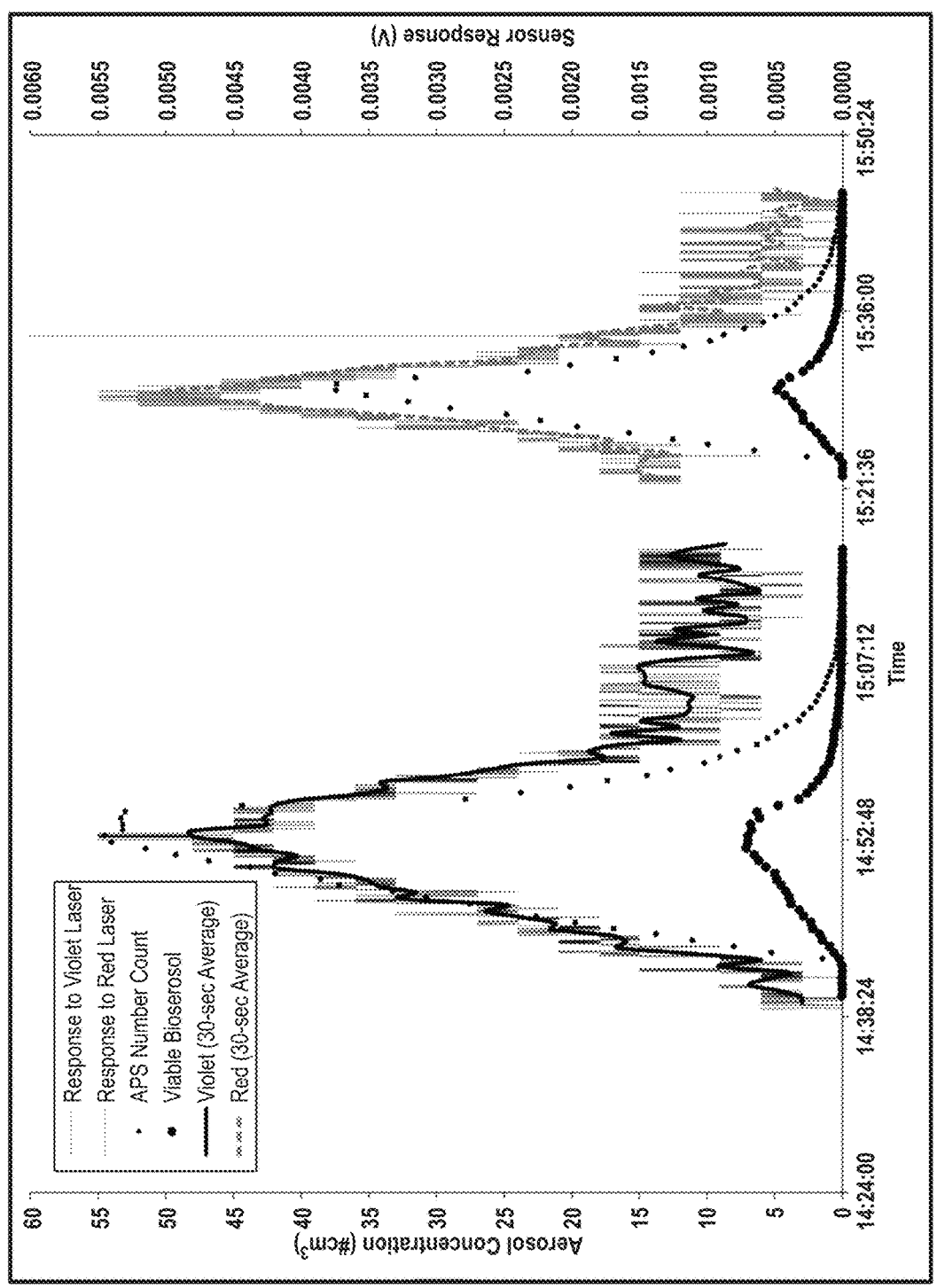
FIG. 16 is a plot of the response of a particle detector as described below in Example 3 with violet 405 nm and red 650 nm lasers for *Bg* spore aerosol.

FIG. 16 shows the results for the particle detector for the *Bg* bioaerosol challenge for measurements with the 405 nm and 650 nm lasers, compared to the APS and estimated viable bioaerosol concentration. The particle detector tracked nicely with the APS concentration, detecting the change in *Bg* concentration from time of injection to decay after the injection was stopped. The lower limit measured by the particle detector was on the order of 0.085 #/cm$^3$.

EXAMPLE 4—Series-Connected and Parallel-Connected Light Detectors

As described above, a light detector (or sensor) according to embodiments described herein may include two or more discrete units of photo-responsive material, which also may be referred to as photo-responsive units or photo-responsive cells, or other alternative terms as noted above. Such a configuration may be referred to as being two or more light detectors that each include a discrete photo-responsive unit or, alternatively, a light detector that includes two or more discrete photo-responsive units. In either case, as described above two or more discrete photo-responsive units may be electrically connected (e.g., wired) in series or in parallel. Series-connected and parallel-connected configurations can improve the output of the particle detector and provide more usable energy. For example, wiring two photo-responsive units together in series will double the maximum output voltage, while wiring two photo-responsive units together in parallel will double the maximum current output. Hence, series-connected and parallel-connected configurations can provide a way to increase the signal gain without using any extra energy or power.

Figure 17A:
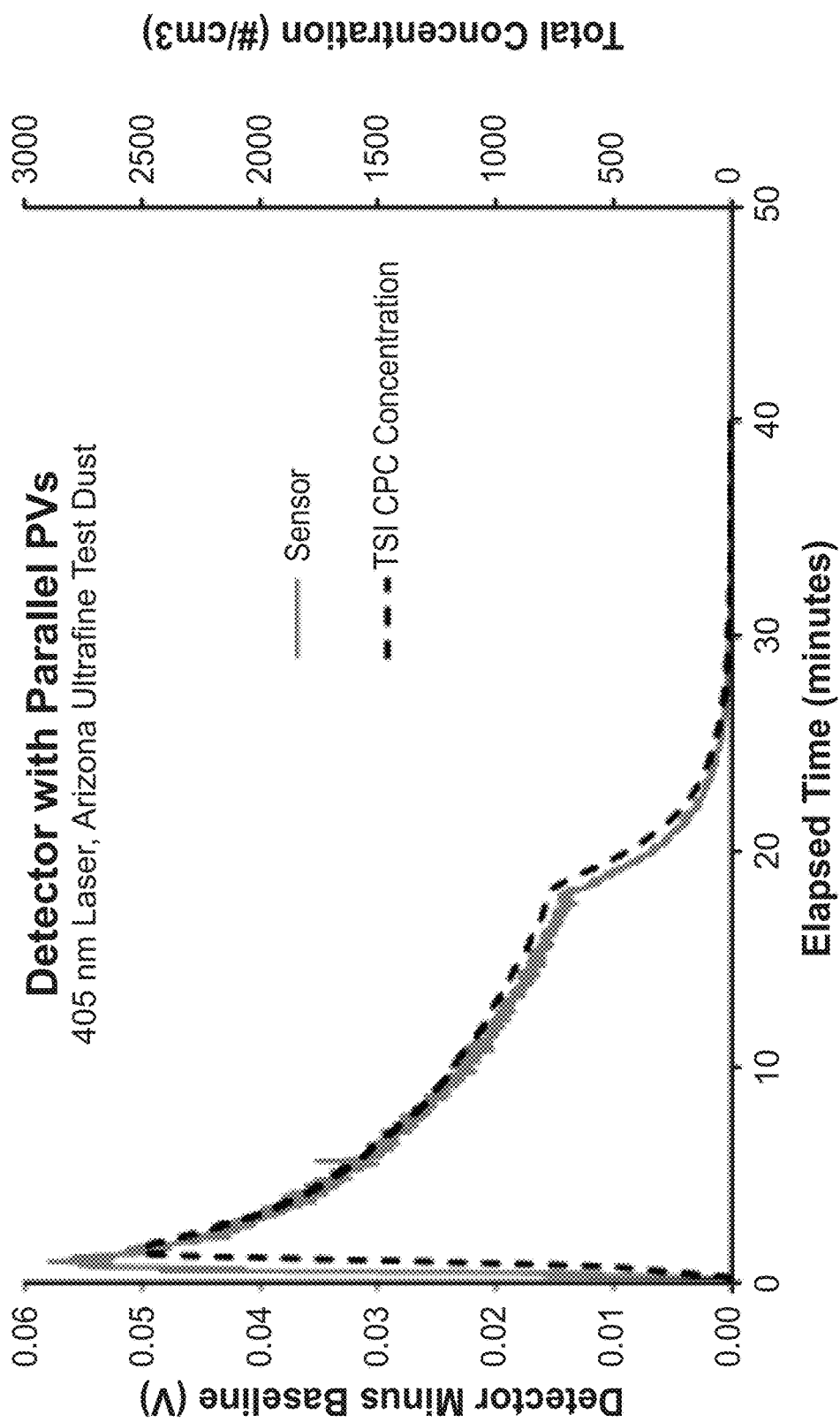
FIG. 17A is a plot of aerosol concentration similar to FIG. 13A, in which the data were acquired in an experiment similar to that described below in Example 1, but utilizing a particle detector including two photo-responsive cells connected in parallel.
Figure 17B:
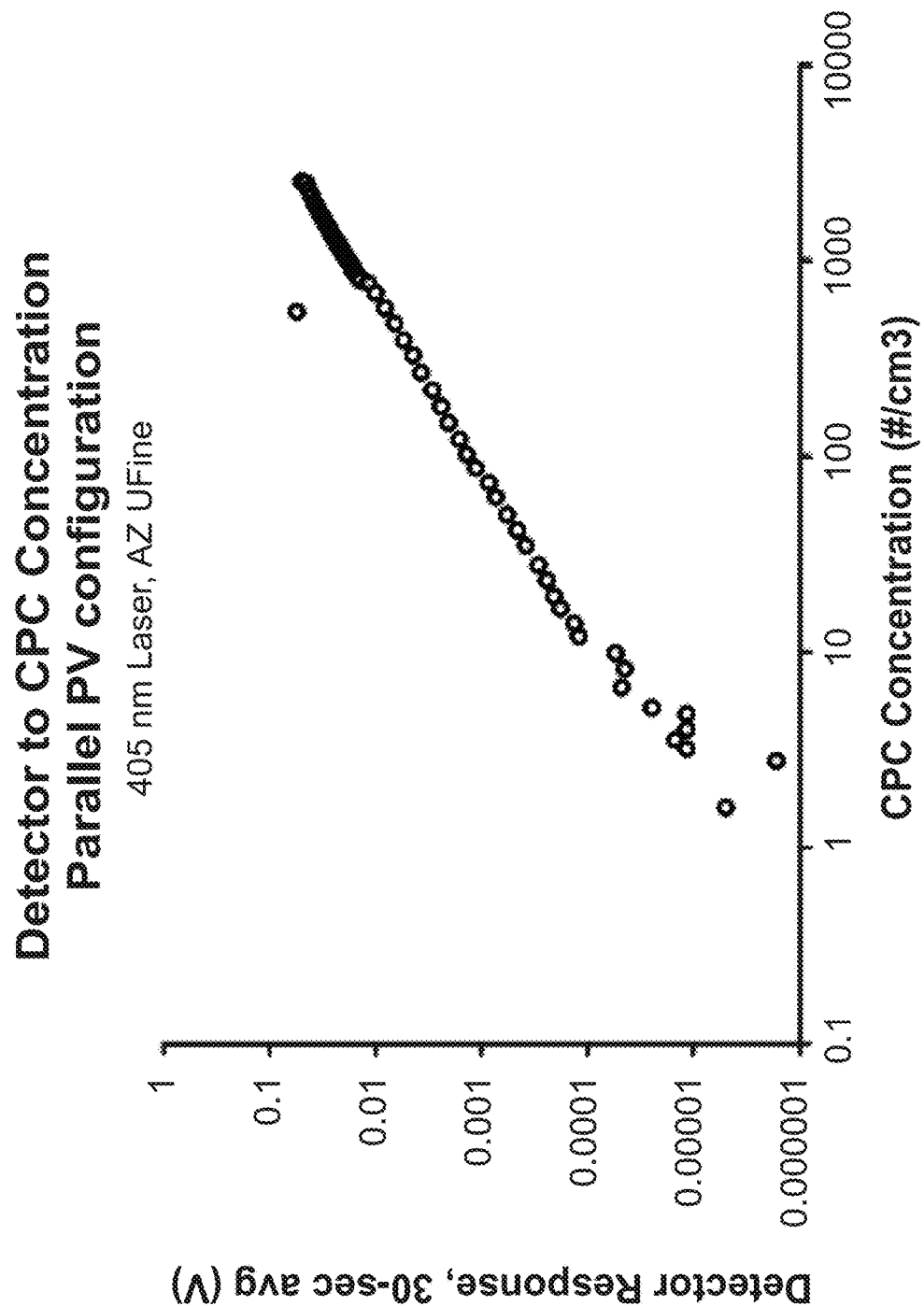
FIG. 17B is a plot similar to FIG. 13C, comparing the response of the particle detector with parallel-connected cells associated with FIG. 17A to the particle counting of the CPC.
Figure 18A:
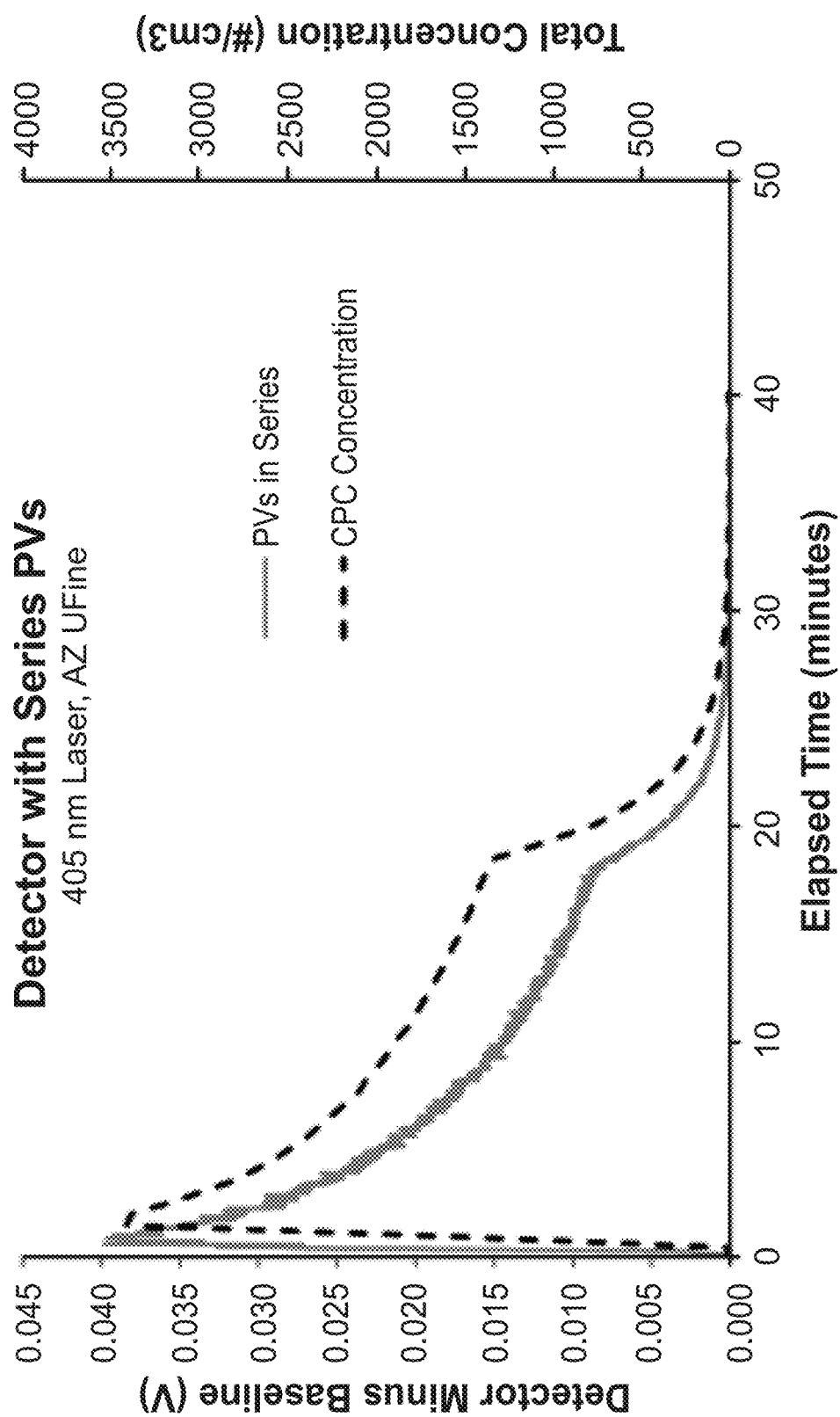
FIG. 18A is a plot of aerosol concentration similar to FIG. 13A, in which the data were acquired in an experiment similar to that described below in Example 1, but utilizing a particle detector including two photo-responsive cells connected in series.
Figure 18B:
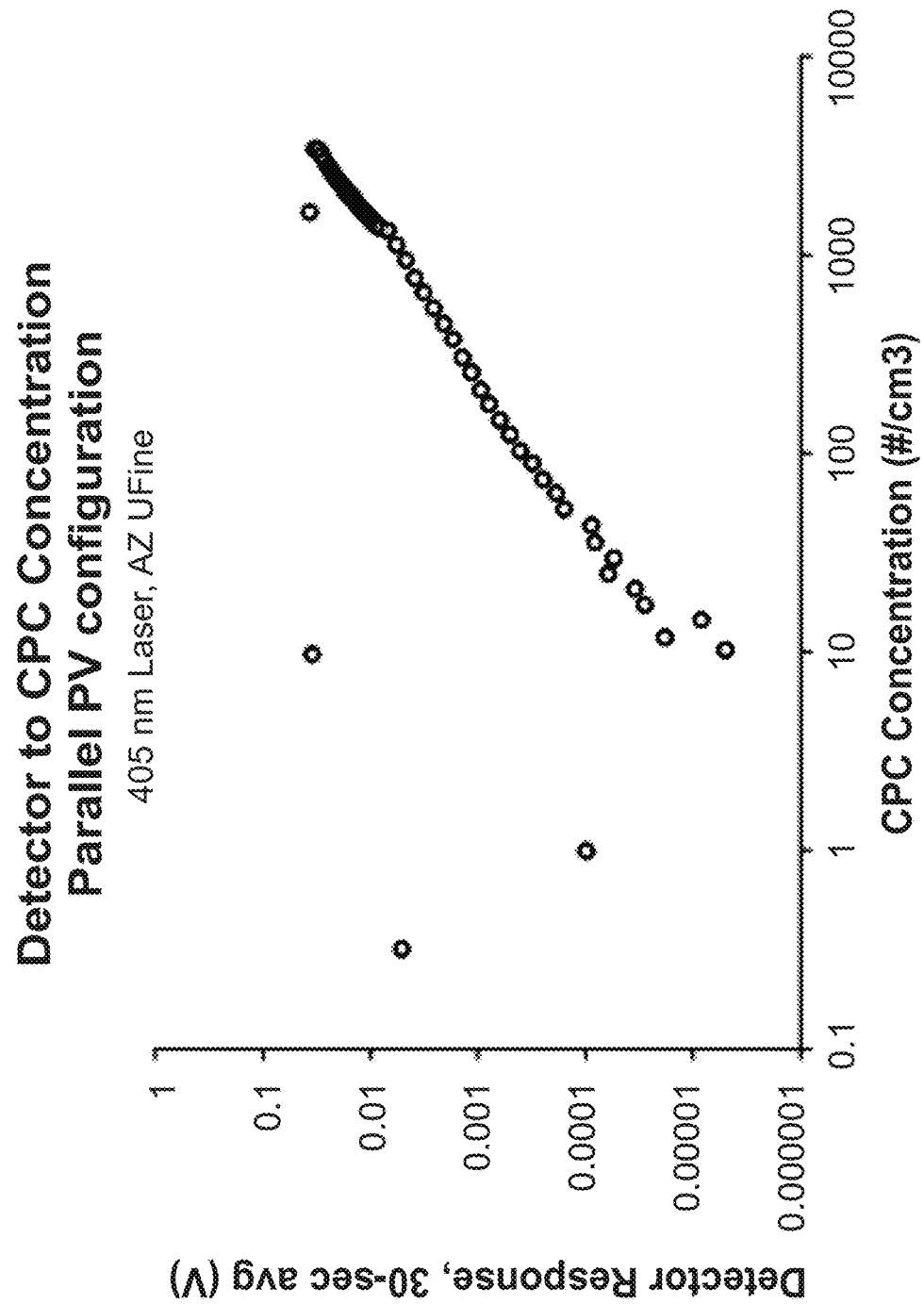
FIG. 18B is a plot similar to FIG. 13C, comparing the response of the particle detector with series-connected cells associated with FIG. 18A to the particle counting of the CPC.

In this Example, laboratory tests were performed using a 405-nm, 20-mW laser for both the series and parallel configurations. The particle detector and experimental set up utilized were as described above in Example 1, and the aerosol sampled was AZ Ultrafine test dust. FIGS. 17A and 17B show the plotted test results of parallel wiring of two PowerFilm cells together (current increase). FIGS. 18A and 18B show the plotted test results of parallel wiring of two PowerFilm cells together (voltage increase). Results show that while the series-wired cells had a lower-end detection that was approximately the same as the lower-end detection of the parallel-wired cells, the cells wired in parallel produced a higher initial response peak and a smoother signal response for a given aerosol concentration.

The cells wired together in this Example had an individual size of 1.5 inches by 4.5 inches before being conformed. The cells may have other sizes as long as their specifications are the same and they fit on or in the detection cavity of the particle detector in the same manner. Changing the size of the detection cavity may affect the amount of stray light seen by the cells, and depends upon the irradiating light beam signal being very tight and without much "halo" or extra light from the light source. The use of a beam-focusing lens and/or apertures can greatly reduce unwanted noise, as described herein.

Embodiments of the light detector disclosed herein may utilize a variety of semiconductors (semiconductor materials) as the photo-responsive material. Examples of such semiconductor materials include, but are not limited to, amorphous silicon (a-Si); crystalline silicon, including polycrystalline silicon (c-Si) and monocrystalline silicon (mc-Si); germanium (Ge); gallium antimonide (GaSb); gallium arsenide (GaAs); aluminum gallium arsenide (AlGaAs); indium gallium arsenide (InGaAs); indium phosphide (InP); and cadmium telluride (CdTe). As appreciated by persons skilled in the art, the foregoing list encompasses various other related species of semiconductor materials exhibiting photo-responsive activity suitable for use as a light detector as described herein. Such other related species may include, for example, other Group III-V and Group II-VI materials, including tertiary and quaternary alloys or compounds of one or more species of the foregoing list, as well as one or more species of the foregoing list that may be doped with or otherwise include additional elements.

Different semiconductor materials have different free electron band gaps (or energy gaps). As appreciated by persons skilled in the art, the term "band gap" or "energy gap" refers to the region in a semiconductor material (e.g., a solar cell or other semiconductor solid) where no electrons can exist. When the semiconductor material is excited and gains energy by a photon (light), the free electrons that are emitted "jump" across the band gap, thereby creating a voltage or current increase on the output of the semiconductor material. The lower (or narrower) this band gap is, the easier it is for these electrons to move across the two energy states, which in turn allows the semiconductor material to be more sensitive to low light (photon) excitation. Hence, at least when disregarding all other factors that may be pertinent to the specification of the semiconductor material, a lower band gap is preferred over a higher band gap.

Further examples of semiconductor materials that may be utilized as the photo-responsive material in embodiments disclosed herein include, but are not limited to, semiconductor materials having a band gap in a range of about 2 eV or less; or from about 0.67 eV to about 2 eV; or about 1.7 eV or less; or from about 0.67 eV to about 1.7 eV; or from about 1.1 eV to about 1.7 eV; or about 1.1 eV or less; or from about 0.67 eV to about 1.1 eV. Examples of semiconductor materials with band gaps in the range from about 0.67 eV to about 2 eV include, but are not limited to, those specifically noted above: a-Si, c-Si, mc-Si, Ge, GaSb, GaAs, AlGaAs, InGaAs, InP, and CdTe.

Some of the semiconductor materials noted above are sufficiently mechanically flexible as to be suitable for use with the flexible light detectors described herein, i.e., they are conformable to a curved structure such as a cylindrical detection cavity. Other semiconductor materials noted above may be considered as being mechanically inflexible (or substantially mechanically inflexible) at least insofar as, in practice, they generally are not suitable for use with the flexible light detectors described herein. That is, an inflexible semiconductor material is not readily conformable due to, for example, being susceptible to damage in response to being deformed from a nominal flat, planar state. Amorphous silicon is presently the most commercially available and cost-effective flexible semiconductor material. Amorphous silicon is thus a typical, yet non-limiting, example of the photo-responsive material utilized in flexible light detectors described herein, one specific example being the PowerFilm cells noted herein. Amorphous silicon has a band gap of 1.7 electron volts (eV). Crystalline silicon, including polycrystalline silicon (c-Si) and monocrystalline silicon (mc-Si), is a widely commercially available and cost-effective choice for solar cells. Crystalline silicon is inflexible and consequently is limited for use in light detectors having a flat, planar geometry. However, crystalline silicon has a band gap of 1.1 and thus exhibits increased sensitivity to photons as compared to amorphous silicon. Thus, depending on the embodiment or application, crystalline silicon may be preferred over amorphous silicon.

Figure 19:
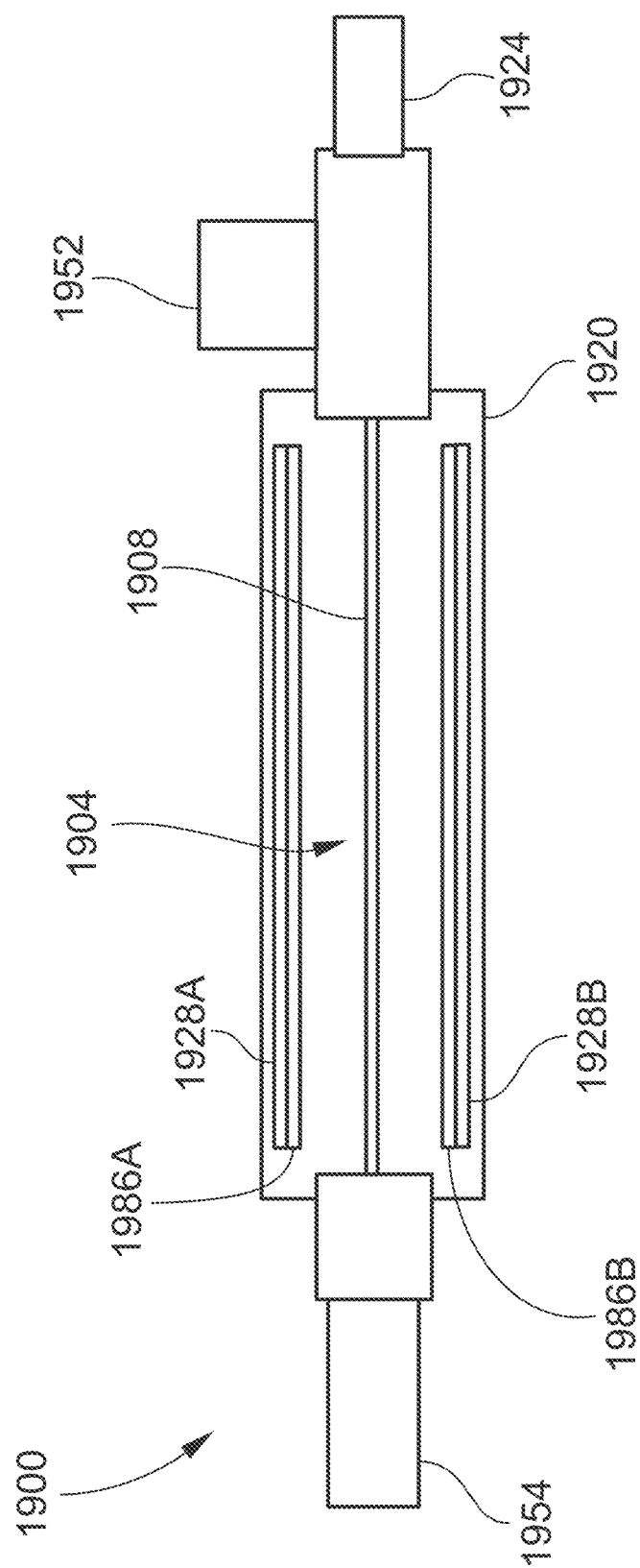
FIG. 19 is a schematic plan view of an example of a particle detector according to another embodiment.

FIG. 19 is a schematic plan view of an example of a particle detector 1900 according to another embodiment. The particle detector 1900 may include a housing 1920 enclosing a flow-through detection cavity 1904 that defines a sample flow path through the particle detector 1900 and an interaction region for particles and irradiating light, one or more light sources 1924 configured for emitting one or more irradiating light beams 1908, and one or more light detectors 1928A and 1928B for receiving scattered or emitted measurement light from the particles. The housing 1920 includes a sample inlet 1952 and a sample outlet 1954 positioned such that the housing 1920 defines a sample flow path from the sample inlet 1952, through the detection cavity 1904 along a longitudinal axis of the particle detector 1900, and to the sample outlet 1954. The housing 1920 may be configured such that the sample inlet 1952 (as illustrated) and/or the sample outlet 1954 are oriented at an angle to the longitudinal axis (e.g., ninety degrees) to minimize entry of stray light into the detection cavity 1904, as described herein.

In the illustrated embodiment, the light source 1924 is located on the same end of the detection cavity 1904 as the sample inlet 1952, and is configured to direct the irradiating light beam 1908 in the same direction as the fluid flow. In other embodiments, the light source 1924 may be located on the same end of the detection cavity 1904 as the sample outlet 1954, and is configured to direct the irradiating light beam 1908 in the direction opposite to the fluid flow. In other embodiments, the light source 1924 may be located at a position offset from the longitudinal axis. In the illustrated embodiment, the light source 1924 is configured to direct the irradiating light beam 1908 in a straight line along the longitudinal axis. In other embodiments, the light source 1924 may be configured to direct the irradiating light beam 1908 at one or more angles to the longitudinal axis.

In the illustrated embodiment two light detectors 1928A and 1928B are provided, positioned geometrically parallel to each other, while in other embodiments a single light detector or more than two light detectors may be provided. In some embodiments, each light detector 1928A and 1928B may represent a plurality of individual light detectors (photo-responsive units), which may be electrically isolated from each other or connected in parallel or in series, as described herein. The detection cavity 1904 and the light detectors 1928A and 1928B may be elongated along the longitudinal axis to increase the total detection area covered by the photo-responsive material or by an increased number of individual photo-responsive units.

In the present embodiment, the light detectors 1928A and 1928B each have a flat, planar geometry, which is shown by side view in FIG. 19. To facilitate positioning the light detectors 1928A and 1928B in a stable manner, the housing 1920 and thus the detection cavity 1904 may be polygonal, i.e., may have a polygonal cross-section in the plane orthogonal to the longitudinal axis of the particle detector 1900. One or more flat, planar light detectors 1928A and 1928B may be positioned at one or more of the flat sides (wall sections) of the polygonal housing 1920. FIG. 11 is representative of an end view of the flat, planar detector geometry, illustrating an embodiment in which the housing has a rectilinear cross-section and four (two opposing pairs) of flat, planar light detectors 1128A, 1128B, 1128C, and 1128D are positioned at the respective four sides of the housing. In other embodiments, the housing may be triangular or may have more than four sides (e.g., hexagonal, octagonal, etc.), with light detectors positioned at one or more of the different sides.

The flat, planar detector geometry enables any photoactive semiconductor material to be utilized as the photo-responsive material, such as those noted above. In particular, however, the flat, planar detector geometry enables lower band gap semiconductors that are not necessarily flexible to be utilized, as the semiconductors do not need to be conformable to a curved surface. For example, crystalline silicon may be utilized.

The particle detector 1900 may also include one or more optical filters 1986A and 1986B positioned to filter measurement light prior to incidence on the respective light detectors 1928A and 1928B, as described herein. The light detectors 1928A and 1928B and the optical filters 1986A and 1986B may be positioned on the inside of the outside of the housing 1920, as described herein. The particle detector 1900 may also include one or more other features described herein such as, for example, a light trap, a data acquisition device, one or more devices for blocking stray/ambient light, beam-shaping optics, one or more heat sinks, a fluid moving device, structural transition sections of increasing and/or decreasing size, etc.

EXAMPLE 5—Flat-Geometry Light Detectors

A particle detector consistent with the particle detector 1900 described above and illustrated in FIG. 19 was tested. The housing was a black enclosure of rectilinear geometry with dimensions of 4.5-inch×3-inch×2-inch. One-half-inch fittings were utilized as the sample inlet and sample outlet. The light source utilized was a red (650 nm) or violet (405 nm) laser that was beamed straight through the enclosure in the same direction as the air flow, between two crystalline silicon detectors placed geometrically parallel to each other and the laser beam. The silicon detectors were 3.5-inch×2-inch solar cells commercially available from Ningbo Sunboy New Energy Co., Ltd, Ningbo, Zhejiang, China. The flow rate was 5 liters per minute (lpm). A TSI aerodynamic particle sizer (APS) was positioned downstream to sample the same air stream as the particle detector and provide the air flow for both devices. The particle detector was able to measure aerosol concentration (Ultrafine Arizona Road Dust) in synchronization with the TSI APS and a TSI Condensation Nucleus Counter (CPC).

Figure 20:
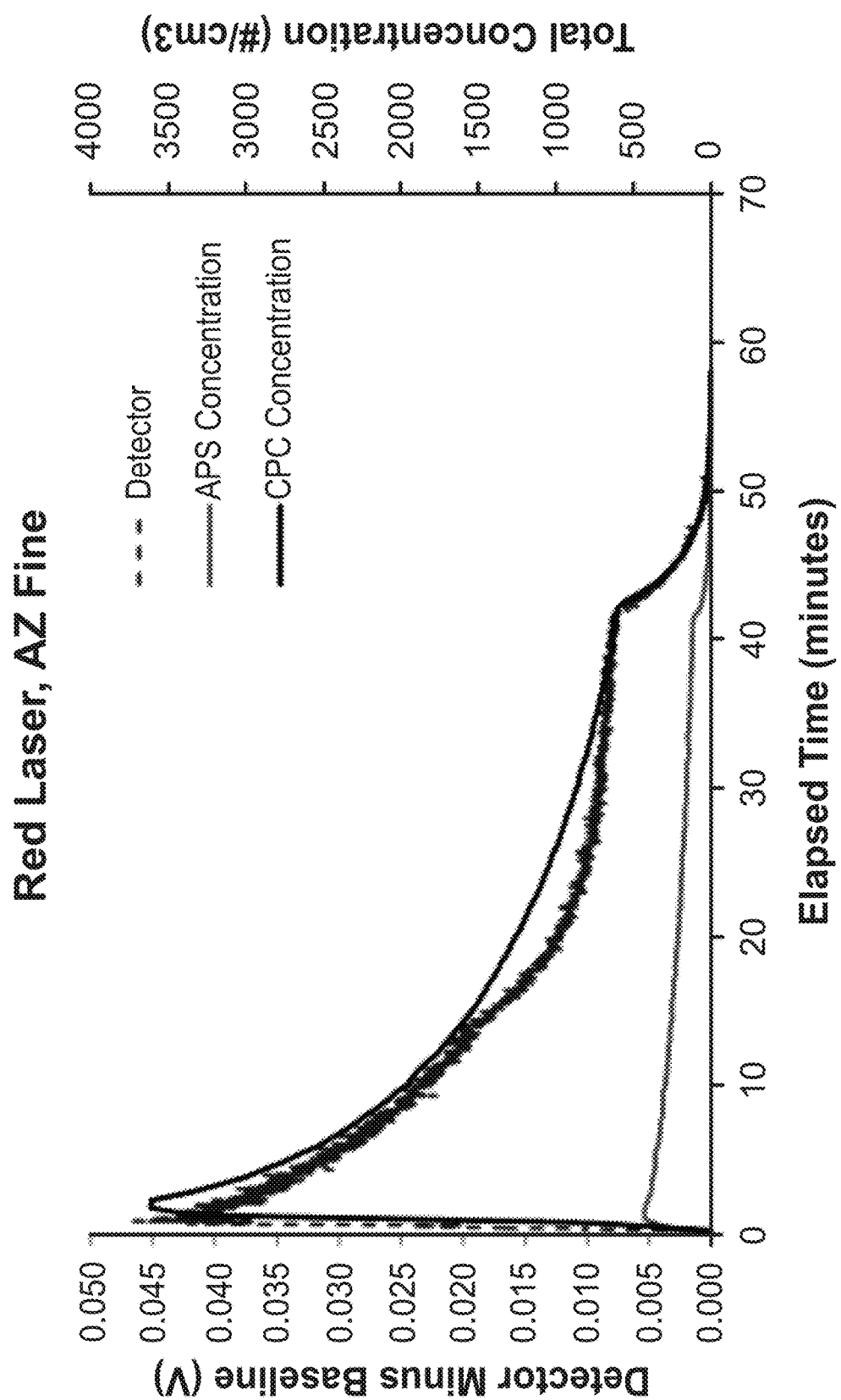
FIG. 20 is a plot of aerosol concentration similar to FIG. 13A, in which an aerosol containing Ultrafine Arizona Road Dust was sampled by the particle detector described below in Example 5, an Aerodynamic Particle Sizer (APS), and the CPC referred to above in conjunction with FIG. 12; the decay in aerosol concentration in the chamber is captured by all three instruments; the particle detector response reported is the measured voltage minus the baseline measured with the laser on but with particle-free air flowing through the sensor.

FIG. 20 is a plot of aerosol concentration acquired during this test. The decay in aerosol concentration is captured by all three instruments. The particle detector response reported is the measured voltage minus the baseline measured with the laser on but with particle-free air flowing through the particle detector. FIG. 20 demonstrates that the particle detector under test tracked the particle concentration down to the detection threshold of the APS. At this point the particle detector response was at the signal baseline.

Figure 21:
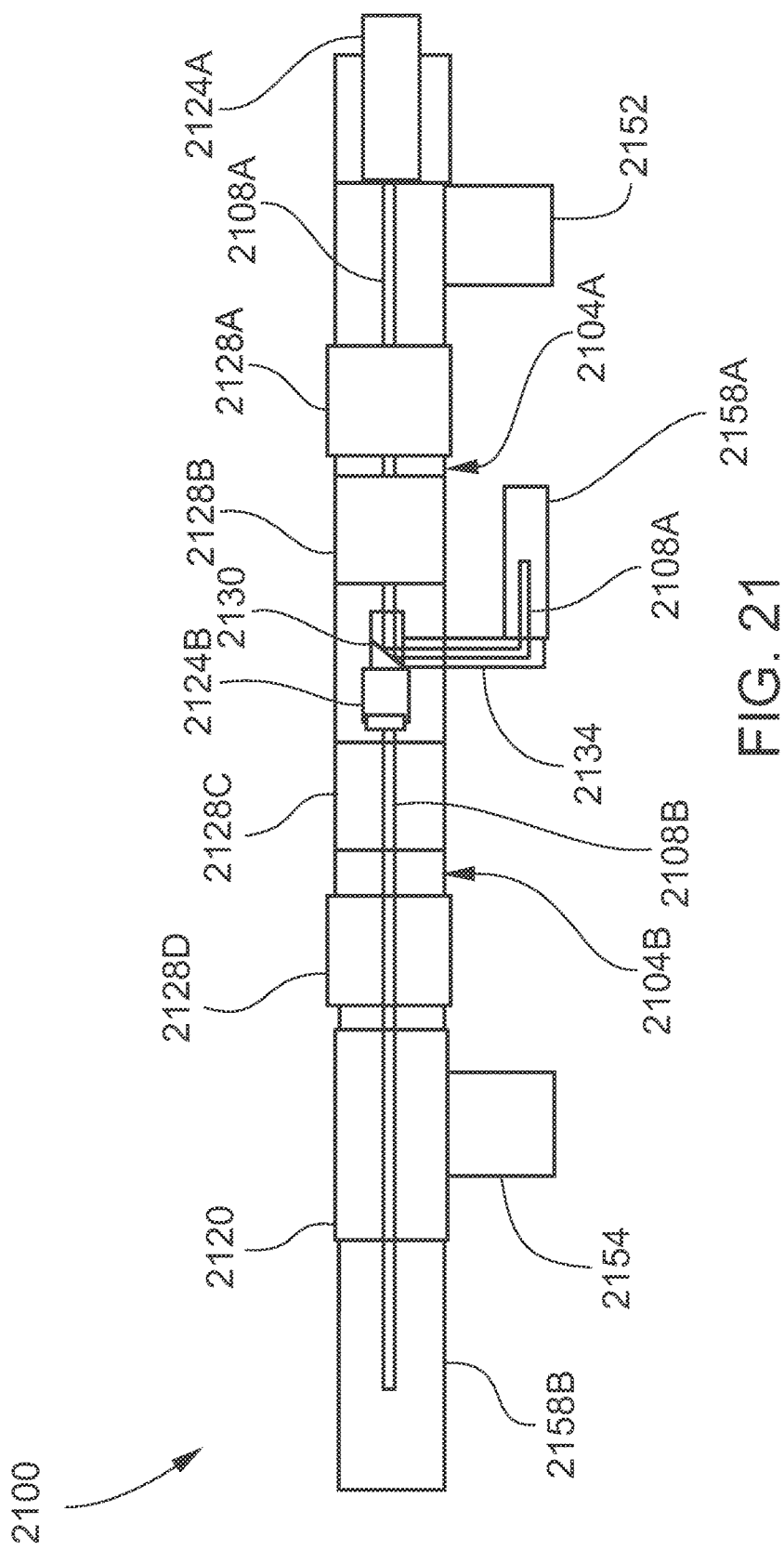
FIG. 21 is a schematic plan view of an example of a particle detector according to another embodiment that includes a plurality of light sources.

As described herein, particle detectors according to some embodiments may include a plurality of light sources. FIG. 21 is a schematic plan view of an example of a particle detector 2100 according to another embodiment that includes a plurality of light sources. In addition to the light sources, the particle detector 2100 may include a housing 2120 enclosing a flow-through detection cavity that defines a sample flow path through the particle detector 2100 and an interaction region for particles and irradiating light, and one or more light detectors 2128A, 2128B, 2128C, and 2128D for receiving scattered or emitted measurement light from the particles. The housing 2120 includes a sample inlet 2152 and a sample outlet 2154 positioned such that the housing 2120 defines a sample flow path from the sample inlet 2152, through the detection cavity along a longitudinal axis of the particle detector 2100, and to the sample outlet 2154. The housing 2120 may be configured such that the sample inlet 2152 and/or the sample outlet 2154 are oriented at an angle (e.g., ninety degrees) to the longitudinal axis 2132 to minimize entry of stray light into the detection cavity 2104, as described herein.

In the illustrated embodiment, the plurality of light sources includes at least a first light source 2124A and a second light source 2124B. The first light source 2124A may be configured for emitting a first irradiating light beam 2108A, while the second light source 2124B may be configured for emitting a second irradiating light beam 2108B. The first irradiating light beam 2108A and the second irradiating light beam 2108B may have the same or different wavelengths. In the case of different wavelengths, the first light source 2124A and the second light source 2124B may be different types. For example, the first light source 2124A may be a laser while the second light source 2124B may be an LED, or vice versa, or both light sources 2124A and 2124B may be lasers, or both light sources 2124A and 2124B may be LEDs, etc. One of the irradiating light beams 2108A and 2108B may be selected for generating scattered measurement light from the particles, while the other is selected for generating fluorescent measurement light from the particles. As one non-limiting example, the first light source 2124A may emit photons having a wavelength of 405 nm (violet), while the second light source 2124B may emit photons having a wavelength of 280 nm (UV).

In the present embodiment, the first light source 2124A and the second light source 2124B are configured (positioned) as needed such that the first irradiating light beam 2108A and the second irradiating light beam 2108B propagate along the common longitudinal axis 2132. For example, as illustrated the second light source 2124B may be positioned downstream from the first light source 2124A, and a mirror 2130 may be positioned upstream of the second light source 2124B. The mirror 2130 is configured (positioned) to deflect the first irradiating light beam 2108A out from the detection cavity at an angle (e.g., ninety degrees) to the longitudinal axis, such that the first irradiating light beam 2108A does not comingle with the second irradiating light beam 2108B and does not irradiate particles downstream from the second light source 2124B. By this configuration, the detection cavity includes two distinct detection cavities, or "detection zones" (or interaction zones) 2104A and 2104B. Particles in the first detection zone 2104A are irradiated solely by the first irradiating light beam 2108A, and particles in the second detection zone 2104B are irradiated solely by the second irradiating light beam 2108B (although particles in the second detection zone 2104B may have been previously irradiated by the first irradiating light beam 2108A while traveling through the first detection zone 2104A). After being deflected by the mirror 2130, the first irradiating light beam 2108A may exit the first detection zone 2104A via a side conduit 2134 of the housing 2120. This configuration enables particles in a sample fluid introduced into the particle detector 2100 to be subjected to irradiation at two different wavelengths, whereby two distinct measurements may be made. For example, the two distinct measurements may entail scattering at two different wavelengths, or scattering at one wavelength and fluorescence at another wavelength, etc.

In the present embodiment, one or more light detectors are associated with each of the first detection zone 2104A and the second detection zone 2104B. In the embodiment specifically illustrated in FIG. 21, two light detectors 2128A and 2128B are configured to receive measurement light from the first detection zone 2104A, and two light detectors 2128C and 2128D are configured to receive measurement light from the second detection zone 2104B. The light detectors 2128A, 2128B, 2128C, and 2128D may be flexible detectors as described herein, flat planar detectors as described herein, or a combination of both types of detectors. One or more of the light detectors 2128A, 2128B, 2128C, and 2128D may include a plurality of individual light detectors (photoresponsive units), which may be electrically isolated from each other, connected in series, or connected in parallel, as described herein. The detection cavity (detection zones 2104A and 2104B) and the light detectors 2128A, 2128B, 2128C, and 2128D may be elongated along the corresponding longitudinal axes to increase the total detection area covered by the photo-responsive material or by an increased number of individual photo-responsive units. As in other embodiments, the measurement light incident on one or more of the light detectors 2128A, 2128B, 2128C, and 2128D may be filtered by an optical filter (not specifically shown) in the manner described herein. For example, one of the two light detectors 2128A and 2128B may be filtered to block UV radiation while the other light detector 2128A and 2128B is unfiltered. Similarly, one of the two light detectors 2128C and 2128D may be filtered to block UV radiation while the other light detector 2128C and 2128D is unfiltered. The filtering of UV radiation may be useful, for example, when it is desired to collect measurement light resulting from scattered radiation without collecting measurement light resulting from fluorescence, or to collect measurement light without collecting irradiating UV light emitted directly from a UV light detector (i.e., light originating from a light detector that does not interact with particles of the sample fluid).

The particle detector 2100 may include separate light traps 2158A and 2158B for receiving the first irradiating light beam 2108A and the second irradiating light beam 2108B, as illustrated. The particle detector 2100 may also include one or more other features described herein such as, for example, a data acquisition device, one or more devices for blocking stray/ambient light, beam-shaping optics, one or more heat sinks, a fluid moving device, structural transition sections of increasing and/or decreasing size, etc.

Figure 22:
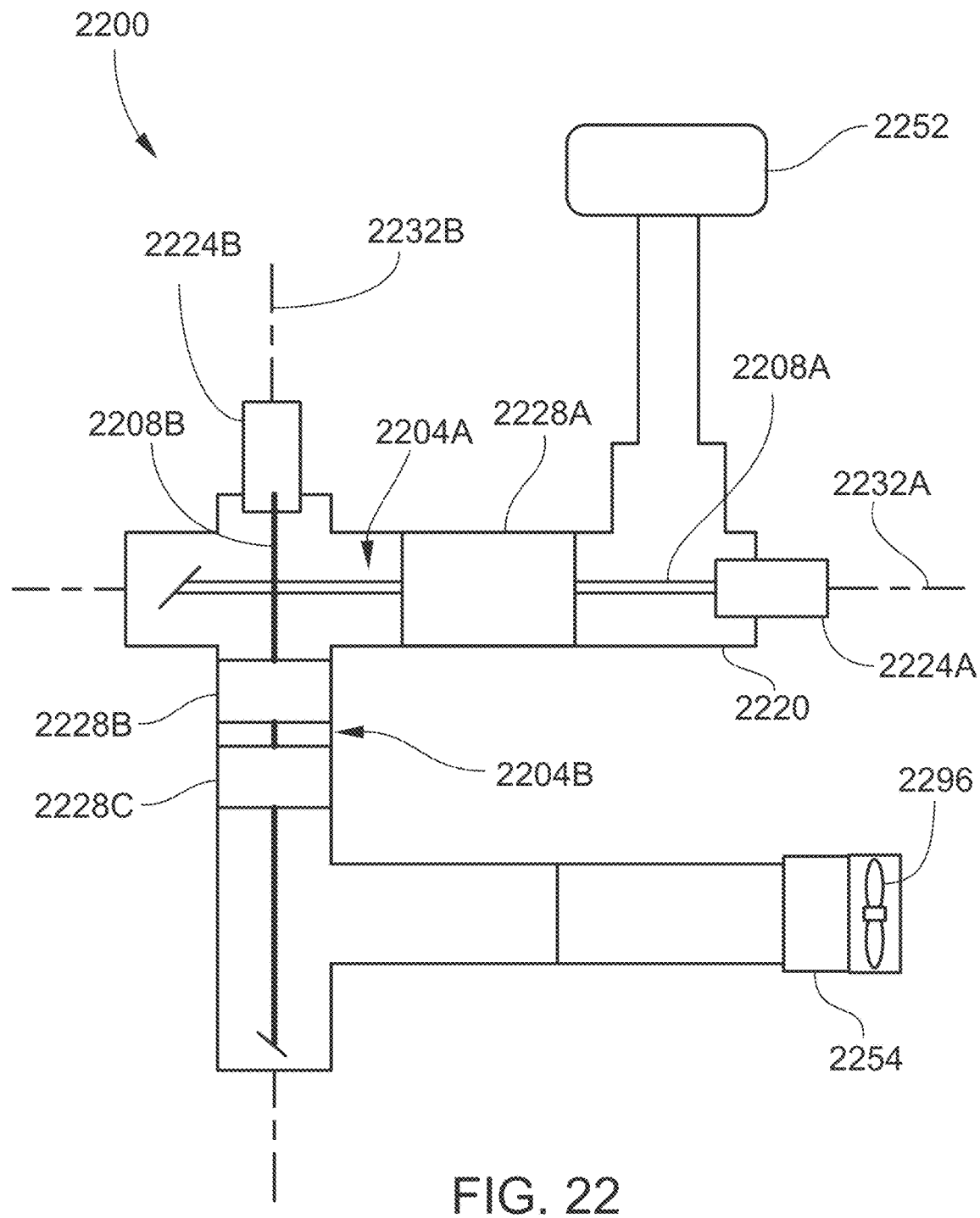
FIG. 22 is a schematic plan view of an example of a particle detector according to another embodiment that includes a plurality of light sources.

FIG. 22 is a schematic plan view of an example of a particle detector 2200 according to another embodiment that includes a plurality of light sources. In addition to the light sources, the particle detector 2200 may include a housing 2220 enclosing a flow-through detection cavity that defines a sample flow path through the particle detector 2200 and an interaction region for particles and irradiating light, and one or more light detectors for receiving scattered or emitted measurement light from the particles. In the present embodiment, the housing 2220 is configured such that the detection cavity is defined by a plurality of distinct detection cavities, or "detection zones" (or interaction zones). In the example specifically illustrated in FIG. 22, the housing 2220 includes a first detection zone 2204A elongated or extending along a first longitudinal axis 2232A, and a second detection zone 2204B elongated or extending along a second longitudinal axis 2232B. The longitudinal axes 2232A and 2232B, and thus the detection zones 2204A and 2204B, are oriented at an angle to each other, for example ninety degrees. The housing 2220 further includes a sample inlet 2252 and a sample outlet 2254 positioned such that the housing 2220 defines a sample flow path from the sample inlet 2252, through the first detection zone 2204A along the first longitudinal axis 2232A, through the second detection zone 2204B along the second longitudinal axis 2232B, and to the sample outlet 2254. As illustrated, the housing 2220 may be configured such that the sample inlet 2252 and/or the sample outlet 2254 are oriented at an angle (e.g., ninety degrees) to the respective longitudinal axes 2232A and 2232B to minimize entry of stray light into the detection zones 2204A and 2204B.

In the present embodiment, the plurality of light sources includes at least a first light source 2224A and a second light source 2224B. The first light source 2224A may be configured for emitting a first irradiating light beam 2208A, while the second light source 2224B may be configured for emitting a second irradiating light beam 2208B. The first irradiating light beam 2208A and the second irradiating light beam 2208B may have the same or different wavelengths. In the case of different wavelengths, the first light source 2224A and the second light source 2224B may be different types. For example, the first light source 2224A may be a laser while the second light source 2224B may be an LED, or vice versa, or both light sources 2224A and 2224B may be lasers, or both light sources 2224A and 2224B may be LEDs, etc. One of the irradiating light beams 2208A and 2208B may be selected for generating scattered measurement light from the particles, while the other is selected for generating fluorescent measurement light from the particles. As one non-limiting example, the first light source 2224A may emit photons having a wavelength of 405 nm (violet), while the second light source 2224B may emit photons having a wavelength of 280 nm (UV).

In the present embodiment, the first light source 2224A and the second light source 2224B are configured (positioned) as needed such that the first irradiating light beam 2208A propagates along the first longitudinal axis 2232A and the second irradiating light beam 2208B propagates along the second longitudinal axis 2232B. Measures may be taken to prevent the first irradiating light beam 2208A from comingling with the second irradiating light beam 2208B and from irradiating particles downstream from the second light source 2224B. For example, similar to the embodiment described above in conjunction with FIG. 21, a mirror (not shown) may be positioned upstream of the second light source 2224B or at least upstream of the second irradiating light beam 2208B such that the mirror is positioned between the first detection zone 2204A and the second detection zone 2204B. The mirror may be configured (positioned) to deflect the first irradiating light beam 2208A out from the detection cavity at an angle (e.g., ninety degrees) to the first longitudinal axis 2232A. After being deflected by the mirror, the first irradiating light beam 2208A may exit the first detection zone 2204A via a side conduit (not shown) of the housing 2120, as also described above and illustrated in FIG. 21. As another example, in the region of the housing 2220 where the first longitudinal axis 2232A and the second longitudinal axis 2232B appear to intersect in FIG. 22, the housing 2220 may be configured such that the first longitudinal axis 2232A and the second longitudinal axis 2232B (and thus the first irradiating light beam 2208A and the second irradiating light beam 2208B) are offset from each other, for example by a distance along a direction passing through the drawing sheet of FIG. 22. More generally, the particle detector 2200 may be configured such that particles in the first detection zone 2204A are irradiated solely by the first irradiating light beam 2208A, and particles in the second detection zone 2204B are irradiated solely by the second irradiating light beam 2208B (although particles in the second detection zone 2204B may have been previously irradiated by the first irradiating light beam 2208A while traveling through the first detection zone 2204A). This configuration enables particles in a sample fluid introduced into the particle detector 2200 to be subjected to irradiation at two different wavelengths, whereby two distinct measurements may be made. For example, the two distinct measurements may entail scattering at two different wavelengths, or scattering at one wavelength and fluorescence at another wavelength, etc.

In the present embodiment, at least one light detector is positioned to receive scattered or emitted measurement light from particles in the first detection zone 2204A, and at least one light detector is positioned to receive scattered or emitted measurement light from particles in the second detection zone 2204B. In the embodiment specifically illustrated in FIG. 22, one light detector 2228A is operatively associated with the first detection zone 2204A and two light detectors 2228B and 2228C are operatively associated with the second detection zone 2204B. The light detectors 2228A, 2228B, and 2228C may be flexible detectors as described herein, flat planar detectors as described herein, or a combination of both types of detectors. One or more of the light detectors 2228A, 2228B, and 2228C may include a plurality of individual light detectors (photo-responsive units), which may be electrically isolated from each other, connected in series, or connected in parallel, as described herein. The detection cavity (detection zones 2204A and 2204B) and the light detectors 2228A, 2228B, and 2228C may be elongated along the corresponding longitudinal axes 2232A and 2232B to increase the total detection area covered by the photo-responsive material or by an increased number of individual photo-responsive units. As in other embodiments, the measurement light incident on one or more of the light detectors 2228A, 2228B, and 2228C may be filtered by an optical filter (not specifically shown) in the manner described herein.

The particle detector 2200 may include separate light traps (not specifically shown) for receiving the first irradiating light beam 2208A and the second irradiating light beam 2208B, respectively. As illustrated in FIG. 22, the particle detector 2200 may also include a fluid moving device 2296 positioned so as to drive or assist the flow of sample fluid through the particle detector 2200. In the illustrated example, the fluid moving device 2296 is located at the outlet port of the sample outlet 2254, but may be located elsewhere. The particle detector 2200 may also include one or more other features described herein such as, for example, a data acquisition device, one or more devices for blocking stray/ambient light, beam-shaping optics, one or more heat sinks, structural transition sections of increasing and/or decreasing size, etc.

Embodiments of particle detectors disclosed herein may perform particle measurements with a high signal-to-noise ratio, thereby allowing for a high sensitivity. The lower the baseline (signal and variation in the signal detected when the light source is on but no particles are present), the better the particle detector can detect extremely small changes in scattered or emitted photons. In some embodiments disclosed herein, the signal baseline has been reduced by a factor of 10 in comparison to previously disclosed embodiments. Some embodiments disclosed herein include features that may result in reducing the signal baseline and increasing the signal-to-noise ratio. Examples of such embodiments include those providing apertures to block stray light and/or beam-shaping optics, as described above and illustrated in FIGS. 4 and 5. Other examples include, but are not limited to, those described below in conjunction with FIGS. 23, 24, and 25.

Figure 23:
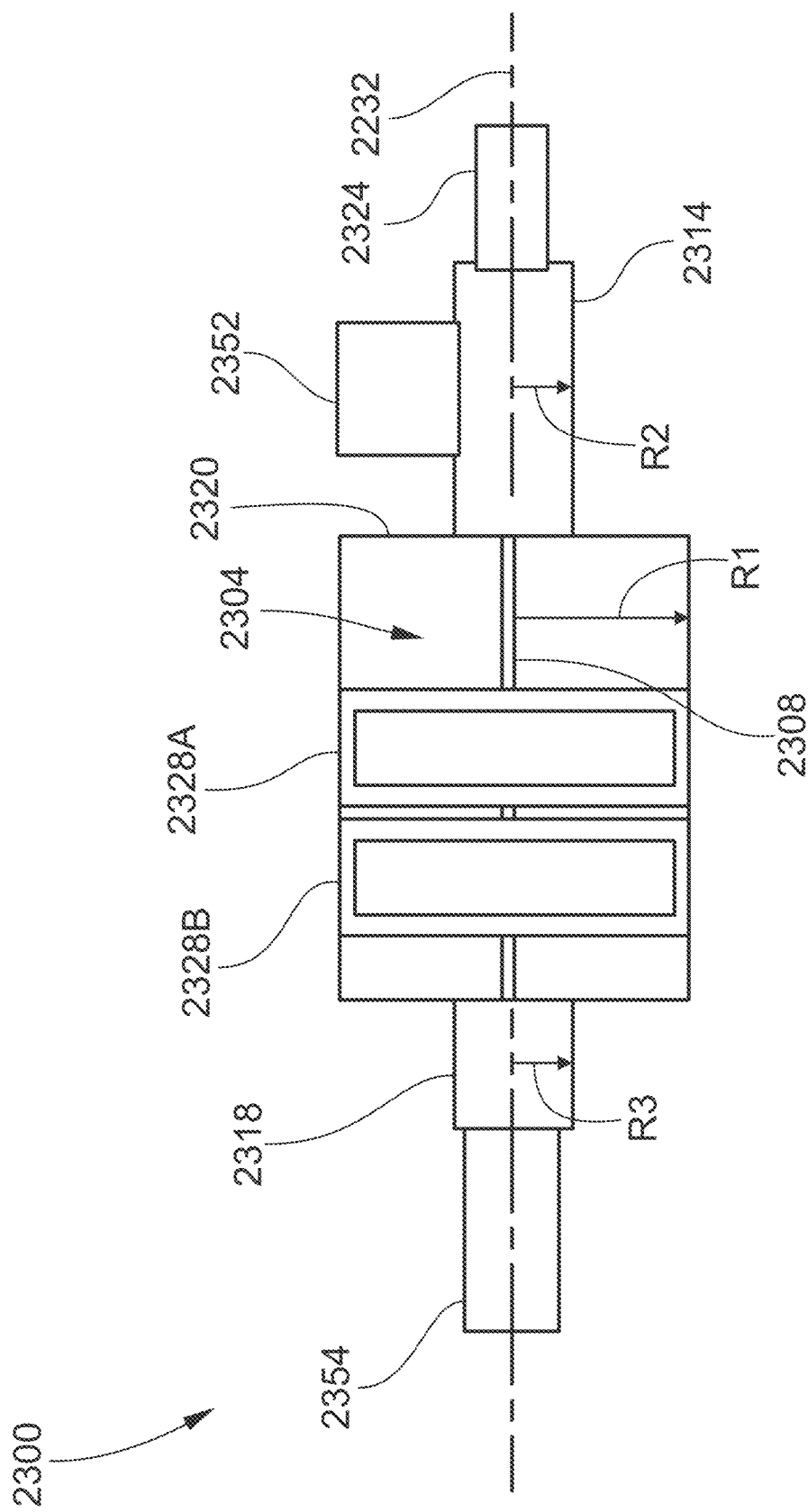
FIG. 23 is a schematic plan view of an example of a particle detector according to another embodiment.

FIG. 23 is a schematic plan view of an example of a particle detector 2300 according to another embodiment. The particle detector 2300 may include a housing 2320 enclosing a flow-through detection cavity 2304 that defines a sample flow path through the particle detector 2300 and an interaction region for particles and irradiating light, one or more light sources 2324 configured for emitting one or more irradiating light beams 2308, and one or more light detectors 2328A and 2328B for receiving scattered or emitted measurement light from the particles. The housing 2320 includes a sample inlet 2352 and a sample outlet 2354 positioned such that the housing 2320 defines a sample flow path from the sample inlet 2352, through the detection cavity 2304 along a longitudinal axis 2332 of the particle detector 2300, and to the sample outlet 2354. The housing 2320 may be configured such that the sample inlet 2352 and/or the sample outlet 2354 are oriented at an angle (e.g., ninety degrees) to the longitudinal axis 2332 to minimize entry of stray light into the detection cavity 2304, as described herein.

The housing 2320 may also include an axial inlet section 2314 and an axial outlet section 2318, both of which are positioned on the longitudinal axis 2332 on either side of the detection cavity 2304. The axial inlet section 2314 may define the portion of the sample flow path that leads directly into the detection cavity 2304 along the longitudinal axis 2332. The axial outlet section 2318 may define the portion of the sample flow path that leads directly out from the detection cavity 2304 along the longitudinal axis 2332. In some embodiments, the axial inlet section 2314 and the axial outlet section 2318 may be considered as being parts of the sample inlet 2352 and the sample outlet 2354, respectively. In some embodiments, the axial inlet section 2314 and the axial outlet section 2318 may be considered as being the inlet and the outlet of the detection cavity 2304, respectively.

The sizes of the detection cavity 2304, the axial inlet section 2314, and the axial outlet section 2318 may be defined by their respective internal characteristic dimensions. In the present context, the "characteristic dimension" of a structure or enclosure is the internal dimension of the structure or enclosure that best defines its size in view of its shape, and may be the maximum internal dimension of the structure or enclosure. For example, the characteristic dimension of a cylinder of circular cross-section is its diameter or, alternatively, its radius (the radial or transverse distance from the longitudinal axis to the inside surface of the cylinder). Similarly, the characteristic dimension of a cylinder of elliptical cross-section is its major axis, or half of the major axis. The characteristic dimension of a cylinder of polygonal or prismatic cross-section is the maximum length between a pair of opposing flat sides along the transverse or radial axis (orthogonal to the longitudinal axis) or, alternatively, half of that maximum length starting from the longitudinal axis. As a further example, FIG. 23 illustrates the detection cavity 2304, the axial inlet section 2314, and the axial outlet section 2318 as having characteristic dimensions designated R1, R2, and R3, respectively. The characteristic dimensions R1, R2, and R3 may also be referred to as "maximum radial dimensions" or "maximum transverse dimensions," regardless of the shapes of the detection cavity 2304, the axial inlet section 2314, and the axial outlet section 2318. Specifically, the characteristic dimension R1 is the maximum distance, in the radial or transverse direction, from the longitudinal axis 2332 to the inside surface of the housing 2320 demarcating the outer extent of the detection cavity 2304. Similarly, the characteristic dimensions R2 and R3 are, respectively, the maximum distances, in the radial or transverse direction, from the longitudinal axis 2332 to the inside surfaces of the axial inlet section 2314 and the axial outlet section 2318.

In the present embodiment, the housing 2320 is configured such that the detection cavity 2304 is significantly larger than the sample inlet 2352 and the sample outlet 2354 or, at least, significantly larger than the axial inlet section 2314 and the axial outlet section 2318. The larger size of the detection cavity 2304 relative to the sample inlet 2352 (or axial inlet section 2314) and the sample outlet 2354 (or axial outlet section 2318) may be achieved, for example, by increasing the size of the detection cavity 2304 in comparison to other particle detectors, reducing the size of the sample inlet 2352 and the sample outlet 2354 in comparison to other particle detectors, or both. By configuring the detection cavity 2304 to be significantly larger than the sample inlet 2352 and the sample outlet 2354, the light detectors 2328A and 2328B mounted to the inside or outside wall surrounding the detection cavity 2304 are located at a far distance away from the irradiating light beam 2308, which may significantly reduce the chance of stray light from the light source 2324 impinging on the light detectors 2328A and 2328B directly (instead of impinging on the particles). Eliminating incident light from the light source 2324 that is not due to scattering from particles or fluorescent emission may significantly reduce background noise. Meanwhile, the light detectors 2328A and 2328B are still located within a region that provides detection of scattered or emitted light in a matter of nanoseconds.

As described above, the sizes of the detection cavity 2304, the sample inlet 2352, and the axial outlet section 2318 may be defined by their respective characteristic dimensions. In some embodiments, the detection cavity 2304 has a characteristic dimension (maximum radial dimension R1 in the present example) in a range from 0.1% to 200% greater than the characteristic dimension (maximum radial dimensions R2 and R3 in the present example) of the axial inlet section 2314 and the axial outlet section 2318. The foregoing statements regarding size ranges assume that the characteristic dimension of the axial inlet section 2314 is the same as that of the axial outlet section 2318, i.e., R2=R3. In some embodiments, however, the characteristic dimension R2 of the axial inlet section 2314 may not be equal to the characteristic dimension R3 of the axial outlet section 2318. In such a case, the foregoing ranges of the characteristic dimension of the detection cavity 2304 are relative to the greater of the characteristic dimensions R2 and R3 of the axial inlet section 2314 and the axial outlet section 2318.

In one non-limiting example of the particle detector 2300, for a flow rate of 5 lpm, the detection cavity 2304 has a diameter (characteristic dimension) of 1.6 inches, and the axial inlet section 2314 and the axial outlet section 2318 each have a diameter of 0.6 inch.

In the present embodiment, two light detectors 2328A and 2328B are illustrated by example. As in other embodiments, the light detectors 2328A and 2328B may be flexible detectors as described herein, flat planar detectors as described herein, or a combination of both types of detectors. The light detectors 2328A and 2328B may be electrically isolated from each other, connected in series, or connected in parallel, as described herein. The detection cavity 2304 and the light detectors 2328A and 2328B may be elongated along the longitudinal axis 2332 to increase the total detection area covered by the photo-responsive material or by an increased number of individual photo-responsive units. The measurement light incident on one or more of the light detectors 2328A and 2328B may be filtered by an optical filter (not specifically shown) in the manner described herein. The particle detector 2300 may also include one or more other features described herein such as, for example, a light trap, a data acquisition device, one or more devices for blocking stray/ambient light, beam-shaping optics, one or more heat sinks, a fluid moving device, structural transition sections of increasing and/or decreasing size, etc.

Figure 24:
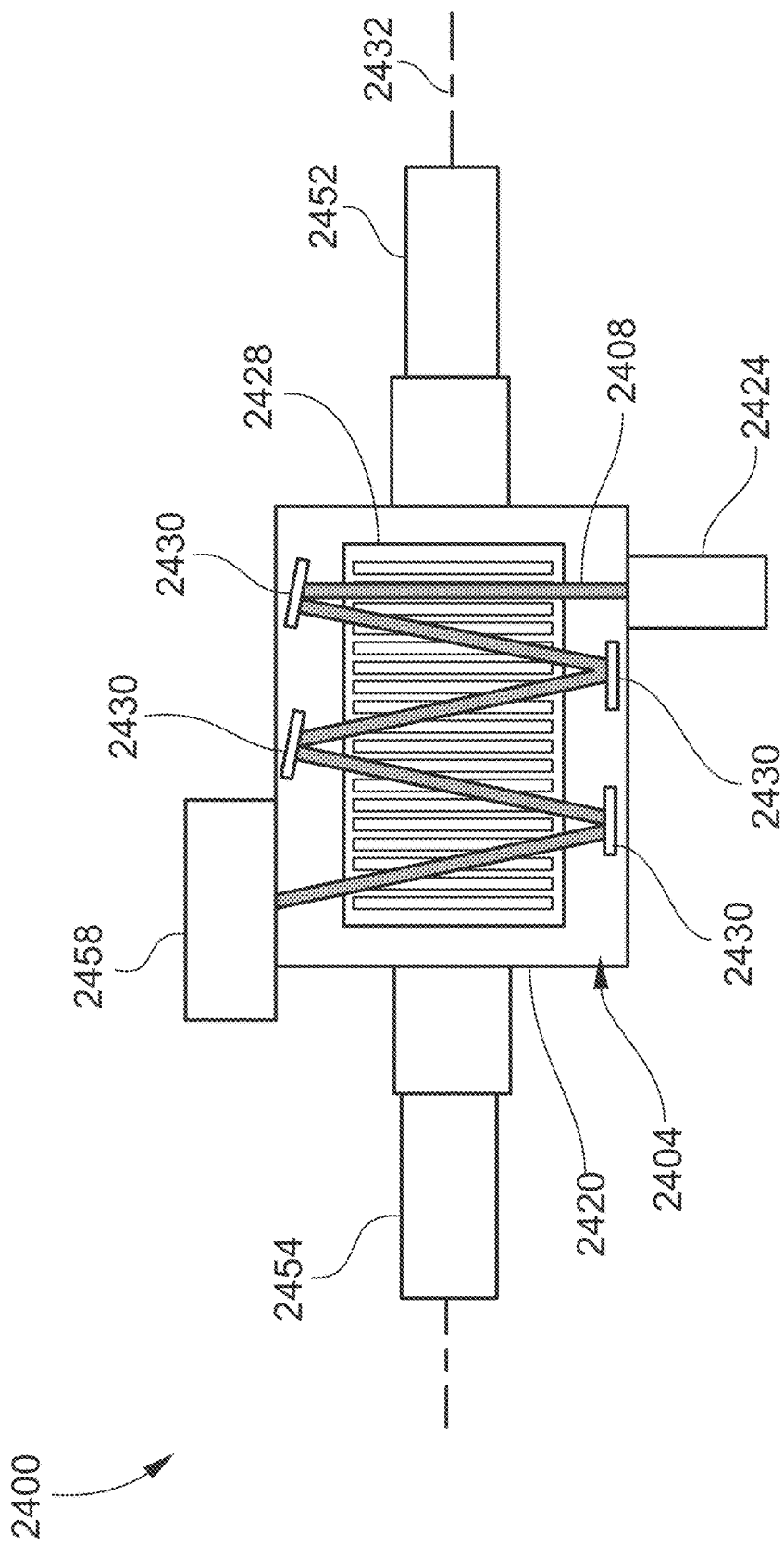
FIG. 24 is a schematic plan view of an example of a particle detector according to another embodiment.

FIG. 24 is a schematic plan view of an example of a particle detector 2400 according to another embodiment. The particle detector 2400 may include a housing 2420 enclosing a flow-through detection cavity 2404 that defines a sample flow path through the particle detector 2400 and an interaction region for particles and irradiating light, one or more light sources 2424 configured for emitting one or more irradiating light beams 2408, and one or more light detectors 2428 for receiving scattered or emitted measurement light from the particles. The housing 2420 includes a sample inlet 2452 and a sample outlet 2454 positioned such that the housing 2420 defines a sample flow path from the sample inlet 2452, through the detection cavity 2404 along a longitudinal axis 2432 of the particle detector 2400, and to the sample outlet 2454. Although not shown in FIG. 24, as in other embodiments the housing 2420 may be configured such that the sample inlet 2452 and/or the sample outlet 2454 are oriented at an angle (e.g., ninety degrees) to the longitudinal axis 2432 to minimize entry of stray light into the detection cavity 2404, as described herein.

In the present embodiment, the particle detector 2400 further includes one or more mirrors 2430. The mirrors 2430 are configured and positioned for reflecting the irradiating light beam 2408 one or more times, such that the irradiating light beam 2408 traverses the detection cavity 2404 two or more times prior to exiting the detection cavity 2404 (such as by terminating at a light trap 2458). That is, the path of the irradiating light beam 2408 turns one or more times, and sections of the beam path are at an angle to the longitudinal axis 2432. The direction of the beam path includes a component not only in the forward direction along the longitudinal axis 2432, but also a component in the transverse direction, i.e., along a transverse axis orthogonal to the longitudinal axis 2432. In the illustrated embodiment, four mirrors 2430 are provided whereby the irradiating light beam 2408 is turned four times. Other embodiments may include less or more than four mirrors 2430. Reflecting or "bouncing" the irradiating light beam 2408 across the detection cavity 2404 increases the effective power of the light source 2424 due to increasing the number of times the particles encounter the irradiating light beam 2408. Each time the irradiating light beam 2408 passes by the detection area of the light detector 2428 the intensity is almost doubled, although not completely as some loss occurs due to absorption and refraction due to imperfections of the mirrors 2430. This configuration provides a way to increase the sensitivity and signal output of the particle detector 2400 without increasing the power consumed by the particle detector 2400.

In the illustrated embodiment, the light source 2424 and the light trap 2458 are positioned (e.g., mounted to the housing 2420) at locations transversely or radially offset from the longitudinal axis 2432. More generally, however, the light source 2424 and the light trap 2458 may be positioned anywhere relative to the mirror(s) 2430 as needed for establishing a beam path that traverses the detection cavity 2404 two or more times. In the illustrated embodiment, the irradiating light beam 2408 enters the detection cavity 2404 in a purely transverse direction. More generally, however, the irradiating light beam 2408 may enter the detection cavity 2404 at any angle relative to the longitudinal axis 2432. In some embodiments, the mirror(s) 2430 may be located at the axial ends of the detection cavity 2404, in which case the irradiating light beam 2408 may enter the detection cavity 2404 at one of the axial ends thereof, at an angle to the longitudinal axis 2432.

The light detector(s) 2428 may have any configuration described herein. Thus, the light detector(s) 2428 may be flexible detectors as described herein, flat planar detectors as described herein, or a combination of both types of detectors. If more than one light detector 2428 (or more than one photo-responsive unit) is provided, the light detectors 2428 may be electrically isolated from each other, connected in series, or connected in parallel, as described herein. The detection cavity 2404 and the light detector(s) 2428 may be elongated along the longitudinal axis 2432 to increase the total detection area covered by the photo-responsive material or by an increased number of individual photo-responsive units. The measurement light incident on the light detector(s) 2428 may be filtered by an optical filter (not specifically shown) in the manner described herein. The particle detector 2400 may also include one or more other features described herein such as, for example, a data acquisition device, one or more devices for blocking stray/ambient light, beam-shaping optics, one or more heat sinks, a fluid moving device, structural transition sections of increasing and/or decreasing size, etc.

Figure 25:
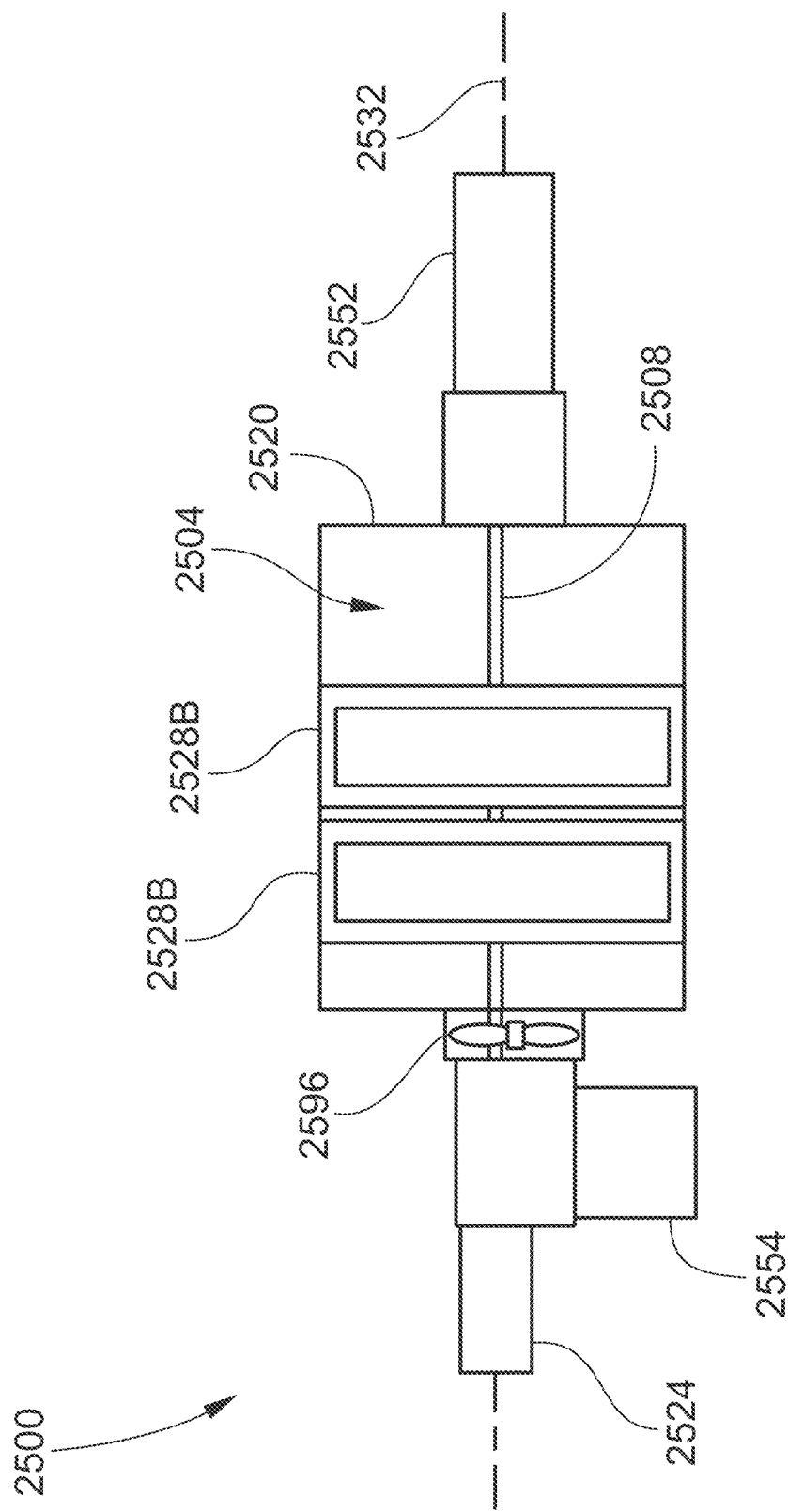
FIG. 25 is a schematic plan view of an example of a particle detector according to another embodiment.

FIG. 25 is a schematic plan view of an example of a particle detector 2500 according to another embodiment. The particle detector 2500 may include a housing 2520 enclosing a flow-through detection cavity 2504 that defines a sample flow path through the particle detector 2500 and an interaction region for particles and irradiating light, one or more light sources 2524 configured for emitting one or more irradiating light beams 2508, and one or more light detectors 2528A and 2528B for receiving scattered or emitted measurement light from the particles. The housing 2520 includes a sample inlet 2552 and a sample outlet 2554 positioned such that the housing 2520 defines a sample flow path from the sample inlet 2552, through the detection cavity 2504 along a longitudinal axis 2532 of the particle detector 2500, and to the sample outlet 2554. As in other embodiments, the housing 2520 may be configured such that the sample inlet 2552 and/or the sample outlet 2554 are oriented at an angle (e.g., ninety degrees) to the longitudinal axis 2532 to minimize entry of stray light into the detection cavity 2504, as described herein.

In the present embodiment, the particle detector 2500 further includes a beam chopper 2596. Generally, the beam chopper 2596 may be any device that is alternately movable (rotatable or translatable) into and out from the path of the irradiating light beam 2408 to chop or tune the irradiating light beam 2408 at a desired frequency. The frequency may be set so as to allow only the irradiating light beam 2408 to pass through the beam chopper 2596 and into the detection cavity 2504, and not unwanted stray light. As non-limiting examples, the beam chopper 2596 may be a spinning disk having holes or slots of appropriate sizes and positioned to cross through the beam path, or may be a fan with blades positioned to rotate through the beam path. In the illustrated embodiment, the beam chopper 2596 is a fan positioned to also serve as a fluid moving device. It may be desirable to position such a fan on the outlet side of the detection cavity 2504. In this case, the light source 2524 may also be positioned on the outlet side of the detection cavity 2504 such that the beam chopper 2596 is positioned between the light source 2524 and the detection cavity 2504, as illustrated.

The light detectors 2528A and 2528B may have any configuration described herein. Thus, the light detectors 2528A and 2528B may be flexible detectors as described herein, flat planar detectors as described herein, or a combination of both types of detectors. The light detectors 2528A and 2528B may be electrically isolated from each other, connected in series, or connected in parallel, as described herein. The detection cavity 2504 and the light detectors 2528A and 2528B may be elongated along the longitudinal axis 2532 to increase the total detection area covered by the photo-responsive material or by an increased number of individual photo-responsive units. The measurement light incident on the light detectors 2528A and 2528B may be filtered by an optical filter (not specifically shown) in the manner described herein. The particle detector 2500 may also include one or more other features described herein such as, for example, a light trap, a data acquisition device, one or more devices for blocking stray/ambient light, beam-shaping optics, one or more heat sinks, a fluid moving device, structural transition sections of increasing and/or decreasing size, etc.

EXAMPLE 6—Particle Detector Sensitivity

Figure 26:
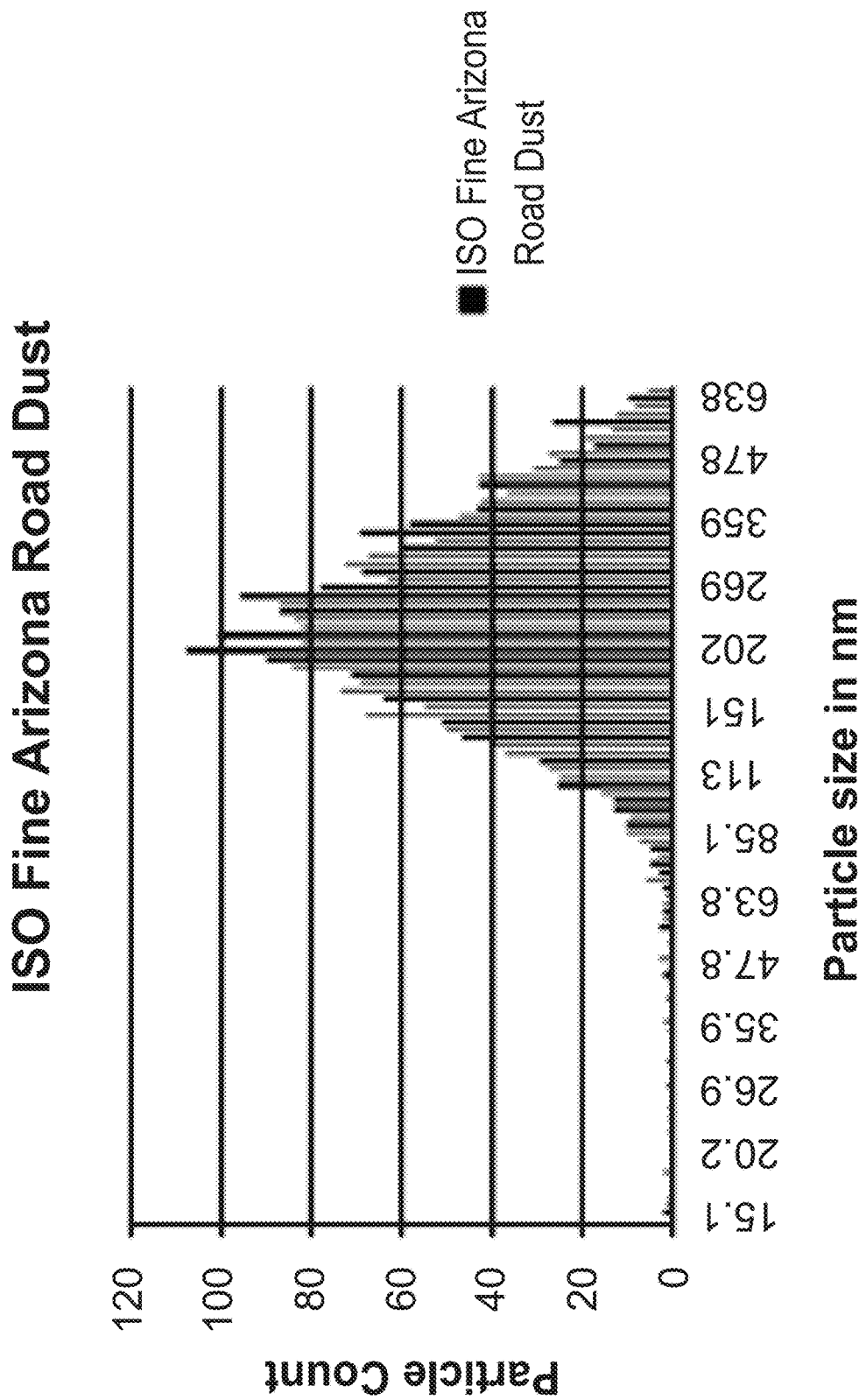
FIG. 26 is a SMPS plot of particle count as a function of particle size (in nm) acquired during testing of the particle detector described below in Example 6.

A particle detector consistent with embodiments described herein was tested. The test apparatus included a TSI Scanning Mobility Particle Sizer (SMPS) to measure particle size and particle size distribution. AZ Ultrafine test dust was utilized in the experiments. FIG. 26 is an SMPS plot of particle count as a function of particle size (in nm). FIG. 26 demonstrates that the particle detector was able to sense particle diameters below 0.3 μm, indicating that the particle detector exhibits low background noise and high sensitivity.

The present disclosure further encompasses various other embodiments providing various combinations of one or more features of the embodiments described above and illustrated in FIGS. 1 to 11, 19, and 21 to 25. Moreover, other embodiments may include one or more features disclosed in International Application No. PCT/2015/046080, filed Aug. 20, 2015, titled "SYSTEMS, DEVICES, AND METHODS FOR FLOW CONTROL AND SAMPLE MONITORING CONTROL," the content of which is incorporated by reference herein in its entirety.

Particle detectors such as described herein may provide one or more advantages. The particle detectors, particularly with the light detectors such as described herein, may provide a simple, low-cost solution to measuring particle concentration, and have been demonstrated through testing to be very sensitive, yielding high photon collection without requiring precision beam shaping optics (e.g., lenses and mirrors) in the measurement light path. That is, the light detector may enable the detection cavity to be free of beam shaping optics in the measurement light paths between the longitudinal axis and the photo-responsive material. In some embodiments, this is due at least in part to the light detector having a large-area active photo-responsive material that conformally surrounds the detection cavity, whereby the light detector is able to receive measurement light over nearly all directions of propagation. In other embodiments, the large area of the active photo-responsive material is realized by providing one or more light detectors having a flat, planar geometry. In some embodiments, the photo-responsive material may be a semiconductor having a low band gap, thereby increasing the sensitivity of the particle detector.

Moreover, with the active detection area being large and/or conformally surrounding the detection cavity, the light detector may enable the detection cavity to have a much larger volume compared to conventional devices, allowing for a significantly larger fraction and number of photons of scattered or fluorescent radiation to be collected during the transit time of the sample fluid past the light detector, and longer transit times (e.g., on the order of seconds or tenths of seconds for liter/min flow rates such as 5 L/min). This is in contrast to the light detectors utilized in conventional particle detectors, which are able to capture only a small fraction of photons over transit times of about 1 to 10 microseconds (μs). It will be noted that although the flow rate×transient time=constant; characteristics of the irradiation source, photo-responsive material, and measurement electronics may result in there being an optimum flow rate for sensitivity and/or LOD of the particle detector. The size of the detection cavity may also be increased to increase the spacing between the irradiating light beam and the light detector, which may reduce the detection of stray light from the irradiating light source.

In some embodiments, the particle detector is configured to provide a multi-reflected irradiating light beam that increases the measurement signal.

In some embodiments, the particle detector includes a beam chopper to minimize detection of unwanted stray light.

In some embodiments, the configuration of the particle detector facilitates the use or two or more sources of irradiating light, thereby enabling, if desired, the irradiation of particles at two or more different wavelengths. This may be useful, for example, for acquiring both scattering and fluorescent emission data.

The configuration and detection methodology of the light detector may also significantly relax requirements for accuracy and precision in the alignment of the light source in relation to the detection cavity or other components of the particle detector, as compared to conventional single particle counters with small detection cavities and multiple beam shaping optics. Light detectors such as described herein also enable measurement of the total concentration of particles in a volume of sample fluid ($\#/cm^3$) and changes in concentration, as opposed to conventional single particle counting techniques. This approach may simplify the optics required and eliminate the need for focusing the sample fluid into a single particle flow path. In addition, the simple geometry of the detection cavity (e.g., cylindrical) may simplify the assembly and maintenance of the particle detector, minimize deposition of particles on internal surfaces, and make cleaning easier.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A particle detector, comprising:
   a housing comprising a sample inlet and a sample outlet, and enclosing a detection cavity having a cavity length elongated along a longitudinal axis, wherein the housing defines a flow path for a sample fluid from the sample inlet, through the detection cavity along the longitudinal axis, and to the sample outlet;
   a light source configured for directing irradiating light through the detection cavity along the longitudinal axis to particles of the sample fluid flowing in the detection cavity; and
   a photo-responsive material facing the detection cavity and positioned along at least a portion of the cavity length at a radial distance from the longitudinal axis, wherein the photo-responsive material is configured for receiving measurement light propagating from the particles in a plurality of measurement light paths angled relative to the longitudinal axis.

2. The particle detector of claim 1, wherein the photo-responsive material comprises a semiconductor having a band gap in a range selected from the group consisting of: about 2 eV or less; from about 0.67 eV to about 2 eV; about 1.7 eV or less; from about 0.67 eV to about 1.7 eV; from about 1.1 eV to about 1.7 eV; about 1.1 eV or less; and from about 0.67 eV to about 1.1 eV.

3. The particle detector of claim 2, wherein the semiconductor comprises crystalline silicon.

4. The particle detector of claim 1, wherein the detection cavity is generally polygonal and comprises a plurality of planar sides, and the photo-responsive material comprises one or more photo-responsive materials positioned at one or more of the respective sides.

5. The particle detector of claim 1, wherein the photo-responsive material comprises a plurality of photo-responsive materials, and the plurality of photo-responsive materials comprises at least two photo-responsive materials electrically coupled in series with each other or in parallel with each other.

6. The particle detector of claim 1, wherein the light source comprises a plurality of light sources.

7. The particle detector of claim 6, wherein at least one of the light sources is configured for emitting the irradiating light at an irradiating wavelength different from the other light sources.

8. The particle detector of claim 6, wherein:
the plurality of light sources comprises a first light source and a second light source;
the detection cavity comprises a first detection zone and a second detection zone downstream from the first detection zone;
the first light source is configured for directing a first irradiating light through the first detection zone along the longitudinal axis; and
the second light source is configured for directing a second irradiating light through the second detection zone.

9. The particle detector of claim 8, wherein the photo-responsive material comprises a first photo-responsive material configured for receiving first measurement light propagating from particles in the first detection zone, and a second photo-responsive material configured for receiving second measurement light propagating from the particles in the second detection zone.

10. The particle detector of claim 8, wherein the second light source is positioned downstream from the first light source.

11. The particle detector of claim 8, comprising a mirror configured for directing the first irradiating light out from the first detection zone such that the first irradiating light does not enter the second detection zone.

12. The particle detector of claim 8, wherein the first detection zone and the second detection zone are positioned on the same longitudinal axis.

13. The particle detector of claim 12, comprising a mirror configured for directing the first irradiating light out from the first detection zone such that the first irradiating light does not enter the second detection zone, wherein the second light source is positioned in the housing downstream from the mirror.

14. The particle detector of claim 8, wherein the longitudinal axis is a first longitudinal axis, the first detection zone is positioned on the first longitudinal axis, and the second detection zone is positioned on a second longitudinal axis oriented at an angle to the first longitudinal axis.

15. The particle detector of claim 1, wherein:
the housing comprises an axial inlet section on the longitudinal axis between the sample inlet and the detection cavity, and an axial outlet section on the longitudinal axis between the detection cavity and the sample outlet, the axial inlet section and the axial outlet section having respective characteristic dimensions along a transverse direction orthogonal to the longitudinal axis; and
the detection cavity has a characteristic dimension in a range from 0.1% to 200% greater than the characteristic dimension of the axial inlet section and the axial outlet section.

16. The particle detector of claim 1, comprising a plurality of mirrors in the detection cavity, wherein:
the detection cavity has a dimension along a transverse axis orthogonal to the longitudinal axis; and
the mirrors are configured for reflecting the irradiating light one or more times such that the irradiating light traverses the detection cavity two or more times along directions having a component along the transverse axis.

17. The particle detector of claim 1, comprising a beam chopper configured for chopping the irradiating light.

18. The particle detector of claim 17, wherein the beam chopper comprises a fluid moving device configured for moving the sample fluid through the detection cavity.

19. A particle detector, comprising:
a housing comprising a sample inlet and a sample outlet, and enclosing a detection cavity having a cavity length along a longitudinal axis, wherein the housing defines a flow path for a sample fluid from the sample inlet, through the detection cavity, and to the sample outlet, wherein the detection cavity comprises a first detection zone and a second detection zone downstream from the first detection zone;
a first light source configured for directing a first irradiating light to particles of the sample fluid flowing in the first detection zone;
a second light source configured for directing a second irradiating light to particles of the sample fluid flowing in the second detection zone; and
a photo-responsive material facing the detection cavity and positioned along at least a portion of the cavity length at a radial distance from the longitudinal axis, wherein the photo-responsive material is configured for receiving measurement light propagating from the particles in a plurality of measurement light paths angled relative to the longitudinal axis.

20. The particle detector of claim 19, wherein the first light source is configured for emitting the irradiating light at an irradiating wavelength different from the second light source.

21. The particle detector of claim 19, wherein the photo-responsive material comprises a first photo-responsive material configured for receiving first measurement light propagating from particles in the first detection zone, and a second photo-responsive material configured for receiving second measurement light propagating from the particles in the second detection zone.

22. The particle detector of claim 21, wherein the photo-responsive material has a configuration selected from the group consisting of:
at least one of the first photo-responsive material and the second photo-responsive material has a flat planar geometry;

at least one of the first photo-responsive material and the second photo-responsive material has a flat planar geometry and comprises the semiconductor having a band gap 2 eV or less;

at least one of the first photo-responsive material and the second photo-responsive material is flexible and surrounds at least a portion of the detection cavity; and two or more of the foregoing.

23. The particle detector of claim 19, wherein the second light source is positioned downstream from the first light source.

24. The particle detector of claim 19, comprising a mirror configured for directing the first irradiating light out from the first detection zone such that the first irradiating light does not enter the second detection zone.

25. The particle detector of claim 19, wherein the first detection zone and the second detection zone are positioned on the same longitudinal axis.

26. The particle detector of claim 25, comprising a mirror configured for directing the first irradiating light out from the first detection zone such that the first irradiating light does not enter the second detection zone, wherein the second light source is positioned in the housing downstream from the mirror.

27. The particle detector of claim 19, wherein the first detection zone is positioned on a first longitudinal axis, and the second detection zone is positioned on a second longitudinal axis oriented at an angle to the first longitudinal axis.

28. A particle detector, comprising:
a housing comprising a sample inlet and a sample outlet, and enclosing a detection cavity having a cavity length elongated along a longitudinal axis, wherein:
the housing defines a flow path for a sample fluid from the sample inlet, through the detection cavity, and to the sample outlet along the longitudinal axis;
the sample inlet comprises an axial inlet section on the longitudinal axis;
the sample outlet comprises an axial outlet section on the longitudinal axis;
the sample outlet comprises an axial outlet section on the longitudinal axis;
the axial inlet section and the axial outlet section having respective maximum radial dimensions along a radial direction orthogonal to the longitudinal axis; and
the detection cavity has a characteristic dimension in a range from 0.1% to 200% greater than the characteristic dimension of the axial inlet section and the axial outlet section;
a light source configured for directing irradiating light through the detection cavity along the longitudinal axis to particles of the sample fluid flowing in the detection cavity; and
a photo-responsive material facing the detection cavity and positioned along at least a portion of the cavity length at a radial distance from the longitudinal axis, wherein the photo-responsive material is configured for receiving measurement light propagating from the particles in a plurality of measurement light paths angled relative to the longitudinal axis.

29. The particle detector of claim 28, wherein the photo-responsive material has a configuration selected from the group consisting of:
the photo-responsive material has a flat planar geometry;
the photo-responsive material has a flat planar geometry and comprises the semiconductor having a band gap 2 eV or less; and
the photo-responsive material is flexible and surrounds at least a portion of the detection cavity.

30. A particle detector, comprising:
a housing comprising a sample inlet and a sample outlet, and enclosing a detection cavity having a cavity length elongated along a longitudinal axis, wherein the housing defines a flow path for a sample fluid from the sample inlet, through the detection cavity, and to the sample outlet along the longitudinal axis;
a light source configured for directing irradiating light through the detection cavity along the longitudinal axis to particles of the sample fluid flowing in the detection cavity;
a plurality of mirrors in the detection cavity, wherein:
the detection cavity has a dimension along a transverse axis orthogonal to the longitudinal axis; and
the mirrors are configured for reflecting the irradiating light one or more times such that the irradiating light traverses the detection cavity two or more times along directions having a component along the transverse axis; and
a photo-responsive material facing the detection cavity and positioned along at least a portion of the cavity length at a radial distance from the longitudinal axis, wherein the photo-responsive material is configured for receiving measurement light propagating from the particles in a plurality of measurement light paths angled relative to the longitudinal axis.

31. The particle detector of claim 30, wherein the photo-responsive material has a configuration selected from the group consisting of:
the photo-responsive material has a flat planar geometry;
the photo-responsive material has a flat planar geometry and comprises the semiconductor having a band gap 2 eV or less; and
the photo-responsive material is flexible and surrounds at least a portion of the detection cavity.

32. A particle detector, comprising:
a housing comprising a sample inlet and a sample outlet, and enclosing a detection cavity having a cavity length along a longitudinal axis, wherein the housing defines a flow path for a sample fluid from the sample inlet, through the detection cavity, and to the sample outlet;
a light source configured for directing irradiating light along the longitudinal axis to particles of the sample fluid flowing in the detection cavity;
a beam chopper configured for chopping the irradiating light; and
a photo-responsive material facing the detection cavity and positioned along at least a portion of the cavity length at a radial distance from the longitudinal axis, wherein the photo-responsive material is configured for receiving measurement light propagating from the particles in a plurality of measurement light paths angled relative to the longitudinal axis.

33. The particle detector of claim 32, wherein the photo-responsive material has a configuration selected from the group consisting of:
the photo-responsive material has a flat planar geometry;
the photo-responsive material has a flat planar geometry and comprises the semiconductor having a band gap 2 eV or less; and
the photo-responsive material is flexible and surrounds at least a portion of the detection cavity.

34. The particle detector of claim 32, wherein the beam chopper comprises a fluid moving device configured for moving the sample fluid through the detection cavity.

\* \* \* \* \*

UNITED STATES PATENT AND TRADEMARK OFFICE
CERTIFICATE OF CORRECTION

PATENT NO. : 9,915,600 B2  
APPLICATION NO. : 15/048199  
DATED : March 13, 2018  
INVENTOR(S) : Walls et al.

Page 1 of 1

It is certified that error appears in the above-identified patent and that said Letters Patent is hereby corrected as shown below:

In the Specification

Please correct Column 1 to insert under Line 3:
--This invention was made with government support under D14PC00196 awarded by the Department of Homeland Security, Science and Technology. The government has certain rights in the invention.--

Signed and Sealed this
Twenty-first Day of November, 2023

Katherine Kelly Vidal
*Director of the United States Patent and Trademark Office*